(12) United States Patent
Merla et al.

(10) Patent No.: US 7,728,028 B2
(45) Date of Patent: Jun. 1, 2010

(54) SUBSTITUTED IMIDAZOLINE COMPOUNDS

(75) Inventors: Beatrix Merla, Aachen (DE); Stefan Oberboersch, Aachen (DE); Bernd Sundermann, Aachen (DE); Werner Englberger, Stolberg (DE); Hagen-Heinrich Hennies, Simmerath (DE); Heinz Graubaum, Erkner (DE)

(73) Assignee: Gruenenthal GmbH, Aachen (DE)

( * ) Notice: Subject to any disclaimer, the term of this patent is extended or adjusted under 35 U.S.C. 154(b) by 69 days.

(21) Appl. No.: 12/143,566

(22) Filed: Jun. 20, 2008

(65) Prior Publication Data

US 2009/0048323 A1 Feb. 19, 2009

Related U.S. Application Data

(63) Continuation of application No. PCT/EP2006/012221, filed on Dec. 19, 2006.

(30) Foreign Application Priority Data

Dec. 22, 2005 (DE) .................. 10 2005 061 430

(51) Int. Cl.
*A61K 31/4164* (2006.01)
*C07D 233/06* (2006.01)
*A61P 25/30* (2006.01)
*A61P 25/24* (2006.01)

(52) U.S. Cl. ............... 514/401; 548/347.1; 548/355.1

(58) Field of Classification Search .............. None
See application file for complete search history.

(56) References Cited

U.S. PATENT DOCUMENTS 6,673,794 B2    1/2004 Puetz et al.
7,608,619 B2 *  10/2009 Merla et al. ............ 514/236.8

FOREIGN PATENT DOCUMENTS

| EP | 1 486 490 A1 | 12/2004 |
| WO | WO 99/09829 A1 | 3/1999 |
| WO | WO 99/09979 A1 | 3/1999 |
| WO | WO 01/49654 A2 | 7/2001 |
| WO | WO 03/101969 A1 | 12/2003 |

OTHER PUBLICATIONS

International Search Report dated May 8, 2007 (one (1) page).

\* cited by examiner

*Primary Examiner*—Kamal A Saeed
(74) *Attorney, Agent, or Firm*—Crowell & Moring LLP

(57) ABSTRACT

Substituted imidazoline derivatives corresponding to Formula I:

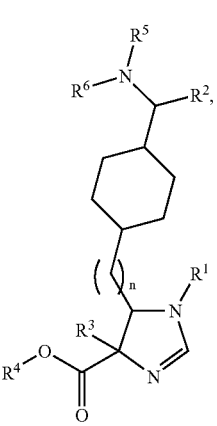

a method for producing them from substituted aldehyde compounds of Formula B:

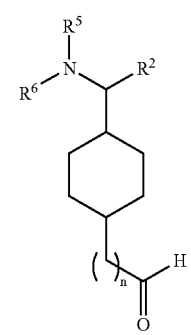

and the use of such imidazoline derivatives and aldehyde compounds to treat pain, depression, urinary incontinence, diarrhea, pruritus, alcohol and drug misuse, drug dependency, lethargy and/or anxiety.

28 Claims, No Drawings

SUBSTITUTED IMIDAZOLINE COMPOUNDS

CROSS REFERENCE TO RELATED APPLICATIONS

This application is a continuation of international patent application no. PCT/EP2006/012221, filed Dec. 19, 2006, designating the United States of America, and published in German on Jul. 19, 2007 as WO 2007/079927, the entire disclosure of which is incorporated herein by reference. Priority is claimed based on Federal Republic of Germany patent application no. DE 10 2005 061 430.2, filed Dec. 22, 2005.

BACKGROUND OF THE INVENTION

The present invention relates to substituted imidazoline derivatives, processes for their preparation, medicaments containing these compounds, and the use of substituted imidazoline derivatives for the preparation of medicaments.

The treatment of chronic and non-chronic pain states is extremely important in medicine. There is therefore a widespread need for highly effective pain treatments. The urgent need for a patient-friendly and targeted treatment of chronic and non-chronic pain states, which from the patient's point of view is hereinafter understood to mean the successful and satisfactory handling and treatment of pain, is well documented in the large number of scientific papers and articles that have appeared in recent years in the field of applied analgesics and in basic research on nociception.

Conventional opioids such as morphine are highly effective in the treatment of severe to extremely severe pain. Their use is however limited by their known side effects, for example respiratory depression, nausea, vomiting, sedation, constipation and development of tolerance. Also, they are less effective in neuropathic or incidental pain, including in particular tumour patients.

In Org. Lett. 2003, 5, 3759-3762 substituted imidazolines with a carboxylic acid/carboxylic acid ester group are likewise disclosed, which however are not coupled to an aminomethyl-substituted cyclohexane ring.

SUMMARY OF THE INVENTION

A basic object of the invention was to provide new analgesically effective substances that are suitable for treating pain, in particular also chronic and neuropathic pain.

The invention accordingly provides substituted imidazoline derivatives of the general Formula I

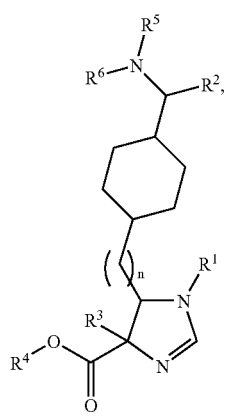

wherein
n is 0, 1 or 2;
$R^1$ denotes $C_{1-8}$-alkyl, saturated or unsaturated, branched or unbranched, unsubstituted or monosubstituted or polysubstituted; $C_{3-8}$-cycloalkyl, saturated or unsaturated, unsubstituted or monosubstituted or polysubstituted; an aryl or heteroaryl radical bonded via a $C_{1-3}$-alkyl chain, in each case unsubstituted or monosubstituted or polysubstituted;
$R^2$ denotes aryl or heteroaryl, in each case unsubstituted or monosubstituted or polysubstituted; an aryl radical bonded via a $C_{1-3}$-alkyl chain, in each case unsubstituted or monosubstituted or polysubstituted;
$R^3$ denotes $C_{1-8}$-alkyl, saturated or unsaturated, branched or unbranched, unsubstituted or monosubstituted or polysubstituted; an aryl radical bonded via a $C_{1-3}$-alkyl chain, in each case unsubstituted or monosubstituted or polysubstituted;
$R^4$ denotes H, $C_{1-4}$-alkyl, or an aryl radical bonded via a $C_{1-3}$-alkyl chain;
$R^5$ and $R^6$ independently of one another denote H; $C_{1-6}$-alkyl, in each case saturated or unsaturated, branched or unbranched, wherein $R^5$ and $R^6$ do not simultaneously denote H, or
$R^5$ and $R^6$ together denote $-CH_2CH_2OCH_2CH_2-$ or $=(CH_2)_{3-6}-$, in the form of the racemate; in the form of the enantiomers, diastereomers, mixtures of the enantiomers or diastereomers or in the form of an individual enantiomer or diastereomer; in the form of the bases and/or salts of physiological compatible acids. The compounds have an affinity for the μ-opioid receptor.

The expressions "$C_{1-8}$-alkyl", "$C_{1-3}$-alkyl", "$C_{1-4}$-alkyl" and "$C_{1-6}$-alkyl" include in the context of the present invention acyclic saturated or unsaturated hydrocarbon radicals, which can be branched or straight-chain, as well as unsubstituted or monosubstituted or polysubstituted, with 1 to 8 or 1 to 3 C atoms or 1 to 4 C atoms or 1 to 6 C atoms, i.e. $C_{1-8}$-alkanyls, $C_{2-8}$-alkenyls and $C_{2-8}$-alkinyls, or $C_{1-3}$-alkanyls, $C_{2-3}$-alkenyls and $C_{2-3}$-alkinyls, or $C_{1-4}$-alkanyls, $C_{2-4}$-alkenyls and $C_{2-4}$-alkinyls, or $C_{1-6}$-alkanyls, $C_{2-6}$-alkenyls and $C_{2-6}$-alkinyls. In this connection alkenyls have at least one C=C double bond and alkinyls have at least one C—C triple bond. Advantageously the alkyl is selected from the group comprising methyl, ethyl, n-propyl, 2-propyl, n-butyl, iso-butyl, sec.-butyl, tert.-butyl, n-pentyl, iso-pentyl, neopentyl, n-hexyl, 2-hexyl, n-heptyl, n-octyl, 1,1,3,3-tetramethylbutyl; ethylenyl (vinyl), ethinyl, propenyl ($-CH_2CH=CH_2$, $-CH=CH-CH_3$, $-C(=CH_2)-CH_3$), propinyl ($-CH-C\equiv CH$, $-C\equiv C-CH_3$), butenyl, butinyl, pentenyl, pentinyl, hexenyl, hexinyl, heptenyl, heptinyl, octenyl and octinyl. Particularly preferred are methyl, ethyl, n-propyl, n-butyl, sec-butyl, iso-butyl.

The expression "cycloalkyl" or "$C_{3-8}$-cycloalkyl" denotes, for the purposes of the present invention, cyclic hydrocarbons with 3, 4, 5, 6, 7 or 8 carbon atoms, in which the hydrocarbon radicals can be saturated or unsaturated (but not aromatic), unsubstituted or monosubstituted or polysubstituted. With regard to cycloalkyl the expression also includes saturated or unsaturated (but not aromatic) cycloalkyls in which one or two carbon atoms is/are replaced by a heteroatom S, N or O. Advantageously the $C_{3-8}$-cycloalkyl is selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

The expression "aryl" denotes within the meaning of the present invention aromatic hydrocarbons, inter alia phenyls and naphthyls. The aryl radicals can also be condensed with further saturated, (partially) unsaturated or aromatic ring systems. Each aryl radical can be unsubstituted or monosubstituted or polysubstituted, wherein the aryl substituents can be identical or different and can be in any arbitrary and possible position of the aryl radical. Advantageously aryl is selected from the group containing phenyl, 1-naphthyl, 2-naphthyl, which can in each case be unsubstituted or monosubstituted or polysubstituted. The phenyl radical is particularly advantageous.

The expression "heteroaryl" denotes a 5-, 6- or 7-membered cyclic aromatic radical that contains at least 1, possibly also 2, 3, 4 or 5 heteroatoms, in which the heteroatoms are identical or different and the heterocycle can be unsubstituted or monosubstituted or polysubstituted; in the case of the substitution on the heterocycle, the substituents can be identical or different and can be in any arbitrary and possible position of the heteroaryl. The heterocycle can also be part of a bicyclic or polycyclic system. Preferred heteroatoms are nitrogen, oxygen and sulfur. It is preferred that the heteroaryl radical is selected from the group containing pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazoyl, pyridyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the bonding to the compounds of the general structure I can be effected via any arbitrary and possible ring member of the heteroaryl radical. Pyridyl, furyl, thienyl and indolyl are particularly preferred.

The expression "aryl or heteroaryl bonded via $C_{1-3}$-alkyl" denotes, for the purposes of the present invention, that $C_{1-3}$-alkyl and aryl or heteroaryl have the meanings defined above and that the aryl or heteroaryl radical is bonded via a $C_{1-3}$-alkyl group to the compound of the general structure 1. Within the context of the present invention benzyl and phenethyl are particularly advantageous.

In connection with "alkyl" or "cycloalkyl", the term "substituted" is understood within the context of the present invention to denote the substitution of a hydrogen atom by F, Cl, Br, I, —CN, $NH_2$, NH—$C_{1-6}$-alkyl, NH—$C_{1-6}$-alkyl-OH, N($C_{1-6}$ -alkyl)$_2$, N($C_{1-6}$-alkyl-OH)$_2$, $NO_2$, SH, S—$C_{1-6}$-alkyl, S-benzyl, O—$C_{1-6}$-alkyl, OH, O—$C_{1-6}$-alkyl-OH, =O, $C_{1-6}$-alkyl, benzyl, O-benzyl, C(=O)$C_{1-6}$-alkyl, $CO_2H$, $CO_2$—$C_{1-6}$-alkyl, wherein polysubstituted radicals are understood to be those radicals that are polysubstituted, for example disubstituted or trisubstituted, either on different atoms or on the same atoms, for example trisubstituted on the same C atom as in the case of $CF_3$ or —$CH_2CF_3$, or at different sites as in the case of —CH(OH)—CH=CH—$CHCl_2$. The polysubstitution can take place with the same or with different substituents. For the purposes of the present invention "monosubstituted or polysubstituted" in connection with alkyl particularly preferably denotes S—$CH_3$, S-benzyl or $COOCH_3$.

With regard to "aryl" and "heteroaryl", within the context of the present invention "monosubstituted or polysubstituted" denotes monosubstitution or polysubstitution, for example disubstitution, trisubstitution or tetrasubstitution of one or more hydrogen atoms of the ring system by F, Cl, Br, I, CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CO_2$—$C_{1-6}$-alkyl, $CF_3$, $C_{1-6}$-alkyl, on one or possibly different atoms (in which connection a substituent can optionally for its part be substituted). The polysubstitution can in this connection be carried out with the same or with different substituents. For "aryl" and "heteroaryl", preferred substituents in this case are F, —Cl, —$CF_3$, —O—$CH_3$, methyl, ethyl, n-propyl, nitro, tert.-butyl, and —CN. Particularly preferred are —F and —Cl.

The expression "salt formed with a physiologically compatible acid" is understood within the context of the present invention to mean salts of the respective active substance with inorganic or organic acids which are physiologically compatible, especially when used in humans and/or mammals. The hydrochloride is particularly preferred. Examples of physiologically compatible acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydrol $\lambda^6$-benzo[d]isothiazol-3-one (saccharinic acid), monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid and/or aspartic acid. Hydrochloric acid is particularly preferred.

The groups —$(CH_2)_{3-6}$— and —$(CH_2)_{4-5}$— are understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, and —$CH_2$—$CH_2$—$CH_2$—$CH_2$— and —$CH_2$—$CH_2$—$CH_2$—$CH_2$—$CH_2$—, respectively.

Preferred within the meaning of the present invention are those substituted imidazoline derivatives in which $R^1$ denotes $C_{1-8}$-alkyl, branched or unbranched, saturated or unsaturated, unsubstituted or monosubstituted or polysubstituted with F, Cl, —CN, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, S-benzyl, OH, O—$C_{1-6}$-alkyl-OH, O—$C_{1-6}$-alkyl, O-benzyl, benzyl, C(=O)$C_{1-6}$-alkyl, $CO_2H$, $CO_2$—$C_{1-6}$-alkyl; $C_{3-8}$-cycloalkyl, in each case unsubstituted or monosubstituted or polysubstituted with F, Cl, —CN, NH—$C_{1-6}$-alkyl, NH—$C_{1-6}$ -alkyl-OH, N($C_{1-6}$-alkyl)$_2$, N($C_{1-6}$-alkyl-OH)$_2$, $NO_2$, SH, S—$C_{1-6}$-alkyl, S-benzyl, benzyl, $C_{1-6}$-alkyl, OH, O—$C_{1-6}$-alkyl-OH, O-benzyl, C(=O)$C_{1-6}$-alkyl, $CO_2H$, $CO_2$—$C_{1-6}$-alkyl; a phenyl, furyl, thienyl or indolyl radical bonded via a $C_{1-3}$-alkyl chain, in each case unsubstituted or monosubstituted or polysubstituted with F, Cl, CN, NH—$C_{1-6}$ -alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CO_2$—$C_{1-6}$-alkyl, $CF_3$, $C_{1-6}$-alkyl.

Preferably $R^1$ denotes $C_{1-8}$-alkyl, branched or unbranched, unsubstituted or monosubstituted or polysubstituted with F, Cl, —CN, SH, S—$C_{1-6}$-alkyl, S-benzyl, OH, O-benzyl, O—$C_{1-6}$-alkyl, $CO_2H$, $CO_2$—$C_{1-6}$-alkyl; $C_{3-8}$-cycloalkyl, in each case unsubstituted or monosubstituted or polysubstituted with F, Cl, —CN, SH, S—$C_{1-6}$-alkyl, $C_{1-6}$-alkyl, S-benzyl, OH, O— benzyl, O—$C_{1-6}$-alkyl, $CO_2H$, $CO_2$—$C_{1-6}$-alkyl; a phenyl radical bonded via a $C_{1-3}$-alkyl chain, in each case unsubstituted or monosubstituted or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, $C_{1-6}$-alkyl.

In particular, $R^1$ denotes $C_{1-8}$-alkyl, branched or unbranched; $C_{3-8}$-cycloalkyl; a phenyl radical bonded via a $C_{1-3}$-alkyl chain.

Particularly preferred are imidazoline derivatives in which $R^1$ denotes cyclohexyl, n-propyl, n-butyl, phenethyl or benzyl.

Preferred within the context of the present invention are also substituted imidazoline derivatives in which $R^2$ denotes phenyl, thienyl or pyridyl, in each case unsubstituted or monosubstituted or polysubstituted with F, Cl, CN, NH—$C_{1-6}$-alkyl, NH—$C_{1-6}$-alkyl-OH, N($C_{1-6}$-alkyl)$_2$, N($C_{1-6}$-alkyl-OH)$_2$, NO$_2$, SH, S—$C_{1-6}$-alkyl, OH, O—$C_{1-6}$-alkyl, O—$C_{1-6}$-alkyl-OH, C(=O)$C_{1-6}$-alkyl, CO$_2$H, CO$_2$—$C_{1-6}$-alkyl, CF$_3$, $C_{1-6}$-alkyl; an aryl radical bonded via a $C_{1-3}$-alkyl chain, in each case unsubstituted or monosubstituted or polysubstituted with F, Cl, CN, NH—$C_{1-6}$-alkyl, NH—$C_{1-6}$-alkyl —OH, N($C_{1-6}$-alkyl)$_2$, N($C_{1-6}$-alkyl-OH)$_2$, NO$_2$, SH, S—$C_{1-6}$-alkyl, OH, O—$C_{1-6}$-alkyl, O—$C_{1-6}$-alkyl-OH, C(=O)$C_{1-6}$-alkyl, CO$_2$H, CO$_2$—$C_{1-6}$-alkyl, CF$_3$, $C_{1-6}$-alkyl.

Preferably $R^2$ denotes phenyl or thienyl, in each case unsubstituted or monosubstituted or polysubstituted with F, Cl, CN, NO$_2$, SH, S—$C_{1-6}$-alkyl, OH, O—$C_{1-6}$-alkyl, CO$_2$H, CO$_2$—$C_{1-6}$-alkyl, CF$_3$, $C_{1-6}$-alkyl; a phenyl radical bonded via a $C_{1-3}$-alkyl chain, in each case unsubstituted or monosubstituted or polysubstituted with F, Cl, CN, NO$_2$, SH, S—$C_{1-6}$-alkyl, OH, O—$C_{1-6}$-alkyl, CO$_2$H, CO$_2$—$C_{1-6}$-alkyl, CF$_3$, $C_{1-6}$-alkyl.

In particular, $R^2$ denotes phenyl, unsubstituted or monosubstituted or polysubstituted with F, Cl, OH, OCH$_3$, CF$_3$ or CH$_3$; thienyl; or a phenyl radical bonded via a $C_{1-3}$-alkyl chain, unsubstituted or monosubstituted or polysubstituted with F, Cl, CN, OH, OCH$_3$, CF$_3$ or CH$_3$.

Most particularly preferred are imidazoline derivates in which $R^2$ denotes phenyl, unsubstituted or monosubstituted with Cl or F, or denotes thienyl or phenethyl.

Also preferred within the meaning of the present invention are substituted imidazoline derivatives in which $R^3$ denotes $C_{1-8}$-alkyl, saturated or unsaturated, branched or unbranched, unsubstituted or monosubstituted or polysubstituted with F, Cl, —CN, SH, S—$C_{1-6}$-alkyl, S-benzyl, benzyl, OH, O-benzyl, O—$C_{1-6}$-alkyl, CO$_2$H, CO$_2$—$C_{1-6}$-alkyl; a phenyl radical bonded via a $C_{1-3}$-alkyl chain, in each case unsubstituted or monosubstituted or polysubstituted with F, Cl, CN, NH—$C_{1-6}$-alkyl, NH—$C_{1-6}$-alkyl-OH, N($C_{1-6}$-alkyl)$_2$, N($C_{1-6}$-alkyl-OH)$_2$, NO$_2$, SH, S—$C_{1-6}$-alkyl, OH, O—$C_{1-6}$-alkyl, O—$C_{1-6}$-alkyl-OH, C(=O)$C_{1-6}$-alkyl, CO$_2$H, CO$_2$—$C_{1-6}$-alkyl, CF$_3$, $C_{1-6}$-alkyl.

Preferably $R^3$ denotes $C_{1-8}$-alkyl, branched or unbranched, unsubstituted or monosubstituted or polysubstituted with F, Cl, —CN, SH, S—$C_{1-6}$-alkyl, S-benzyl, OH, O-benzyl, O—$C_{1-6}$-alkyl, CO$_2$H, CO$_2$—$C_{1-6}$-alkyl; a phenyl radical bonded via a $C_{1-3}$-alkyl chain, in each case unsubstituted or monosubstituted or polysubstituted with F, Cl, CN, NO$_2$, SH, S—$C_{1-6}$-alkyl, OH, O—$C_{1-6}$-alkyl, CO$_2$H, CO$_2$—$C_{1-6}$-alkyl, CF$_3$, $C_{1-6}$-alkyl.

In particular, $R^3$ denotes $C_{1-8}$-alkyl, branched or unbranched, unsubstituted or monosubstituted or polysubstituted with S—CH$_3$, S-benzyl or COOCH$_3$; a phenyl radical bonded via a $C_{1-3}$-alkyl chain, in each case unsubstituted or monosubstituted or polysubstituted with F, Cl, CN, OH, O—CH$_3$, CF$_3$, CH$_3$.

Particularly preferred are imidazoline derivatives in which $R^3$ denotes sec-butyl, iso-butyl, n-butyl, n-propyl, CH$_3$, CH$_2$—CH$_2$ COOCH$_3$, CH$_2$—S-benzyl, CH$_2$CH$_2$—S—CH$_3$, CH$_2$—S—CH$_3$ or 4-Cl-benzyl.

Also preferred within the context of the present invention are imidazoline derivatives in which $R^4$ denotes $C_{1-4}$-alkyl.

Particularly preferred are imidazoline derivatives in which $R^4$ denotes CH$_3$.

Also preferred within the meaning of the present invention are imidazoline derivatives in which $R^5$ and $R^6$ independently of one another denote H or $C_{1-6}$-alkyl, wherein $R^5$ and $R^6$ do not simultaneously denote H.

Furthermore preferred are imidazoline derivatives in which the radicals $R^5$ and $R^6$ together denote CH$_2$CH$_2$OCH$_2$CH$_2$ or (CH$_2$)$_{4-5}$.

Preferably n is 0 or 1.

Particularly preferred are imidazoline derivatives in which $R^5$ and $R^6$ denote CH$_3$.

Most particularly preferred are substituted imidazoline derivatives selected from the group consisting of:

1-cyclohexyl-5-{4-[dimethylamino-(3-fluorophenyl)-methyl]-cyclohexyl}-4-isobutyl-4,5-dihydro-1H-imidazole-4-carboxylic acid methyl ester;

4-(4-chlorobenzyl)-1-cyclohexyl-5-{4-[dimethylamino-(3-fluorophenyl)-methyl]-cyclohexyl}-4,5-dihydro-1H-imidazole-4-carboxylic acid methyl ester;

4-butyl-1-cyclohexyl-5-{4-[dimethylamino-(3-fluorophenyl)-methyl]-cyclohexyl}-4,5-dihydro-1H-imidazole-4-carboxylic acid methyl ester;

5-{4-[(4-chlorophenyl)-dimethylaminomethyl]-cyclohexyl}-1-cyclohexyl-4-isobutyl-4,5-dihydro-1H-imidazole-4-carboxylic acid methyl ester;

4-(4-chlorobenzyl)-5-{4-[(4-chlorophenyl)-dimethylaminomethyl]-cyclohexyl}-1-cyclohexyl-4,5-dihydro-1H-imidazole-carboxylic acid methyl ester;

4-butyl-5-{4-[(4-chlorophenyl)-dimethylaminomethyl]-cyclohexyl}-1-cyclohexyl-4,5-dihydro-1H-imidazole-4-carboxylic carboxylic acid methyl ester;

5-{4-[(4-chlorophenyl)-dimethylaminomethyl]-cyclohexylmethyl}-1-cyclohexyl-4-isobutyl-4,5-dihydro-1H-imidazole-4-carboxylic acid methyl ester;

4-(4-chlorobenzyl)-5-{4-[(4-chlorophenyl)-dimethylaminomethyl]-cyclohexylmethyl}-1-cyclohexyl-4,5-dihydro-1H-imidazole-4-carboxylic acid methyl ester;

4-butyl-5-{4-[(4-chlorophenyl)-dimethylaminomethyl]-cyclohexylmethyl}-1-cyclohexyl-4,5-dihydro-1H-imidazole-4-carboxylic acid methyl ester;

4-(4-chlorobenzyl)-1-cyclohexyl-5-[4-(dimethylamino-thiophen-2-yl-methyl)-cyclohexylmethyl]-4,5-dihydro-1H-imidazole-4-carboxylic acid methyl ester;

5-{4-[dimethylamino-(3-fluorophenyl)-methyl]-cyclohexyl}-4-isobutyl-1-propyl-4,5-dihydro-1H-imidazole-4-carboxylic acid methyl ester;

4-(4-chlorobenzyl)-5-{4-[dimethylamino-(3-fluorophenyl)-methyl]-cyclohexyl}-1-propyl-4,5-dihydro-1H-imidazole-4-carboxylic acid methyl ester;

4-butyl-5-{4-[dimethylamino-(3-fluorophenyl)-methyl]-cyclohexyl}-1-propyl-4,5-dihydro-1H-imidazole-4-carboxylic acid methyl ester;

5-{4-[(4-chlorophenyl)-dimethylaminomethyl]-cyclohexyl}-4-isobutyl-1-propyl-4,5-dihydro-1H-imidazole-4-carboxylic acid methyl ester;

4-(4-chlorobenzyl)-5-{4-[(4-chlorophenyl)-dimethylaminomethyl]-cyclohexyl}-1-propyl-4,5-dihydro-1H-imidazole-4-carboxylic acid methyl ester;

5-(4-[(4-chlorophenyl)-dimethylaminomethyl)-cyclohexylmethyl]-4-isobutyl-1-propyl-4,5-dihydro-1H-imidazole-4-carboxylic acid methyl ester;

4-(4-chlorobenzyl)-5-{4-[(4-chlorophenyl)-dimethylaminomethyl]-cyclohexylmethyl}-1-propyl-4,5-dihydro-1H-imidazole-4-carboxylic acid methyl ester;

4-butyl-5-{4-[(4-chlorophenyl)-dimethylaminomethyl]-cyclohexylmethyl}-1-propyl-4,5-dihydro-1H-imidazole-4-carboxylic acid methyl ester;

1-butyl-5-{4-[dimethylamino-(3-fluorophenyl)-methyl]-cyclohexyl}-4-isobutyl-4,5-dihydro-1H-imidazole-4-carboxylic acid methyl ester;

1-butyl-4-(4-chlorobenzyl)-5-{4-[dimethylamino-(3-fluorophenyl)-methyl]-cyclohexyl}-4,5-dihydro-1H-imidazole-4-carboxylic acid methyl ester;

1-butyl-5-{4-[(chlorophenyl)-dimethylaminomethyl]-cyclohexyl}-4-isobutyl-4,5-dihydro-1H-imidazole-4-carboxylic acid methyl ester;

1-butyl-4-(4-chlorobenzyl)-5-{4-[(4-chlorophenyl)-dimethylaminomethyl]-cyclohexyl}-4,5-dihydro-1H-imidazole-4-carboxylic acid methyl ester;

1,4-dibutyl-5-{4-[(4-chlorophenyl)-dimethylaminomethyl]-cyclohexyl}-4,5-dihydro-1H-imidazole-4-carboxylic acid methyl ester;

1-butyl-5-{4-[(chlorophenyl)-dimethylaminomethyl]-cyclohexylmethyl}-4-isobutyl-4,5-dihydro-1H-imidazole-4-carboxylic acid methyl ester;

1-butyl-4-(4-chlorobenzyl)-5-{4-[(4-chlorophenyl)-dimethylaminomethyl]-cyclohexylmethyl}-4,5-dihydro-1H-imidazole-4-carboxylic acid methyl ester;

1,4-dibutyl-5-{4-[(4-chlorophenyl)-dimethylaminomethyl]-cyclohexylmethyl}-4,5-dihydro-1H-imidazole-4-carboxylic acid methyl ester;

5-{4-[dimethylamino-(3-fluorophenyl)-methyl]-cyclohexyl}-4-isobutyl-1-phenethyl-4,5-dihydro-1H-imidazole-4-carboxylic acid methyl ester;

4-(4-chlorobenzyl)-5-{4-[dimethylamino-(3-fluorophenyl)-methyl]-cyclohexyl}-1-phenethyl-4,5-dihydro-1H-imidazole-4-carboxylic acid methyl ester;

4-butyl-5-{4-[dimethylamino-(3-fluorophenyl)-methyl]-cyclohexyl}-1-phenethyl-4,5-dihydro-1H-imidazole-4-carboxylic acid methyl ester;

5-{4-[(4-chlorophenyl)-dimethylaminomethyl]-cyclohexyl}-4-isobutyl-1-phenethyl-4,5-dihydro-1H-imidazole-4-carboxylic acid methyl ester;

4-(4-chlorobenzyl)-5-{4-[(4-chlorophenyl)-dimethylaminomethyl]-cyclohexyl}-1-phenethyl-4,5-dihydro-1H-imidazole-4-carboxylic acid methyl ester;

4-butyl-5-{4-[(4-chlorophenyl)-dimethylaminomethyl]-cyclohexyl}-1-phenethyl-4,5-dihydro-1H-imidazole-4-carboxylic acid methyl ester;

5-{4-[(4-chlorophenyl)-dimethylaminomethyl]-cyclohexylmethyl}-4-isobutyl-1-phenethyl-4,5-dihydro-1H-imidazole-4-carboxylic acid methyl ester;

4-(4-chlorobenzyl)-5-{4-[(4-chlorophenyl)-dimethylaminomethyl]-cyclohexylmethyl}-1-phenethyl-4,5-dihydro-1H-imidazole-4-carboxylic acid methyl ester;

4-butyl-5-{4-[(4-chlorophenyl)-dimethylaminomethyl]-cyclohexylmethyl}-1-phenethyl-4,5-dihydro-1H-imidazole-4-carboxylic acid methyl ester;

1-benzyl-5-{4-[dimethylamino-(3-fluorophenyl)-methyl]-cyclohexyl}-4-isobutyl-4,5-dihydro-1H-imidazole-4-carboxylic acid methyl ester;

1-benzyl-4-(4-chlorobenzyl)-5-{4-[dimethylamino-(3-fluorophenyl)-methyl]-cyclohexyl}-4,5-dihydro-1H-imidazole-4-carboxylic acid methyl ester;

1-benzyl-5-{4-[(4-chlorophenyl)-dimethylaminomethyl]-cyclohexyl}-4-isobutyl-4,5-dihydro-1H-imidazole-4-carboxylic acid methyl ester;

1-benzyl-4-(4-chlorobenzyl)-5-{4-[(4-chlorophenyl)-dimethylaminomethyl]-cyclohexyl}-4,5-dihydro-1H-imidazole-4-carboxylic acid methyl ester;

1-benzyl-5-{4-[(4-chlorophenyl)-dimethylaminomethyl]-cyclohexylmethyl}-4-isobutyl-4,5-dihydro-1H-imidazole-4-carboxylic acid methyl ester;

5-{4-[(4-chlorophenyl)-dimethylaminomethyl]-cyclohexyl}-1-cyclohexyl-4-(2-methoxycarbonylethyl)-4,5-dihydro-1H-imidazole-4-carboxylic acid methyl ester;

4-benzylsulfanylmethyl-5-{4-[(4-chlorophenyl)-dimethylaminomethyl]-cyclohexyl}-1-cyclohexyl-4,5-dihydro-1H-imidazole-4-carboxylic acid methyl ester;

5-{4-[(4-chlorophenyl)-dimethylaminomethyl]-cyclohexylmethyl}-1-cyclohexyl-4-(2-methoxycarbonylethyl)-4,5-dihydro-1H-imidazole-4-carboxylic acid methyl ester;

1-benzyl-5-{4-[dimethylamino-(3-fluorophenyl)-methyl]-cyclohexylmethyl}-4-propyl-4,5-dihydro-1H-imidazole-4-carboxylic acid methyl ester;

5-{4-[(4-chlorophenyl)-dimethylaminomethyl]-cyclohexylmethyl}-1-cyclohexyl-4-methylsulfanylmethyl-4,5-dihydro-1H-imidazole-4-carboxylic acid methyl ester;

4-benzylsulfanylmethyl-5-{4-[(4-chlorophenyl)-dimethylaminomethyl]-cyclohexylmethyl}-1-cyclohexyl-4,5-dihydro-1H-imidazole-4-carboxylic acid methyl ester;

5-{4-[dimethylamino-(3-fluorophenyl)-methyl]-cyclohexyl}-4-methylsulfanylmethyl-1-propyl-4,5-dihydro-1H-imidazole-4-carboxylic acid methyl ester;

4-benzylsulfanylmethyl-5-{4-[dimethylamino-(3-fluorophenyl)-methyl]-cyclohexyl}-1-propyl-4,5-dihydro-1H-imidazole-4-carboxylic acid methyl ester;

5-{4-[(4-chlorophenyl)-dimethylaminomethyl]-cyclohexyl}-4-(2-methoxycarbonylethyl)-1-propyl-4,5-dihydro-1H-imidazole-4-carboxylic acid methyl ester;

4-benzylsulfanylmethyl-5-{4-[(4-chlorophenyl)-dimethylaminomethyl]-cyclohexyl}-1-propyl-4,5-dihydro-1H-imidazole-4-carboxylic acid methyl ester;

5-{4-[(4-chlorophenyl)-dimethylaminomethyl]-cyclohexylmethyl}-4-(2-methoxycarbonylethyl)-1-propyl-4,5-dihydro-1H-imidazole-4-carboxylic acid methyl ester;

4-sec-butyl-5-{4-[(4-chlorophenyl)-dimethylaminomethyl]-cyclohexylmethyl}-1-propyl-4,5-dihydro-1H-imidazole-4-carboxylic acid methyl ester;

5-{4-[(4-chlorophenyl)-dimethylaminomethyl]-cyclohexylmethyl}-4-methylsulfanylmethyl-1-propyl-4,5-dihydro-1H-imidazole-4-carboxylic acid methyl ester;

4-benzylsulfanylmethyl-5-{4-[(4-chlorophenyl)-dimethylaminomethyl]-cyclohexylmethyl}-1-propyl-4,5-dihydro-1H-imidazole-4-carboxylic acid methyl ester;

1-butyl-5-{4-[dimethylamino-(3-fluorophenyl)-methyl]-cyclohexyl}-4-(2-methoxycarbonylethyl)-4,5-dihydro-1H-imidazole-4-carboxylic acid methyl ester;

1-butyl-5-{4-[dimethylamino-(3-fluorophenyl)-methyl]-cyclohexyl}-4-methylsulfanylmethyl-4,5-dihydro-1H-imidazole-4-carboxylic acid methyl ester;

4-benzylsulfanylmethyl-1-butyl-5-{4-[dimethylamino-(3-fluorophenyl)-methyl]-cyclohexyl}-4,5-dihydro-1H-imidazole-4-carboxylic acid methyl ester;

1-butyl-5-{4-[(4-chlorophenyl)-dimethylaminomethyl]-cyclohexyl}-4-(2-methoxycarbonylethyl)-4,5-dihydro-1H-imidazole-4-carboxylic acid methyl ester;

4-benzylsulfanylmethyl-1-butyl-5-{4-[(4-chlorophenyl)-dimethylaminomethyl]-cyclohexyl}-4,5-dihydro-1H-imidazole-4-carboxylic acid methyl ester;

1-butyl-5-{4-[(4-chlorophenyl)-dimethylaminomethyl]-cyclohexylmethyl}-4-(2-methoxycarbonylethyl)-4,5-dihydro-1H-imidazole-4-carboxylic acid methyl ester;

5-[4-(1-dimethylamino-3-phenylpropyl)-cyclohexylmethyl]-4-(2-methoxycarbonylethyl)-1-propyl-4,5-dihydro-1H-imidazole-4-carboxylic acid methyl ester;

1-butyl-5-{4-[dimethylamino-(3-fluorophenyl)-methyl]-cyclohexylmethyl}-4-(2-methoxycarbonylethyl)-4,5-dihydro-1H-imidazole-4-carboxylic acid methyl ester;

1-butyl-4-sec-butyl-5-{4-[dimethylamino-(3-fluorophenyl)-methyl]-cyclohexylmethyl}-4,5-dihydro-1H-imidazole-4-carboxylic acid methyl ester;

1-butyl-5-{4-[dimethylamino-(3-fluorophenyl)-methyl]-cyclohexylmethyl}-4-methylsulfanylmethyl-4,5-dihydro-1H-imidazole-4-carboxylic acid methyl ester;

4-benzylsulfanylmethyl-1-butyl-5-{4-[dimethylamino-(3-fluorophenyl)-methyl]-cyclohexylmethyl}-4,5-dihydro-1H-imidazole-4-carboxylic acid methyl ester;

1-butyl-5-{4-[dimethylamino-(4-fluorophenyl)-methyl]-cyclohexylmethyl}-4-(2-methoxycarbonylethyl)-4,5-dihydro-1H-imidazole-4-carboxylic acid methyl ester;

1-butyl-5-{4-[dimethylamino-(4-fluorophenyl)-methyl]-cyclohexylmethyl}-4-methylsulfanylmethyl-4,5-dihydro-1H-imidazole-4-carboxylic acid methyl ester;

1-butyl-5-[4-(1-dimethylamino-3-phenylpropyl)-cyclohexylmethyl]-4-(2-methoxycarbonylethyl)-4,5-dihydro-1H-imidazole-4-carboxylic acid methyl ester;

4-benzylsulfanylmethyl-1-butyl-5-[4-(1-dimethylamino-3-phenylpropyl)-cyclohexylmethyl]-4,5-dihydro-1H-imidazole-4-carboxylic acid methyl ester;

5-{4-[dimethylamino-(3-fluorophenyl)-methyl]-cyclohexylmethyl}-4-(2-methoxycarbonylethyl)-1-phenethyl-4,5-dihydro-1H-imidazole-4-carboxylic acid methyl ester;

4-sec-butyl-5-{4-[dimethylamino-(3-fluorophenyl)-methyl]-cyclohexylmethyl}-1-phenethyl-4,5-dihydro-1H-imidazole-4-carboxylic acid methyl ester;

4-benzylsulfanylmethyl-5-{4-[dimethylamino-(3-fluorophenyl)-methyl]-cyclohexylmethyl}-1-phenethyl-4,5-dihydro-1H-imidazole-4-carboxylic acid methyl ester;

5-{4-[dimethylamino-(4-fluorophenyl)-methyl]-cyclohexylmethyl}-4-(2-methoxycarbonylethyl)-1-phenethyl-4,5-dihydro-1H-imidazole-4-carboxylic acid methyl ester;

5-[4-(1-dimethylamino-3-phenylpropyl)-cyclohexylmethyl]-4-(2-methoxycarbonylethyl)-1-phenethyl-4,5-dihydro-1H-imidazole-4-carboxylic acid methyl ester;

1-benzyl-5-{4-[dimethylamino-(3-fluorophenyl)-methyl]-cyclohexylmethyl}-4-(2-methoxycarbonylethyl)-4,5-dihydro-1H-imidazole-4-carboxylic acid methyl ester;

1-benzyl-4-benzylsulfanylmethyl-5-{4-[dimethylamino-(3-fluorophenyl)-methyl]-cyclohexylmethyl}-4,5-dihydro-1H-imidazole-4-carboxylic acid methyl ester;

1-benzyl-5-{4-[dimethylamino-(4-fluorophenyl)-methyl]-cyclohexylmethyl}-4-(2-methoxycarbonylethyl)-4,5-dihydro-1H-imidazole-carboxylic acid methyl ester 1-butyl-4-sec-butyl-5-{4-[(4-chlorophenyl)-dimethylaminomethyl]-cyclohexylmethyl}-4,5-dihydro-1H-imidazole-4-carboxylic acid methyl ester;

1-butyl-5-{4-[(4-chlorophenyl)-dimethylaminomethyl]-cyclohexylmethyl}-4-methylsulfanylmethyl-4,5-dihydro-1H-imidazole-4-carboxylic acid methyl ester;

4-benzylsulfanylmethyl-1-butyl-5-{4-[(4-chlorophenyl)-dimethylaminomethyl]-cyclohexylmethyl}-4,5-dihydro-1H-imidazole-4-carboxylic acid methyl ester;

5-{4-[dimethylamino-(3-fluorophenyl)-methyl]-cyclohexyl}-4-(2-methoxycarbonylethyl)-1-phenethyl-4,5-dihydro-1H-imidazole-4-carboxylic acid methyl ester;

4-benzylsulfanylmethyl-5-{4-[dimethylamino-(3-fluorophenyl)-methyl]-cyclohexyl}-1-phenethyl-4,5-dihydro-1H-imidazole-4-carboxylic acid methyl ester;

4-benzylsulfanylmethyl-5-{4-[(4-chlorophenyl)-dimethylaminomethyl]-cyclohexyl}-1-phenethyl-4,5-dihydro-1H-imidazole-4-carboxylic acid methyl ester;

5-{4-[(4-chlorophenyl)-dimethylaminomethyl]-cyclohexylmethyl}-4-(2-methoxycarbonylethyl)-1-phenethyl-4,5-dihydro-1H-imidazole-4-carboxylic acid methyl ester;

1-benzyl-5-{4-[dimethylamino-(3-fluorophenyl)-methyl]-cyclohexyl}-4-(2-methoxycarbonylethyl)-4,5-dihydro-1H-imidazole-4-carboxylic acid methyl ester;

1-benzyl-5-{4-[dimethylamino-(3-fluorophenyl)-methyl]-cyclohexyl-4-methylsulfanylmethyl-4,5-dihydro-1H-imidazole-4-carboxylic acid methyl ester;

1-benzyl-4-benzylsulfanylmethyl-5-{4-[dimethylamino-(3-fluorophenyl)-methyl]-cyclohexyl}-4,5-dihydro-1H-imidazole-4-carboxylic acid methyl ester;

1-benzyl-4-benzylsulfanylmethyl-5-{4-[(4-chlorophenyl)-dimethylaminomethyl]-cyclohexyl}-4,5-dihydro-1H-imidazole-4-carboxylic acid methyl ester;

1-benzyl-5-{4-[(4-chlorophenyl)-dimethylaminomethyl]-cyclohexylmethyl}-4-(2-methoxycarbonylethyl)-4,5-dihydro-1H-imidazole-4-carboxylic acid methyl ester;

1-benzyl-5-{4-[(4-chlorophenyl)-dimethylaminomethyl]-cyclohexylmethyl}-4-methylsulfanylmethyl-4,5-dihydro-1H-imidazole-4-carboxylic acid methyl ester;

1-benzyl-4-benzylsulfanylmethyl-5-{4-[(4-chlorophenyl)-dimethylaminomethyl]-cyclohexylmethyl}-4,5-dihydro-1H-imidazole-4-carboxylic acid methyl ester;

1-cyclohexyl-5-{4-[dimethylamino-(3-fluorophenyl)-methyl]-cyclohexylmethyl}-4-propyl-4,5-dihydro-1H-imidazole-4-carboxylic acid methyl ester;

1-cyclohexyl-5-{4-[dimethylamino-(3-fluorophenyl)-methyl]-cyclohexylmethyl}-4-(2-methylsulfanylethyl)-4,5-dihydro-1H-imidazole-4-carboxylic acid methyl ester;

1-cyclohexyl-5-{4-[dimethylamino-(3-fluorophenyl)-methyl]-cyclohexylmethyl}-4-methyl-4,5-dihydro-1H-imidazole-4-carboxylic acid methyl ester;

1-cyclohexyl-5-{4-[dimethylamino-(4-fluorophenyl)-methyl]-cyclohexylmethyl}-4-propyl-4,5-dihydro-1H-imidazole-4-carboxylic acid methyl ester;

1-cyclohexyl-5-{4-[dimethylamino-(4-fluorophenyl)-methyl]-cyclohexylmethyl}-4-(2-methylsulfanylethyl)-4,5-dihydro-1H-imidazole-4-carboxylic acid methyl ester;

1-cyclohexyl-5-{4-[dimethylamino-(4-fluorophenyl)-methyl]-cyclohexylmethyl}-4-methyl-4,5-dihydro-1H-imidazole-4-carboxylic acid methyl ester;

1-cyclohexyl-5-[4-(1-dimethylamino-3-phenylpropyl)-cyclohexylmethyl]-4-propyl-4,5-dihydro-1H-imidazole-4-carboxylic acid methyl ester;

1-cyclohexyl-5-[4-(1-dimethylamino-3-phenylpropyl)-cyclohexylmethyl]-4-(2-methylsulfanylethyl)-4,5-dihydro-1H-imidazole-4-carboxylic acid methyl ester;

1-cyclohexyl-5-[4-(1-dimethylamino-3-phenylpropyl)-cyclohexylmethyl]-4-methyl-4,5-dihydro-1H-imidazole-4-carboxylic acid methyl ester;

5-{4-[dimethylamino-(3-fluorophenyl)-methyl]-cyclohexylmethyl}-1,4-dipropyl-4,5-dihydro-1H-imidazole-4-carboxylic acid methyl ester;

5-{4-[dimethylamino-(3-fluorophenyl)-methyl]-cyclohexylmethyl}-4-(2-methylsulfanylethyl)-1-propyl-4,5-dihydro-1H-imidazole-4-carboxylic acid methyl ester;

1-benzyl-4-(4-chlorobenzyl)-5-{4-[(4-chlorophenyl)-dimethylaminomethyl]-cyclohexylmethyl}-4,5-dihydro-1H-imidazole-4-carboxylic acid methyl ester;

1-benzyl-4-butyl-5-{4-[(chlorophenyl)-dimethylaminomethyl]-cyclohexylmethyl}-4,5-dihydro-1H-imidazole-4-carboxylic acid methyl ester;

1-cyclohexyl-5-{4-[dimethylamino-(3-fluorophenyl)-methyl]-cyclohexyl}-4-(2-methoxycarbonylethyl)-4,5-dihydro-1H-imidazole-4-carboxylic acid methyl ester;

4-benzylsulfanylmethyl-1-cyclohexyl-5-{4-[dimethylamino-(3-fluorophenyl)-methyl]-cyclohexyl}-4,5-dihydro-1H-imidazole-4-carboxylic acid methyl ester;

5-{4-[dimethylamino-(3-fluorophenyl)-methyl]-cyclohexylmethyl}-4-methyl-1-propyl-4,5-dihydro-1H-imidazole-4-carboxylic acid methyl ester;

5-{4-[dimethylamino-(4-fluorophenyl)-methyl]-cyclohexylmethyl}-1,4-dipropyl-4,5-dihydro-1H-imidazole-4-carboxylic acid methyl ester;

5-{4-[dimethylamino-(4-fluorophenyl)-methyl]-cyclohexylmethyl}-4-(2-methylsulfanylethyl)-1-propyl-4,5-dihydro-1H-imidazole-4-carboxylic acid methyl ester;

5-[4-(1-dimethylamino-3-phenylpropyl)-cyclohexylmethyl]-1,4-dipropyl-4,5-dihydro-1H-imidazole-4-carboxylic acid methyl ester;

5-[4-(1-dimethylamino-3-phenylpropyl)-cyclohexylmethyl]-4-(2-methylsulfanylethyl)-1-propyl-4,5-dihydro-1H-imidazole-4-carboxylic acid methyl ester;

1-butyl-5-{4-[dimethylamino-(3-fluorophenyl)-methyl]-cyclohexylmethyl}-4-propyl-4,5-dihydro-1H-imidazole-4-carboxylic acid methyl ester;

1-butyl-5-{4-[dimethylamino-(3-fluorophenyl)-methyl]-cyclohexylmethyl}-4-(2-methylsulfanylethyl)-4,5-dihydro-1H-imidazole-4-carboxylic acid methyl ester;

1-butyl-5-{4-[dimethylamino-(3-fluorophenyl)-methyl]-cyclohexylmethyl}-4-methyl-4,5-dihydro-1H-imidazole-4-carboxylic acid methyl ester;

1-butyl-5-{4-[dimethylamino-(4-fluorophenyl)-methyl]-cyclohexylmethyl}-4-propyl-4,5-dihydro-1H-imidazole-4-carboxylic acid methyl ester;

1-butyl-5-{4-[dimethylamino-(4-fluorophenyl)-methyl]-cyclohexylmethyl}-4-(2-methylsulfanylethyl)-4,5-dihydro-1H-imidazole-4-carboxylic acid methyl ester;

1-butyl-5-[4-(1-dimethylamino-3-phenylpropyl)-cyclohexylmethyl]-4-propyl-4,5-dihydro-1H-imidazole-4-carboxylic acid methyl ester;

1-butyl-5-[4-(1-dimethylamino-3-phenylpropyl)-cyclohexylmethyl]-4-(2-methylsulfanylethyl)-4,5-dihydro-1H-imidazole-4-carboxylic acid methyl ester;

5-{4-[dimethylamino-(3-fluorophenyl)-methyl]-cyclohexylmethyl}-1-phenethyl-4-propyl-4,5-dihydro-1H-imidazole-4-carboxylic acid methyl ester;

5-{4-[dimethylamino-(3-fluorophenyl)-methyl]-cyclohexylmethyl}-4-(2-methylsulfanylethyl)-1-phenethyl-4,5-dihydro-1H-imidazole-4-carboxylic acid methyl ester;

5-{4-[dimethylamino-(3-fluorophenyl)-methyl]-cyclohexylmethyl}-4-methyl-1-phenethyl-4,5-dihydro-1H-imidazole-4-carboxylic acid methyl ester;

5-{4-[dimethylamino-(4-fluorophenyl)-methyl]-cyclohexylmethyl}-1-phenethyl-4-propyl-4,5-dihydro-1H-imidazole-4-carboxylic acid methyl ester;

5-{4-[dimethylamino-(4-fluorophenyl)-methyl]-cyclohexylmethyl}-4-(2-methylsulfanylethyl)-1-phenethyl-4,5-dihydro-1H-imidazole-4-carboxylic acid methyl ester;

5-{4-[dimethylamino-(4-fluorophenyl)-methyl]-cyclohexylmethyl}-4-methyl-1-phenethyl-4,5-dihydro-1H-imidazole-4-carboxylic acid methyl ester;

5-[4-(1-dimethylamino-3-phenylpropyl)-cyclohexylmethyl]-1-phenethyl-4-propyl-4,5-dihydro-1H-imidazole-4-carboxylic acid methyl ester;

5-[4-(1-dimethylamino-3-phenylpropyl)-cyclohexylmethyl]-4-(2-methylsulfanylethyl)-1-phenethyl-4,5-dihydro-1H-imidazole-4-carboxylic acid methyl ester;

5-[4-(1-dimethylamino-3-phenylpropyl)-cyclohexylmethyl]-4-methyl-1-phenethyl-4,5-dihydro-1H-imidazole-4-carboxylic acid methyl ester;

1-benzyl-5-{4-[dimethylamino-(3-fluorophenyl)-methyl]-cyclohexylmethyl}-4-propyl-4,5-dihydro-1H-imidazole-4-carboxylic acid methyl ester;

1-benzyl-5-{4-[dimethylamino-(3-fluorophenyl)-methyl]-cyclohexylmethyl}-4-(2-methylsulfanylethyl)-4,5-dihydro-1H-imidazole-4-carboxylic acid methyl ester;

1-benzyl-5-{4-[dimethylamino-(3-fluorophenyl)-methyl]-cyclohexylmethyl}-4-methyl-4,5-dihydro-1H-imidazole-4-carboxylic acid methyl ester;

1-benzyl-5-{4-[dimethylamino-(4-fluorophenyl)-methyl]-cyclohexylmethyl}-4-propyl-4,5-dihydro-1H-imidazole-4-carboxylic acid methyl ester;

1-benzyl-5-{4-[dimethylamino-(4-fluorophenyl)-methyl]-cyclohexylmethyl}-4-(2-methylsulfanylethyl)-4,5-dihydro-1H-imidazole-4-carboxylic acid methyl ester;

1-benzyl-5-{4-[dimethylamino-(4-fluorophenyl)-methyl]-cyclohexylmethyl}-4-methyl-4,5-dihydro-1H-imidazole-4-carboxylic acid methyl ester;

1-benzyl-5-[4-(1-dimethylamino-3-phenylpropyl)-cyclohexylmethyl]-4-propyl-4,5-dihydro-1H-imidazole-4-carboxylic acid methyl ester;

1-benzyl-5-[4-(1-dimethylamino-3-phenylpropyl)-cyclohexylmethyl]-4-(2-methylsulfanylethyl)-4,5-dihydro-1H-imidazole-4-carboxylic acid methyl ester;

1-benzyl-5-[4-(1-dimethylamino-3-phenylpropyl)-cyclohexylmethyl]-4-methyl-4,5-dihydro-1H-imidazole-4-carboxylic acid methyl ester;

1-cyclohexyl-5-{4-[dimethylamino-(3-fluorophenyl)-methyl]-cyclohexylmethyl}-4-(2-methoxycarbonylethyl)-4,5-dihydro-1H-imidazole-4-carboxylic acid methyl ester;

4-sec-butyl-1-cyclohexyl-5-{4-[dimethylamino-(3-fluorophenyl)-methyl]-cyclohexylmethyl}-4,5-dihydro-1H-imidazole-4-carboxylic acid methyl ester;

1-cyclohexyl-5-{4-[dimethylamino-(3-fluorophenyl)-methyl]-cyclohexylmethyl}-4-methylsulfanylmethyl-4,5-dihydro-1H-imidazole-4-carboxylic acid methyl ester;

4-benzylsulfanylmethyl-1-cyclohexyl-5-{4-[dimethylamino-(3-fluorophenyl)-methyl]-cyclohexylmethyl}-4,5-dihydro-1H-imidazole-4-carboxylic acid methyl ester;

1-cyclohexyl-5-{4-[dimethylamino-(4-fluorophenyl)-methyl]-cyclohexylmethyl}-4-(2-methoxycarbonylethyl)-4,5-dihydro-1H-imidazole-4-carboxylic acid methyl ester;

4-sec-butyl-1-cyclohexyl-5-{4-[dimethylamino-(4-fluorophenyl)-methyl]-cyclohexylmethyl}-4,5-dihydro-1H-imidazole-4-carboxylic acid methyl ester;

1-cyclohexyl-5-{4-[dimethylamino-(4-fluorophenyl)-methyl]-cyclohexylmethyl}-4-methylsulfanylmethyl-4,5-dihydro-1H-imidazole-4-carboxylic acid methyl ester;

1-cyclohexyl-5-[4-(1-dimethylamino-3-phenylpropyl)-cyclohexylmethyl]-4-(2-methoxycarbonylethyl)-4,5-dihydro-1H-imidazole-4-carboxylic acid methyl ester;

1-cyclohexyl-5-[4-(1-dimethylamino-3-phenylpropyl)-cyclohexylmethyl]-4-methylsulfanylmethyl-4,5-dihydro-1H-imidazole-4-carboxylic acid methyl ester;

4-benzylsulfanylmethyl-1-cyclohexyl-5-[4-(1-dimethylamino-3-phenylpropyl)-cyclohexylmethyl]-4,5-dihydro-1H-imidazole-4-carboxylic acid methyl ester;

5-{4-[dimethylamino-(3-fluorophenyl)-methyl]-cyclohexylmethyl}-4-(2-methoxycarbonylethyl)-1-propyl-4,5-dihydro-1H-imidazole-4-carboxylic acid methyl ester;

5-{4-[dimethylamino-(3-fluorophenyl)-methyl]-cyclohexylmethyl}-4-methylsulfanylmethyl-1-propyl-4,5-dihydro-1H-imidazole-4-carboxylic acid methyl ester;

5-{4-[dimethylamino-(4-fluorophenyl)-methyl]-cyclohexylmethyl}-4-(2-methoxycarbonylethyl)-1-propyl-4,5-dihydro-1H-imidazole-4-carboxylic acid methyl ester;

5-{4-[dimethylamino-(4-fluorophenyl)-methyl]-cyclohexylmethyl}-4-methylsulfanylmethyl-1-propyl-4,5-dihydro-1H-imidazole-4-carboxylic acid methyl ester;

4-benzylsulfanylmethyl-5-{4-[dimethylamino-(4-fluorophenyl)-methyl]-cyclohexylmethyl}-1-propyl-4,5-dihydro-1H-imidazole-4-carboxylic acid methyl ester; and methyl-4-sec-butyl-5-((4-(4-chlorophenyl)(dimethylamino) methyl)cyclohexyl)-methyl)-1-cyclohexyl-4,5-dihydro-1H-imidazole-4-carboxylate.

The foregoing preferred compounds and other compounds of the invention may be present in the form of a racemate; in the form of the enantiomers, diastereomers, mixtures of the enantiomers or diastereomers; in the form of an individual enantiomer or diastereomer; in the form of the free bases, or in the form of salts of physiologically compatible acids.

The invention also provides a process for the preparation of an imidazoline derivative according to the invention. In this connection the keto function of 4-oxocyclohexanecarboxylic acid esters

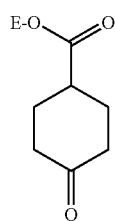

wherein E denotes a $C_{1-6}$-alkyl radical, preferably ethyl, is protected by methods known to the person skilled in the art

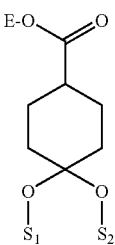

4

Here S1 and S2 denote in each case a protective group, preferably form a ring, and together denote —$CH_2$—$CH_2$—. The ester 4 is reduced with a reducing agent, for example diisobutyl aluminium hydride, to form the aldehyde 5

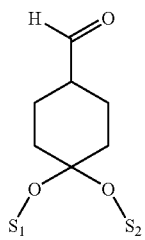

5

By adding an amine of the general Formula $R^5R^6NH$ and a cyanide, for example KCN or NaCN, the aldehyde 5 is converted under the addition of an acid, for example hydrochloric acid, in an organic solvent, for example methanol or ethanol, to the nitrile 6.

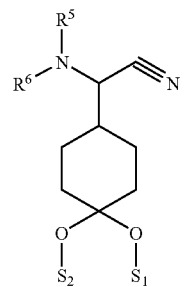

6

The nitrile 6 is reacted with a Grignard reagent of the general formula $R^2MgHal$, wherein Hal denotes Br, Cl or I, or an organometallic compound of the general formula $R^2Li$ in an organic solvent, for example diethyl ether, dioxane or tetrahydrofuran, to form a compound of the general Formula 7

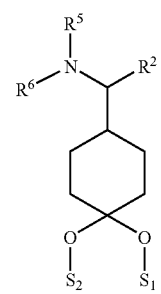

7

The protective groups are removed by conventional methods to obtain the ketone 8.

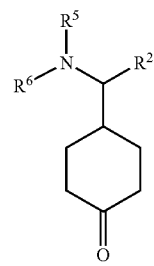

8

The aldehyde 9

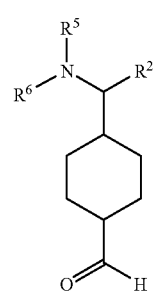

9 is obtained by reacting the ketone 8 with (methoxymethyl) triphenylphosphonium chloride and a strong base, for example potassium tert-butylate, at a temperature from −20° C. to +30° C. By reacting the aldehyde 9 with (methoxymethyl)triphenyl-phosphonium chloride and a strong base, for example potassium tert-butylate at a temperature from −20° C. to +30° C., an aldehyde of Formula 10 is obtained.

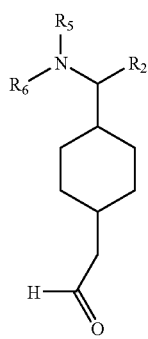

By repeating the last reaction step aldehydes can be obtained in which n is 2.

The aldehydes of the general Formula B are reacted with amines of the general Formula A and isonitrile esters of the general Formula C in an organic solvent, for example methanol or ethanol, at a temperature of 20°-100° C. according to the following synthesis reaction scheme, to form substituted imidazoline derivatives of the general Formula I

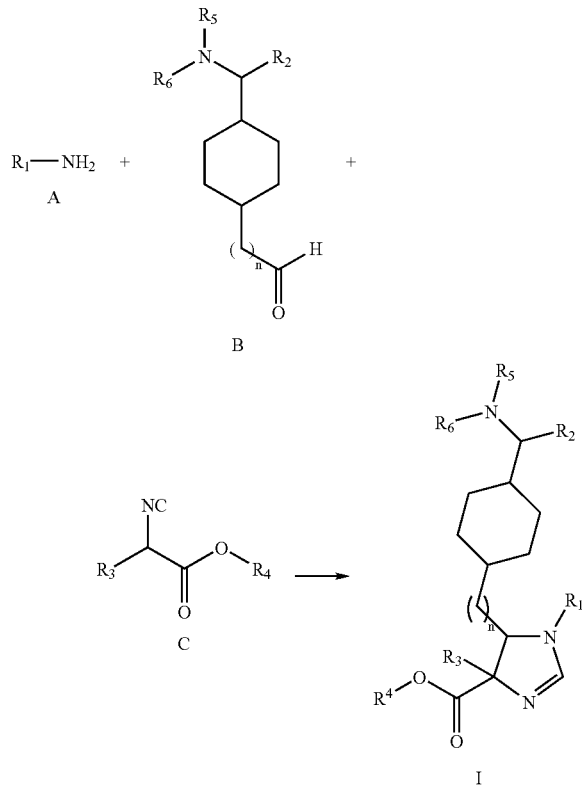

The amines of the general Formula A are commercially obtainable or can be prepared by methods known to the person skilled in the art. The isonitrile esters of the general Formula C are either commercially obtainable or can be prepared according to the method of R. S. Bon et al., Org. Lett. 2003, 5, 20, 3759-3762.

Diastereomers and/or enantiomers can be separated by methods known to the person skilled in the art, for example by recrystallisation, chromatography or in particular HPLC chromatography, or crystallisation with an optionally chiral acid or base and separation of the salts or chiral HPLC chromatography (Fogassy et al., Optical resolution methods, Org. Biomol. Chem. 2006, 4, 3011-3030).

In the case of compounds in which $R^4$ denotes $C_{1-4}$-alkyl or an aryl radical bonded via a $C_{1-3}$-alkyl chain, $R^4$ can be split off according to the following method:

The ester is dissolved or suspended in a small amount of dioxane or THF and is heated under reflux with 1 N sodium hydroxide or potassium hydroxide (10 ml/g) until it has completely dissolved. For working-up, the reaction mixture is first of all concentrated by evaporation to dryness, following which sufficient water is added so that the residue just dissolves. The solution is carefully acidified with concentrated HCl (pH1) and the acid is extracted several times with diethyl ether or dichloromethane. The combined organic phases are washed with a small amount of saturated sodium chloride solution, dried, and concentrated by evaporation.

The aldehydes of Formula B are new and surprisingly exhibit a good binding to the μ-opioid receptor as well as an inhibition of noradrenaline and also serotonin reuptake. The invention therefore also provides an aldehyde of Formula B

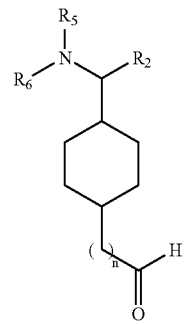

wherein the radicals $R^2$, $R^5$, $R^6$ as well as n have the meanings given above.

Preferred are aldehydes of Formula B according to the invention selected from the following group:

4-[dimethylamino-(4-fluorophenyl)-methyl]-cyclohexanecarbaldehyde;

4-(1-dimethylamino-3-phenylpropyl)-cyclohexanecarbaldehyde;

4-[dimethylamino-(3-fluorophenyl)-methyl]-cyclohexanecarbaldehyde;

4-[(4-chlorophenyl)-dimethylaminomethyl]-cyclohexanecarbaldehyde;

{4-[(4-chlorophenyl)-dimethylaminomethyl]-cyclohexyl}-acetaldehyde;

{4-[dimethylamino-(3-fluorophenyl)-methyl]-cyclohexyl}-acetaldehyde;

4-(dimethylamino-thiophen-2-yl-methyl)-cyclohexanecarbaldehyde;

{4-[dimethylamino-(4-fluorophenyl)-methyl]-cyclohexyl}-acetaldehyde;

[4-(dimethylamino-thiophen-2-yl-methyl)-cyclohexyl]-acetaldehyde; and

[4-(1-dimethylamino-3-phenylpropyl)-cyclohexyl]-acetaldehyde.

The preferred aldehydes listed above and other aldehydes according to the invention may be present in the form of the racemates; in the form of enantiomers, diastereomers, mixtures of the enantiomers or diastereomers; in the form of an individual enantiomer or diastereomer; in the form of a free base; or in the form of salts of physiologically compatible acids.

The substances according to the invention are suitable as pharmaceutical active substances in medicaments. The invention accordingly also provides medicaments containing at least one substituted imidazoline derivative according to the invention of the general Formula I and a substituted aldehyde of the invention of the general Formula B, as well as optionally suitable additives and/or auxiliary substances and/or optionally further active substances.

The medicaments according to the invention contain, apart from at least one substituted imidazoline derivative according to the invention or a substituted aldehyde according to the invention, optionally also suitable additives and/or auxiliary substances, thus also carrier materials, fillers, solvents, diluents, colorants and/or binders, and can be administered as liquid medicament in the form of injection solutions, drops or juices, as semi-solid medicament in the form of granules, tablets, pellets, patches, capsules, plasters or aerosols. The choice of the auxiliary substances, etc. as well as the amounts thereof to be employed depends on whether the medicament is to be administered orally, parenterally, intravenously, intraperitoneally, intradermally, intramuscularly, intranasally, buccally, rectally or topically, for example to the skin, mucus membranes or to the eyes. For oral application suitable preparations are in the form of tablets, pills, capsules, granules, drops, juices and syrups, while for parenteral, topical and inhalative application suitable preparations are solutions, suspensions, easily reconstitutable dry preparations as well as sprays. Imidazoline derivatives according to the invention in a depot form, in dissolved form or in a plaster, optionally with the addition of agents promoting penetration of the skin, are suitable percutaneous application forms. Orally or percutaneously employable preparation forms can release the imidazoline derivatives or aldehydes according to the invention in a delayed manner. In principle other active substances known to the person skilled in the art can also be added to the medicaments according to the invention.

The amount of active substance to be administered to the patient varies depending on the patient's weight, type of application, medical indications and the severity of the disease. Normally 0.005 to 20 mg/kg, preferably 0.05 to 5 mg/kg of at least one imidazoline derivative or aldehyde according to the invention are administered.

In the medicament a contained imidazoline derivative according to the invention or contained aldehyde according to the invention can be present as pure diastereomer and/or enantiomer, as racemate, or as a non-equimolar or equimolar mixture of the diastereomers and/or enantiomers.

The invention also provides for the use of an imidazoline derivative or substituted aldehyde according to the invention for the preparation of a medicament for treating pain, in particular acute, neuropathic or chronic pain.

The invention also provides for the use of an imidazoline derivative or substituted aldehyde according to the invention for treatment of or the preparation of a medicament for treating depression and/or anxiety.

The substituted imidazoline derivatives or substituted aldehydes of Formula I and of the general Formula B are also suitable for treating urinary incontinence, diarrhea, pruritus, alcohol and drug misuse, drug dependency and lack of drive.

The invention therefore also provides for the use of a substituted imidazoline derivative of the general formula I and of a substituted aldehyde of the general formula B for the treatment of or the preparation of a medicament for treating urinary incontinence, diarrhea, pruritus, alcohol and drug misuse, drug dependency and lack of drive.

Particularly preferably the substituted imidazoline derivatives or substituted aldehydes according to the invention that are used for the treatment of pain or the preparation of a medicament for treating pain, in particular acute, neuropathic or chronic pain, depression and/or anxiety, for treating urinary incontinence, diarrhea, pruritus, alcohol and drug misuse, drug dependency and lack of drive, are selected from the following group:

4-[dimethylamino-(4-fluorophenyl)-methyl]-cyclohexanecarbaldehyde;

4-(1-dimethylamino-3-phenylpropyl)-cyclohexanecarbaldehyde;

4-[dimethylamino-(3-fluorophenyl)-methyl]-cyclohexanecarbaldehyde;

4-[(4-chlorophenyl)-dimethylaminomethyl]-cyclohexanecarbaldehyde;

{4-[(4-chlorophenyl)-dimethylaminomethyl]-cyclohexyl}-acetaldehyde;

{4-[dimethylamino-(3-fluorophenyl)-methyl]-cyclohexyl}-acetaldehyde;

4-(dimethylaminothiophen-2-yl-methyl)-cyclohexanecarbaldehyde;

{4-[dimethylamino-(4-fluorophenyl)-methyl]-cyclohexyl}-acetaldehyde;

[4-(dimethylaminothiophen-2-yl-methyl)-cyclohexyl]-acetaldehyde;

[4-(1-dimethylamino-3-phenylpropyl)-cyclohexyl]-acetaldehyde;

1-cyclohexyl-5-{4-[dimethylamino-(3-fluorophenyl)-methyl]-cyclohexyl}-4-isobutyl-4,5-dihydro-1H-imidazole-4-carboxylic acid methyl ester;

4-(4-chlorobenzyl)-1-cyclohexyl-5-{4-[dimethylamino-(3-fluorophenyl)-methyl]-cyclohexyl}-4,5-dihydro-1H-imidazole-4-carboxylic acid methyl ester;

4-butyl-1-cyclohexyl-5-{4-[dimethylamino-(3-fluorophenyl)-methyl]-cyclohexyl}-4,5-dihydro-1H-imidazole-4-carboxylic acid methyl ester;

5-{4-[(4-chlorophenyl)-dimethylaminomethyl]-cyclohexyl}-1-cyclohexyl-4-isobutyl-4,5-dihydro-1H-imidazole-4-carboxylic acid methyl ester;

4-(4-chlorobenzyl)-5-{4-[(4-chlorophenyl)-dimethylaminomethyl]-cyclohexyl}-1-cyclohexyl-4,5-dihydro-1H-imidazole-4-carboxylic acid methyl ester;

4-butyl-5-{4-[(4-chlorophenyl)-dimethylaminomethyl]-cyclohexyl}-1-cyclohexyl-4,5-dihydro-1H-imidazole-4-carboxylic acid methyl ester;

5-{4-[(4-chlorophenyl)-dimethylaminomethyl]-cyclohexylmethyl}-1-cyclohexyl-4-isobutyl-4,5-dihydro-1H-imidazole-4-carboxylic acid methyl ester;

4-(4-chlorobenzyl)-5-{4-[(4-chlorophenyl)-dimethylaminomethyl]-cyclohexylmethyl}-1-cyclohexyl-4,5-dihydro-1H-imidazole-4-carboxylic acid methyl ester;

4-butyl-5-{4-[(4-chlorophenyl)-dimethylaminomethyl]-cyclohexylmethyl}-1-cyclohexyl-4,5-dihydro-1H-imidazole-4-carboxylic acid methyl ester;

4-(4-chlorobenzyl)-1-cyclohexyl-5-[4-(dimethylaminothiophen-2-yl-methyl)-cyclohexylmethyl]-4,5-dihydro-1H-imidazole-4-carboxylic acid methyl ester;

5-{4-[dimethylamino-(3-fluorophenyl)-methyl]-cyclohexyl}-4-isobutyl-1-propyl-4,5-dihydro-1H-imidazole-4-carboxylic acid methyl ester;

4-(4-chlorobenzyl)-5-{4-[dimethylamino-(3-fluorophenyl)-methyl]-cyclohexyl}-1-propyl-4,5-dihydro-1H-imidazole-4-carboxylic acid methyl ester;

4-butyl-5-{4-[dimethylamino-(3-fluorophenyl)-methyl]-cyclohexyl}-1-propyl-4,5-dihydro-1H-imidazole-4-carboxylic acid methyl ester;

5-{4-[(4-chlorophenyl)-dimethylaminomethyl]-cyclohexyl}-4-isobutyl-1-propyl-4,5-dihydro-1H-imidazole-4-carboxylic acid methyl ester;

4-(4-chlorobenzyl)-5-{4-[(4-chlorophenyl)-dimethylaminomethyl]-cyclohexyl}-1-propyl-4,5-dihydro-1H-imidazole-4-carboxylic acid methyl ester;

5-{4-[(4-chlorophenyl)-dimethylaminomethyl]-cyclohexylmethyl}-4-isobutyl-1-propyl-4,5-dihydro-1H-imidazole-4-carboxylic acid methyl ester;

4-(4-chlorobenzyl)-5-{4-[(4-chlorophenyl)-dimethylaminomethyl]-cyclohexylmethyl}-1-propyl-4,5-dihydro-1H-imidazole-4-carboxylic acid methyl ester;

4-butyl-5-{4-[(4-chlorophenyl)-dimethylaminomethyl]-cyclohexylmethyl}-1-propyl-4,5-dihydro-1H-imidazole-4-carboxylic acid methyl ester;

1-butyl-5-{4-[dimethylamino-(3-fluorophenyl)-methyl]-cyclohexyl}-4-isobutyl-4,5-dihydro-1H-imidazole-4-carboxylic acid methyl ester;

1-butyl-4-(4-chlorobenzyl)-5-{4-[dimethylamino-(3-fluorophenyl)-methyl]-cyclohexyl}-4,5-dihydro-1H-imidazole-4-carboxylic acid methyl ester;

1-butyl-5-{4-[(4-chlorophenyl)-dimethylaminomethyl]-cyclohexyl}-4-isobutyl-4,5-dihydro-1H-imidazole-4-carboxylic acid methyl ester;

1-butyl-4-(4-chlorobenzyl)-5-{4-[(4-chlorophenyl)-dimethylaminomethyl]-cyclohexyl}-4,5-dihydro-1H-imidazole-4-carboxylic acid methyl ester;

1,4-dibutyl-5-{4-[(4-chlorophenyl)-dimethylaminomethyl]-cyclohexyl}-4,5-dihydro-1H-imidazole-4-carboxylic acid methyl ester;

1-butyl-5-{4-[(4-chlorophenyl)-dimethylaminomethyl]-cyclohexylmethyl}-4-isobutyl-4,5-dihydro-1H-imidazole-4-carboxylic acid methyl ester;

1-butyl-4-(4-chlorobenzyl)-5-{4-[(4-chlorophenyl)-dimethylaminomethyl]-cyclohexylmethyl}-4,5-dihydro-1H-imidazole-4-carboxylic acid methyl ester;

1,4-dibutyl-5-{4-[(4-chlorophenyl)-dimethylaminomethyl]-cyclohexylmethyl}-4,5-dihydro-1H-imidazole-4-carboxylic acid methyl ester;

5-{4-[dimethylamino-(3-fluorophenyl)-methyl]-cyclohexyl}-4-isobutyl-1-phenethyl-4,5-dihydro-1H-imidazole-4-carboxylic acid methyl ester;

4-(4-chlorobenzyl)-5-{4-[dimethylamino-(3-fluorophenyl)-methyl]-cyclohexyl}-1-phenethyl-4,5-dihydro-1H-imidazole-4-carboxylic acid methyl ester;

4-butyl-5-{4-[dimethylamino-(3-fluorophenyl)-methyl]-cyclohexyl}-1-phenethyl-4,5-dihydro-1H-imidazole-4-carboxylic acid methyl ester;

5-{4-[(4-chlorophenyl)-dimethylaminomethyl]-cyclohexyl}-4-isobutyl-1-phenethyl-4,5-dihydro-1H-imidazole-4-carboxylic acid methyl ester;

4-(4-chlorobenzyl)-5-{4-[(4-chlorophenyl)-dimethylaminomethyl]-cyclohexyl}-1-phenethyl-4,5-dihydro-1H-imidazole-4-carboxylic acid methyl ester;

4-butyl-5-{4-[(4-chlorophenyl)-dimethylaminomethyl]-cyclohexylmethyl}-1-phenethyl-4,5-dihydro-1H-imidazole-4-carboxylic acid methyl ester;

5-{4-[(4-chlorophenyl)-dimethylaminomethyl]-cyclohexylmethyl}-4-isobutyl-1-phenethyl-4,5-dihydro-1H-imidazole-4-carboxylic acid methyl ester;

4-(4-chlorobenzyl)-5-{4-[(4-chlorophenyl)-dimethylaminomethyl]-cyclohexylmethyl}-1-phenethyl-4,5-dihydro-1H-imidazole-4-carboxylic acid methyl ester;

4-butyl-5-{4-[(4-chlorophenyl)-dimethylaminomethyl]-cyclohexylmethyl}-1-phenethyl-4,5-dihydro-1H-imidazole-4-carboxylic acid methyl ester;

1-benzyl-5-{4-[dimethylamino-(3-fluorophenyl)-methyl]-cyclohexyl}-4-isobutyl-4,5-dihydro-1H-imidazole-4-carboxylic acid methyl ester;

1-benzyl-4-(4-chlorobenzyl)-5-{4-[dimethylamino-(3-fluorophenyl)-methyl]-cyclohexyl}-4,5-dihydro-1H-imidazole-4-carboxylic acid methyl ester;

1-benzyl-5-{4-[(4-chlorophenyl)-dimethylaminomethyl]-cyclohexyl}-4-isobutyl-4,5-dihydro-1H-imidazole-4-carboxylic acid methyl ester;

1-benzyl-4-(4-chlorobenzyl)-5-{4-[(4-chlorophenyl)-dimethylaminomethyl]-cyclohexyl}-4,5-dihydro-1H-imidazole-4-carboxylic acid methyl ester;

1-benzyl-5-{4-[(4-chlorophenyl)-dimethylaminomethyl]-cyclohexylmethyl}-4-isobutyl-4,5-dihydro-1H-imidazole-4-carboxylic acid methyl ester;

5-{4-[(4-chlorophenyl)-dimethylaminomethyl]-cyclohexyl}-1-cyclohexyl-4-(2-methoxycarbonylethyl)-4,5-dihydro-1H-imidazole-4-carboxylic acid methyl ester;

4-benzylsulfanylmethyl-5-{4-[(4-chlorophenyl)-dimethylaminomethyl]-cyclohexyl}-1-cyclohexyl-4,5-dihydro-1H-imidazole-4-carboxylic acid methyl ester;

5-{4-[(4-chlorophenyl)-dimethylaminomethyl]-cyclohexylmethyl}-1-cyclohexyl-4-(2-methoxycarbonylethyl)-4,5-dihydro-1H-imidazole-4-carboxylic acid methyl ester;

1-benzyl-5-{4-[dimethylamino-(3-fluorophenyl)-methyl]-cyclohexylmethyl}-4-propyl-4,5-dihydro-1H-imidazole-4-carboxylic acid methyl ester;

5-{4-[(4-chlorophenyl)-dimethylaminomethyl]-cyclohexylmethyl}-1-cyclohexyl-4-methylsulfanylmethyl-4,5-dihydro-1H-imidazole-4-carboxylic acid methyl ester;

4-benzylsulfanylmethyl-5-{4-[(4-chlorophenyl)-dimethylaminomethyl]-cyclohexylmethyl}-1-cyclohexyl-4,5-dihydro-1H-imidazole-4-carboxylic acid methyl ester;

5-{4-[dimethylamino-(3-fluorophenyl)-methyl]-cyclohexyl}-4-methylsulfanylmethyl-1-propyl-4,5-dihydro-1H-imidazole-4-carboxylic acid methyl ester;

4-benzylsulfanylmethyl-5-{4-[dimethylamino-(3-fluorophenyl)-methyl]-cyclohexyl}-1-propyl-4,5-dihydro-1H-imidazole-4-carboxylic acid methyl ester;

5-{4-[(4-chlorophenyl)-dimethylaminomethyl]-cyclohexyl}-4-(2-methoxycarbonylethyl)-1-propyl-4,5-dihydro-1H-imidazole-4-carboxylic acid methyl ester;

4-benzylsulfanylmethyl-5-{4-[(4-chlorophenyl)-dimethylaminomethyl]-cyclohexyl}-1-propyl-4,5-dihydro-1H-imidazole-4-carboxylic acid methyl ester;

5-{4-[(4-chlorophenyl)-dimethylaminomethyl]-cyclohexylmethyl}-4-(2-methoxycarbonylethyl)-1-propyl-4,5-dihydro-1H-imidazole-4-carboxylic acid methyl ester;

4-sec-butyl-5-{4-[(4-chlorophenyl)-dimethylaminomethyl]-cyclohexylmethyl}-1-propyl-4,5-dihydro-1H-imidazole-4-carboxylic acid methyl ester;

5-{4-[(4-chlorophenyl)-dimethylaminomethyl]-cyclohexylmethyl}-4-methylsulfanylmethyl-1-propyl-4,5-dihydro-1H-imidazole-4-carboxylic acid methyl ester;

4-benzylsulfanylmethyl-5-{4-[(4-chlorophenyl)-dimethylaminomethyl]-cyclohexylmethyl}-1-propyl-4,5-dihydro-1H-imidazole-4-carboxylic acid methyl ester;

1-butyl-5-{4-[dimethylamino-(3-fluorophenyl)-methyl]-cyclohexyl}-4-(2-methoxycarbonylethyl)-4-5-dihydro-1H-imidazole-4-carboxylic acid methyl ester;
1-butyl-5-{4-[dimethylamino-(3-fluorophenyl)-methyl]-cyclohexyl}-4-methylsulfanylmethyl-4,5-dihydro-1H-imidazole-4-carboxylic acid methyl ester;
4-benzylsulfanylmethyl-1-butyl-5-{4-[dimethylamino-(3-fluorophenyl)-methyl]-cyclohexyl}-4,5-dihydro-1H-imidazole-4-carboxylic acid methyl ester;
1-butyl-5-{4-[(4-chlorophenyl)-dimethylaminomethyl]-cyclohexyl}-4-(2-methoxycarbonylethyl)-4,5-dihydro-1H-imidazole-4-carboxylic acid methyl ester;
4-benzylsulfanylmethyl-1-butyl-5-{4-[(4-chlorophenyl)-dimethylaminomethyl]-cyclohexyl}-4,5-dihydro-1H-imidazole-4-carboxylic acid methyl ester;
1-butyl-5-{4-[(4-chlorophenyl)-dimethylaminomethyl]-cyclohexylmethyl}-4-(2-methoxycarbonylethyl)-4,5-dihydro-1H-imidazole-4-carboxylic acid methyl ester;
5-[4-(1-dimethylamino-3-phenylpropyl)-cyclohexylmethyl]-4-(2-methoxycarbonylethyl)-1-propyl-4,5-dihydro-1H-imidazole-4-carboxylic acid methyl ester;
1-butyl-5-{4-[dimethylamino-(3-fluorophenyl)-methyl]-cyclohexylmethyl}-4-(2-methoxycarbonylethyl)-4,5-dihydro-1H-imidazole-4-carboxylic acid methyl ester;
1-butyl-4-sec-butyl-5-{4-[dimethylamino-(3-fluorophenyl)-methyl]-cyclohexylmethyl}-4,5-dihydro-1H-imidazole-4-carboxylic acid methyl ester;
1-butyl-5-{4-[dimethylamino-(3-fluorophenyl)-methyl]-cyclohexylmethyl}-4-methylsulfanylmethyl-4,5-dihydro-1H-imidazole-4-carboxylic acid methyl ester;
4-benzylsulfanylmethyl-1-butyl-5-{4-[dimethylamino-(3-fluorophenyl)-methyl]-cyclohexylmethyl}-4,5-dihydro-1H-imidazole-4-carboxylic acid methyl ester;
1-butyl-5-{4-[dimethylamino-(4-fluorophenyl)-methyl]-cyclohexylmethyl}-4-(2-methoxycarbonylethyl)-4,5-dihydro-1H-imidazole-4-carboxylic acid methyl ester;
1-butyl-5-{4-[dimethylamino-(4-fluorophenyl)-methyl]-cyclohexylmethyl}-4-methylsulfanylmethyl-4,5-dihydro-1H-imidazole-4-carboxylic acid methyl ester;
1-butyl-5-[4-(1-dimethylamino-3-phenylpropyl)-cyclohexylmethyl]-4-(2-methoxycarbonylethyl)-4,5-dihydro-1H-imidazole-4-carboxylic acid methyl ester;
4-benzylsulfanylmethyl-1-butyl-5-[4-(1-dimethylamino-3-phenylpropyl)cyclohexylmethyl]-4,5-dihydro-1H-imidazole-4-carboxylic acid methyl ester;
5-{4-[dimethylamino-(3-fluorophenyl)-methyl]-cyclohexylmethyl}-4-(2-methoxycarbonylethyl)-1-phenethyl-4,5-dihydro-1H-imidazole-4-carboxylic acid methyl ester;
4-sec-butyl-5-{4-[dimethylamino-(3-fluorophenyl)-methyl]-cyclohexylmethyl}-1-phenethyl-4,5-dihydro-1H-imidazole-4-carboxylic acid methyl ester;
4-benzylsulfanylmethyl-5-{4-[dimethylamino-(3-fluorophenyl)-methyl]-cyclohexylmethyl}-1-phenethyl-4,5-dihydro-1H-imidazole-4-carboxylic acid methyl ester;
5-{4-[dimethylamino-(4-fluorophenyl)-methyl]-cyclohexylmethyl}-4-(2-methoxycarbonylethyl)-1-phenethyl-4,5-dihydro-1H-imidazole-4-carboxylic acid methyl ester;
5-[4-(1-dimethylamino-3-phenylpropyl)-cyclohexylmethyl]-4-(2-methoxycarbonylethyl)-1-phenethyl-4,5-dihydro-1H-imidazole-4-carboxylic acid methyl ester;
1-benzyl-5-{4-[dimethylamino-(3-fluorophenyl)-methyl]-cyclohexylmethyl}-4-(2-methoxycarbonylethyl)-4,5-dihydro-1H-imidazole-4-carboxylic acid methyl ester;
1-benzyl-4-benzylsulfanylmethyl-5-{4-[dimethylamino-(3-fluorophenyl)-methyl]-cyclohexylmethyl}-4,5-dihydro-1H-imidazole-4-carboxylic acid methyl ester;
1-benzyl-5-{4-[dimethylamino-(4-fluorophenyl)-methyl]-cyclohexylmethyl}-4-(2-methoxycarbonylethyl)-4,5-dihydro-1H-imidazole-4-carboxylic acid methyl ester;
1-butyl-4-sec-butyl-5-{4-[(4-chlorophenyl)-dimethylaminomethyl]-cyclohexylmethyl}-4,5-dihydro-1H-imidazole-4-carboxylic acid methyl ester;
1-butyl-5-{4-[(4-chlorophenyl)-dimethylaminomethyl]-cyclohexylmethyl}-4-methylsulfanylmethyl-4,5-dihydro-1H-imidazole-4-carboxylic acid methyl ester;
4-benzylsulfanylmethyl-1-butyl-5-{4-[(4-chlorophenyl)-dimethylaminomethyl]-cyclohexylmethyl}-4,5-dihydro-1H-imidazole-4-carboxylic acid methyl ester;
5-{4-[dimethylamino-(3-fluorophenyl)-methyl]-cyclohexyl}-4-(2-methoxycarbonylethyl)-1-phenethyl-4,5-dihydro-1H-imidazole-4-carboxylic acid methyl ester;
4-benzylsulfanylmethyl-5-{4-[dimethylamino-(3-fluorophenyl)-methyl]-cyclohexyl}-1-phenethyl-4,5-dihydro-1H-imidazole-4-carboxylic acid methyl ester;
4-benzylsulfanylmethyl-5-{4-[(4-chlorophenyl)-dimethylaminomethyl]-cyclohexyl}-1-phenethyl-4,5-dihydro-1H-imidazole-4-carboxylic acid methyl ester;
5-{4-[(4-chlorophenyl)-dimethylaminomethyl]-cyclohexylmethyl}-4-(2-methoxycarbonylethyl)-1-phenethyl-4,5-dihydro-1H-imidazole-4-carboxylic acid methyl ester;
1-benzyl-5-{4-[dimethylamino-(3-fluorophenyl)-methyl]-cyclohexyl}-4-(2-methoxycarbonylethyl)-1H-imidazole-4-carboxylic acid methyl ester;
1-benzyl-5-{4-[dimethylamino-(3-fluorophenyl)-methyl]-cyclohexyl}-4-methylsulfanylmethyl-4,5-dihydro-1H-imidazole-4-carboxylic acid methyl ester;
1-benzyl-4-benzylsulfanylmethyl-5-{4-[dimethylamino-(3-fluorophenyl)-methyl]-cyclohexyl}-4,5-dihydro-1H-imidazole-4-carboxylic acid methyl ester;
1-benzyl-4-benzylsulfanylmethyl-5-{4-[(4-chlorophenyl)-dimethylaminomethyl]-cyclohexyl}-4,5-dihydro-1H-imidazole-4-carboxylic acid methyl ester;
1-benzyl-5-{4-[(4-chlorophenyl)-dimethylaminomethyl]-cyclohexylmethyl}-4-(2-methoxycarbonylethyl)-4,5-dihydro-1H-imidazole-4-carboxylic acid methyl ester;
1-benzyl-5-{4-[(4-chlorophenyl)-dimethylaminomethyl]-cyclohexylmethyl}-4-methylsulfanylmethyl-4,5-dihydro-1H-imidazole-4-carboxylic acid methyl ester;
1-benzyl-4-benzylsulfanylmethyl-5-{4-[(4-chlorophenyl)-dimethylaminomethyl]-cyclohexylmethyl}-4,5-dihydro-1H-imidazole-4-carboxylic acid methyl ester;
1-cyclohexyl-5-{4-[dimethylamino-(3-fluorophenyl)-methyl]-cyclohexylmethyl}-4-propyl-4,5-dihydro-1H-imidazole-4-carboxylic acid methyl ester;
1-cyclohexyl-5-{4-[dimethylamino-(3-fluorophenyl)-methyl]-cyclohexylmethyl}-4-(2-methylsulfanylethyl)-4,5-dihydro-1H-imidazole-4-carboxylic acid methyl ester;
1-cyclohexyl-5-{4-[dimethylamino-(3-fluorophenyl)-methyl]-cyclohexylmethyl}-4-methyl-4,5-dihydro-1H-imidazole-4-carboxylic acid methyl ester;
1-cyclohexyl-5-{4-[dimethylamino-(4-fluorophenyl)-methyl]-cyclohexylmethyl}-4-propyl-4,5-dihydro-1H-imidazole-4-carboxylic acid methyl ester;
1-cyclohexyl-5-{4-[dimethylamino-(4-fluorophenyl)-methyl]-cyclohexylmethyl}-4-(2-methylsulfanylethyl)-4,5-dihydro-1H-imidazole-4-carboxylic acid methyl ester;
1-cyclohexyl-5-{4-[dimethylamino-(4-fluorophenyl)-methyl]-cyclohexylmethyl}-4-methyl-4,5-dihydro-1H-imidazole-4-carboxylic acid methyl ester;
1-cyclohexyl-5-[4-(1-dimethylamino-3-phenylpropyl)-cyclohexylmethyl]-4-propyl-4,5-dihydro-1H-imidazole-4-carboxylic acid methyl ester;

1-cyclohexyl-5-[4-(1-dimethylamino-3-phenylpropyl)-cyclohexylmethyl]-4-(2-methylsulfanylethyl)-4,5-dihydro-1H-imidazole-4-carboxylic acid methyl ester;
1-cyclohexyl-5-[4-(1-dimethylamino-3-phenylpropyl)-cyclohexylmethyl]-4-methyl-4,5-dihydro-1H-imidazole-4-carboxylic acid methyl ester;
5-{4-[dimethylamino-(3-fluorophenyl)-methyl]-cyclohexylmethyl}-1,4-dipropyl-4,5-dihydro-1H-imidazole-4-carboxylic acid methyl ester;
5-{4-[dimethylamino-(3-fluorophenyl)-methyl]-cyclohexylmethyl}-4-(2-methylsulfanylethyl)-1-propyl-4,5-dihydro-1H-imidazole-4-carboxylic acid methyl ester;
1-benzyl-4-(4-chlorobenzyl)-5-{4-[(4-chlorophenyl)-dimethylaminomethyl]-cyclohexylmethyl}-4,5-dihydro-1H-imidazole-4-carboxylic acid methyl ester;
1-benzyl-4-butyl-5-{4-[(4-chlorophenyl)-dimethylaminomethyl]-cyclohexylmethyl}-4,5-dihydro-1H-imidazole-4-carboxylic acid methyl ester;
1-cyclohexyl-5-{4-[dimethylamino-(3-fluorophenyl)-methyl]-cyclohexyl}-4-(2-methoxycarbonylethyl)-4,5-dihydro-1H-imidazole-4-carboxylic acid methyl ester;
4-benzylsulfanylmethyl-1-cyclohexyl-5-{4-[dimethylamino-(3-fluorophenyl)-methyl]-cyclohexyl}-4,5-dihydro-1H-imidazole-4-carboxylic acid methyl ester;
5-{4-[dimethylamino-(3-fluorophenyl)-methyl]-cyclohexylmethyl}-4-methyl-1-propyl-4,5-dihydro-1H-imidazole-4-carboxylic acid methyl ester;
5-{4-[dimethylamino-(4-fluorophenyl)-methyl]-cyclohexylmethyl}-1,4-dipropyl-4,5-dihydro-1H-imidazole-4-carboxylic acid methyl ester;
5-{4-[dimethylamino-(4-fluorophenyl)-methyl]-cyclohexylmethyl}-4-(2-methylsulfanylethyl)-1-propyl-4,5-dihydro-1H-imidazole-4-carboxylic acid methyl ester;
5-[4-(1-dimethylamino-3-phenylpropyl)-cyclohexylmethyl]-1,4-dipropyl-4,5-dihydro-1H-imidazole-4-carboxylic acid methyl ester;
5-[4-(1-dimethylamino-3-phenylpropyl)-cyclohexylmethyl]-4-(2-methylsulfanylethyl)-1-propyl-1H-imidazole-4-carboxylic acid methyl ester;
1-butyl-5-{4-[dimethylamino-(3-fluorophenyl)-methyl]-cyclohexylmethyl}-4-propyl-4,5-dihydro-1H-imidazole-4-carboxylic acid methyl ester;
1-butyl-5-{4-[dimethylamino-(3-fluorophenyl)-methyl]-cyclohexylmethyl}-4-(2-methylsulfanylethyl)-4,5-dihydro-1H-imidazole-4-carboxylic acid methyl ester;
1-butyl-5-{4-[dimethylamino-(3-fluorophenyl)-methyl]-cyclohexylmethyl}-4-methyl-4,5-dihydro-1H-imidazole-4-carboxylic acid methyl ester;
1-butyl-5-{4-[dimethylamino-(4-fluorophenyl)-methyl]-cyclohexylmethyl}-4-propyl-4,5-dihydro-1H-imidazole-4-carboxylic acid methyl ester;
1-butyl-5-{4-[dimethylamino-(4-fluorophenyl)-methyl]-cyclohexylmethyl}-4-(2-methylsulfanylethyl)-4,5-dihydro-1H-imidazole-4-carboxylic acid methyl ester;
1-butyl-5-[4-(1-dimethylamino-3-phenylpropyl)-cyclohexylmethyl]-4-propyl-4,5-dihydro-1H-imidazole-4-carboxylic acid methyl ester;
1-butyl-5-[4-(1-dimethylamino-3-phenylpropyl)-cyclohexylmethyl]-4-(2-methylsulfanylethyl)-4,5-dihydro-1H-imidazole-4-carboxylic acid methyl ester;
5-{4-[dimethylamino-(3-fluorophenyl)-methyl]-cyclohexylmethyl}-4-propyl-1-phenethyl-4,5-dihydro-1H-imidazole-4-carboxylic acid methyl ester;
5-{4-[dimethylamino-(3-fluorophenyl)-methyl]-cyclohexylmethyl}-4-(2-methylsulfanylethyl)-1-phenethyl-4,5-dihydro-1H-imidazole-4-carboxylic acid methyl ester;
5-{4-[dimethylamino-(3-fluorophenyl)-methyl]-cyclohexylmethyl}-4-methyl-1-phenethyl-4,5-dihydro-1H-imidazole-4-carboxylic acid methyl ester;
5-{4-[dimethylamino-(4-fluorophenyl)-methyl]-cyclohexylmethyl}-1-phenethyl-4-propyl-4,5-dihydro-1H-imidazole-4-carboxylic acid methyl ester;
5-{4-[dimethylamino-(4-fluorophenyl)-methyl]-cyclohexylmethyl}-4-(2-methylsulfanylethyl)-1-phenethyl-4,5-dihydro-1H-imidazole-4-carboxylic acid methyl ester;
5-{4-[dimethylamino-(4-fluorophenyl)-methyl]-cyclohexylmethyl}-4-methyl-1-phenethyl-4,5-dihydro-1H-imidazole-4-carboxylic acid methyl ester;
5-[4-dimethylamino-3-phenylpropyl)-cyclohexylmethyl]-1-phenethyl-4-propyl-4,5-dihydro-1H-imidazole-4-carboxylic acid methyl ester;
5-[4-(1-dimethylamino-3-phenylpropyl)-cyclohexylmethyl]-4-(2-methylsulfanylethyl)-1-phenethyl-4,5-dihydro-1H-imidazole-4-carboxylic acid methyl ester;
5-[4-(1-dimethylamino-3-phenylpropyl)-cyclohexylmethyl]-4-methyl-1-phenethyl-4,5-dihydro-1H-imidazole-4-carboxylic acid methyl ester;
1-benzyl-5-{4-[dimethylamino-(3-fluorophenyl)-methyl]-cyclohexylmethyl}-4-propyl-4,5-dihydro-1H-imidazole-4-carboxylic acid methyl ester;
1-benzyl-5-{4-[dimethylamino-(3-fluorophenyl)-methyl]-cyclohexylmethyl}-4-(2-methylsulfanylethyl)-4,5-dihydro-1H-imidazole-4-carboxylic acid methyl ester;
1-benzyl-5-{4-[dimethylamino-(3-fluorophenyl)-methyl]-cyclohexylmethyl}-4-methyl-4,5-dihydro-1H-imidazole-4-carboxylic acid methyl ester;
1-benzyl-5-{4-[dimethylamino-(4-fluorophenyl)-methyl]-cyclohexylmethyl}-4-propyl-4,5-dihydro-1H-imidazole-4-carboxylic acid methyl ester;
1-benzyl-5-{4-[dimethylamino-(4-fluorophenyl)-methyl]-cyclohexylmethyl}-4-(2-methylsulfanylethyl)-4,5-dihydro-1H-imidazole-4-carboxylic acid methyl ester;
1-benzyl-5-{4-[dimethylamino-(4-fluorophenyl)-methyl]-cyclohexylmethyl}-4-methyl-4,5-dihydro-1H-imidazole-4-carboxylic acid methyl ester;
1-benzyl-5-[4-(1-dimethylamino-3-phenylpropyl)-cyclohexylmethyl]-4-propyl-4,5-dihydro-1H-imidazole-4-carboxylic acid methyl ester;
1-benzyl-5-[4-(1-dimethylamino-3-phenylpropyl)-cyclohexylmethyl]-4-(2-methylsulfanylethyl)-4,5-dihydro-1H-imidazole-4-carboxylic acid methyl ester;
1-benzyl-5-[4-(1-dimethylamino-3-phenylpropyl)-cyclohexylmethyl]-4-methyl-4,5-dihydro-1H-imidazole-4-carboxylic acid methyl ester;
1-cyclohexyl-5-{4-[dimethylamino-(3-fluorophenyl)-methyl]-cyclohexylmethyl}-4-(2-methoxycarbonylethyl)-4,5-dihydro-1H-imidazole-4-carboxylic acid methyl ester;
4-sec-butyl-1-cyclohexyl-5-{4-[dimethylamino-(3-fluorophenyl)-methyl]-cyclohexylmethyl}-4,5-dihydro-1H-imidazole-4-carboxylic acid methyl ester;
1-cyclohexyl-5-{4-[dimethylamino-(3-fluorophenyl)-methyl]-cyclohexylmethyl}-4-methylsulfanylmethyl-4,5-dihydro-1H-imidazole-4-carboxylic acid methyl ester;
4-benzylsulfanylmethyl-1-cyclohexyl-5-{4-[dimethylamino-(3-fluorophenyl)-methyl]-cyclohexylmethyl}-4,5-dihydro-1H-imidazole-4-carboxylic acid methyl ester
1-cyclohexyl-5-{4-[dimethylamino-(4-fluorophenyl)-methyl]-cyclohexylmethyl}-4-(2-methoxycarbonylethyl)-4,5-dihydro-1H-imidazole-4-carboxylic acid methyl ester;
4-sec-butyl-1-cyclohexyl-5-{4-[dimethylamino-(4-fluorophenyl)-methyl]-cyclohexylmethyl}-4,5-dihydro-1H-imidazole-4-carboxylic acid methyl ester;

1-cyclohexyl-5-{4-[dimethylamino-(4-fluorophenyl)-methyl]-cyclohexylmethyl}-4-methylsulfanylmethyl-4,5-dihydro-1H-imidazole-4-carboxylic acid methyl ester;
1-cyclohexyl-5-[4-(1-dimethylamino-3-phenylpropyl)-cyclohexylmethyl]-4-(2-methoxycarbonylethyl)-4,5-dihydro-1H-imidazole-4-carboxylic acid methyl ester;
1-cyclohexyl-5-[4-(1-dimethylamino-3-phenylpropyl)-cyclohexylmethyl]-4-methylsulfanylmethyl-4,5-dihydro-1H-imidazole-4-carboxylic acid methyl ester;
4-benzylsulfanylmethyl-1-cyclohexyl-5-[4-(1-dimethylamino-3-phenylpropyl)-cyclohexylmethyl]-4,5-dihydro-1H-imidazole-4-carboxylic acid methyl ester;
5-{4-[dimethylamino-(3-fluorophenyl)-methyl]-cyclohexylmethyl}-4-(2-methoxycarbonylethyl)-1-propyl-4,5-dihydro-1H-imidazole-4-carboxylic acid methyl ester;
5-{4-[dimethylamino-(3-fluorophenyl)-methyl]-cyclohexylmethyl}-4-methylsulfanylmethyl-1-propyl-4,5-dihydro-1H-imidazole-4-carboxylic acid methyl ester;
5-{4-[dimethylamino-(4-fluorophenyl)-methyl]-cyclohexylmethyl}-4-(2-methoxycarbonylethyl)-1-propyl-4,5-dihydro-1H-imidazole-4-carboxylic acid methyl ester;
5-{4-[dimethylamino-(4-fluorophenyl)-methyl]-cyclohexylmethyl}-4-methylsulfanylmethyl-1-propyl-4,5-dihydro-1H-imidazole-4-carboxylic acid methyl ester;
4-benzylsulfanylmethyl-5-{4-[dimethylamino-(4-fluorophenyl)-methyl]-cyclohexylmethyl}-1-propyl-4,5-dihydro-1H-imidazole-4-carboxylic acid methyl ester; and
methyl-4-sec-butyl-5-((4-((4-chlorophenyl)(dimethylamino)methyl)cyclohexyl)-methyl)-1-cyclohexyl-4,5-dihydro-1H-imidazole-4-carboxylate;

in the form of a racemate; in the form of an enantiomer, diastereomer, mixture of the enantiomers or diastereomers; in the form of an individual enantiomer or diastereomer; in the form of a base or a salt of a physiologically compatible acid.

EXAMPLES

General instructions for the synthesis of
4-[dimethylamino-methyl]-cyclohexane-carbaldehydes
and
4-[dimethylamino-methyl]-cyclohexylacetaldehydes

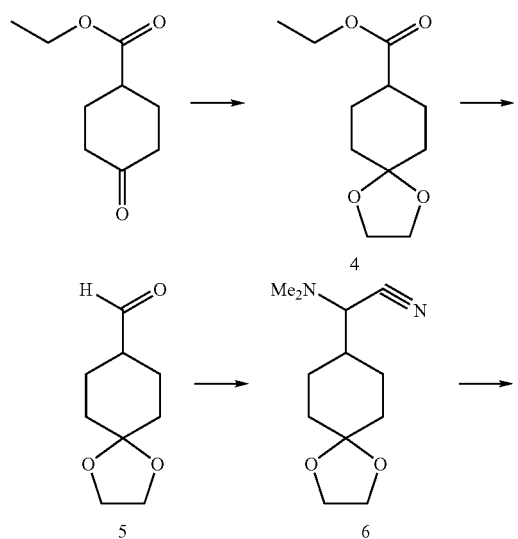

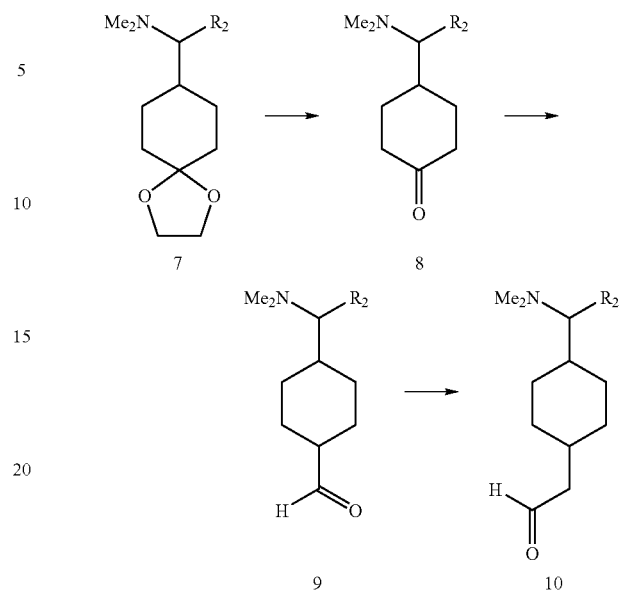

1st Stage

Synthesis of the
1,4-dioxa-spiro[4.5]decane-8-carboxylic acid ethyl ester 4

4-oxo-cyclohexanecarboxylic acid ethyl ester (52.8 g, 0.31 mole, Merck, Order No. 814249), ethylene glycol (67.4 g, 1.08 mole) and p-toluenesulfonic acid (0.7 g) in toluene (160 ml) were stirred for 20 hours at RT, the reaction solution was poured into diethyl ether (300 ml), and washed with water, sodium hydrogen carbonate solution and sodium chloride solution. The solution was tried (Na$_2$SO$_4$), concentrated by evaporation in vacuo, and the remaining colorless liquid was processed further without purification.

2nd Stage

Synthesis of the
1,4-dioxa-spiro[4.5]decane-8-carbaldehyde 5

Diisobutyl aluminium hydride (1.5 M solution in toluene, 102 ml, 153 mmole) was added dropwise to a solution of 1,4-dioxa-spiro[4.5]decane-8-carboxylic acid ethyl ester 4 (32.13 g, 150 mmole) in absolute toluene (160 ml) at −70° to −65° C. under argon and stirred for 30 minutes. The reaction mixture was then quenched at −70° to −60° C. by adding methanol (80 ml). The reaction solution was heated to RT, saturated sodium chloride solution (100 ml) was added, and the reaction solution was suction filtered through diatomaceous earth. The diatomaceous earth was washed twice with ethyl acetate, and the aqueous solution was separated and extracted twice with ethyl acetate. The combined organic extracts were washed with saturated sodium chloride solution, dried over sodium sulfate, and concentrated by evaporation in vacuo.

3rd Stage

Synthesis of the dimethylamino-(1,4-dioxa-spiro [4.5]dec-8-yl)-acetonitrile 6

40% aqueous dimethylamine solution (85 ml, 0.67 mole), 1,4-dioxa-spiro-[4.5]decane-8-carbaldehyde 5 (240 g, 0.141 mole) and potassium cyanide (22.05 g, 0.338 mole) were added while cooling with ice to a mixture of 4N hydrochloric acid (37 ml) and methanol (22 ml). The mixture was stirred for four days at room temperature and then extracted, after adding water (80 ml), with diethyl ether (4×100 ml). The organic phase was dried over sodium sulfate, concentrated by evaporation in vacuo, and the product was obtained as a white solid.

4th Stage

Synthesis of the [(1,4-dioxa-spiro[4.5]dec-8-yl)-methyl]-dimethylamine 7

A solution of the aminonitrile 6i (19.89 g 88 mmole) in absolute THF (160 ml) or absolute diethyl ether (160 ml), depending on the solvent of the Grignard reagent, was added dropwise to a 1M solution of the corresponding Grignard reagent in THF or diethyl ether (220 ml, 220 mmole) under argon and cooling with ice, and stirred for 20 hours at RT. To work up the reaction mixture saturated ammonium chloride solution (100 ml) and water (100 ml) were added while cooling with ice, and the mixture was extracted with diethyl ether (3×100 ml). The organic phase was washed with water and saturated sodium chloride solution, dried ($Na_2SO_4$) and concentrated by evaporation. The product obtained was used without further purification in the next stage.

5th Stage

Synthesis of the 4-[dimethylaminomethyl]-cyclohexanones

The crude product of the corresponding [(1,4-dioxa-spiro [4.5]dec-8-yl)-methyl]-dimethylamine 7i (88 mmole) was dissolved in water (40 ml), concentrated hydrochloric acid (59 ml) was added, and the whole was stirred to 20 hours at RT. The reaction mixture was extracted with diethyl ether (2×100 ml), the aqueous phase was made alkaline with 5N NaOH while cooling with ice, extracted with dichloromethane (3×100 ml), dried, and concentrated by evaporation. The products were obtained as white solids or oils.

6th Stage

Synthesis of the 4-[dimethylaminomethyl]-cyclohexane-carbaldehyde 9

(Methoxymethyl)triphenylphosphonium chloride (25.7 g, 75 mmole) was suspended in absolute THF (100 ml) under argon, potassium tert-butylate (8.42 g, 75 mmole) dissolved in absolute THF (70 ml) was added dropwise, and then stirred for 15 minutes at 0° C. The corresponding 4-[dimethylaminomethyl]-cyclohexanone 8 (50 mmole), dissolved in absolute THF (75 ml), was then added dropwise to the above solution and stirred overnight at RT. The mixture was hydrolysed by adding dropwise water (38 ml) and 6N HCL 112 ml) while cooling with iced water. After stirring for one hour at RT the mixture was extracted with ether (10×50 ml), the aqueous phase was adjusted to pH 11 with 5N NaOH, shaken with ethyl acetate (3×50 ml), dried over $Na_2SO_4$, and concentrated by evaporation in vacuo. The crude product was purified by flash chromatography with ethyl acetate/cyclohexane (1:1). As a rule two diastereomers were obtained in different ratios.

7th Stage

Synthesis of the {4-[dimethylaminomethyl]-cyclohexyl}-acetaldehydes 10

(Methoxymethyl)triphenylphosphonium chloride (43.53 g, 127 mmole) was suspended in absolute THF (200 ml) under argon, potassium tert-butylate (14.25 g, 127 mmole), dissolved in absolute THF (130 ml) was added dropwise at 0° C., and then stirred for 15 minutes at 0° C. The corresponding 4-[dimethylaminomethyl]-cyclohexane carbaldehyde 9i (85 mmole), dissolved in absolute THF (130 ml), was then added dropwise and stirred overnight at RT. The mixture was hydrolysed by adding dropwise water (80 ml) and 6N HCl (200 ml), while cooling with iced water. After stirring for one hour at RT the mixture was extracted 10 times with ether (each time 100 ml). The aqueous phase was adjusted to pH 11 With 5N NaOH, shaken three times with ethyl acetate (each time 100 ml), dried over $Na_2SO_4$, and concentrated by evaporation in vacuo. The crude product was purified by flash chromatography with ethyl acetate/cyclohexane (1:1 or 1:2). As a rule two diastereomers were obtained in different ratios. The isonitrile esters (component C) were either obtained commercially or were prepared similarly to the method described in R. S. Bon et al, Org. Lett. 2003, 5, 20, 3759-3762. In the first stage a formylation was first of all carried out. The isonitrile is obtained therefrom by adding $POCl_3$.

Methyl 2-(formylamino)-3-phenylpropanoate 2

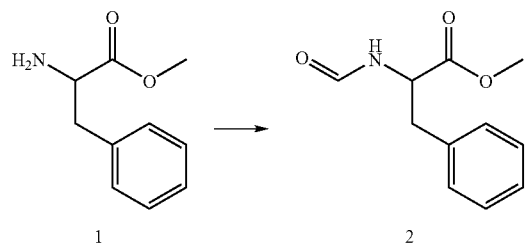

$^1$H-NMR (300 MHz, $CDCl_3$): δ=3.07-3.22 (m, 2H); 3.74 (s, 3H); 4.92-5.01 (m, 1H); 6.20 (bs, 1H); 7.07-7.15 (m, 2H); 7.23-7.34 (m, 3H); 8.15 (s, 1H).

2-isocyano-3-phenylpropionic acid methyl ester 3

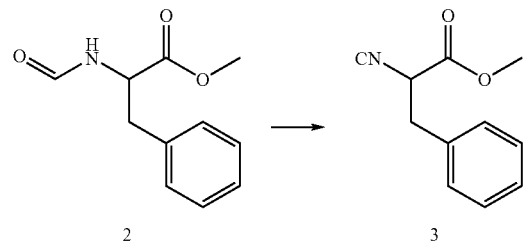

$^1$H-NMR (300 MHz, CDCl$_3$): δ=3.14 (dd, 1H, $J_{AA'}$=8.66 Hz, $J_{AB}$=8.29 Hz); 3.23 (dd, 1H, $J_{AA'}$=4.52 Hz, $J_{AB}$=4.90 Hz); 3.80 (s, 3H), 4.46 (dd, 1H, J=8.29; J=4.90 Hz); 7.22-7.39 (m, 5H).

1,4-dioxa-spiro[4.5]decane-8-carboxylic acid ethyl ester 4

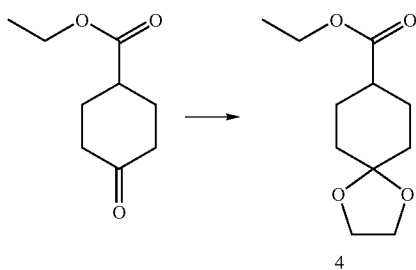

4-oxo-cyclohexanecarboxylic acid ethyl ester (52.8 g, 0.31 mole, Merck, Order No. 814249), ethylene glycol (67.4 g, 1.08 mole) and p-toluenesulfonic acid (0.7 g) in toluene (160 ml) were stirred for 20 hours at RT, and the reaction solution was poured into diethyl ether (300 ml) and washed with water, sodium hydrogen carbonate solution and sodium chloride solution. The solution was dried (Na$_2$SO$_4$), concentrated by evaporation in vacuo, and the remaining colorless liquid was processed further without purification.

Yield 66.5 g (100%) $^1$H-NMR (CDCl$_3$): 1.24 (t, 3H, 1.53 (m, 2H); 1.76 (m, 4H); 1.92 (m, 2H); 2.31 (m, 1H); 3.91 (s, 4H); 4.11 (q, 2H). $^{13}$C-NMR (CDCl$_3$): 14.28 (q); 26.32 (t); 33.76 (t); 41.59 (d); 60.14 (t); 64.21 (t); 107.90 (d); 174.77 (s).

1,4-dioxa-spiro[4.5]decane-8-carbaldehyde 5

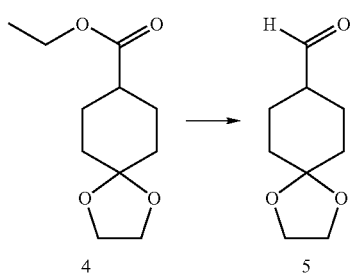

Diisobutyl aluminium hydride (1.5 M solution in toluene, 102 ml, 153 mmole) was added dropwise at −70° to −65° C. under argon to a solution of 1,4-dioxaspior[4.5]decane-8-carboxylic acid ethyl ester 4 (32.13 g, 150 mmole) in absolute toluene (160 ml), and stirred for 30 minutes. The reaction mixture was then quenched at −70° to −60° C. by adding methanol (80 ml). The reaction solution was heated to RT, saturated sodium chloride solution (100 ml) was added, and the reaction solution was suction filtered through diatomaceous earth. The diatomaceous earth was washed twice with ethyl acetate, and the aqueous solution was separated and extracted twice with ethyl acetate. The combined organic extracts were washed with saturated sodium chloride solution, dried over sodium sulfate, and concentrated by evaporation in vacuo.

Yield: 24.01 g (94%), yellow oil $^1$H-NMR (CDCl$_3$): 1.54 (m, 2H); 1.74 (m, 4H); 1.91 (m, 2H); 2.21 (m, 1H); 3.91 (s, 4H); 9.60 (s, 1H). $^{13}$C-NMR (CDCl$_3$): 23.35 (t); 33.37 (t); 48.18 (d); 64.30 (t); 107.89 (d); 203.51 (s).

Dimethylamino-(1,4-dioxa-spiro[4.5]dec-8-yl)-acetonitrile 6

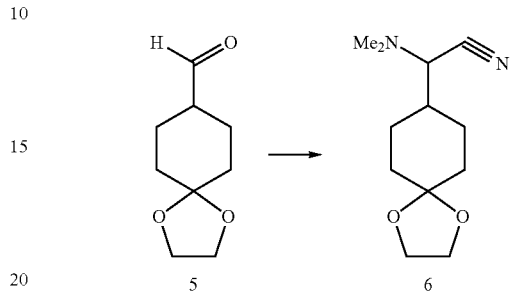

40% aqueous dimethylamine solution (85 ml, 0.67 mole), 1,4-dioxa-spiro-[4.5]decane-8-carbaldehyde 5 (240 g, 0.141 mole) and potassium cyanide (22.05 g, 0.338 mole) were added while cooling with ice to a mixture of 4N hydrochloric acid (37 ml) and methanol (22 ml). The mixture was stirred for four days at room temperature and then, after adding water (80 ml), extracted with diethyl ether (4×100 ml). The organic phase was dried over sodium sulfate, concentrated by evaporation in vacuo, and the product was obtained as a white solid.

Yield: 25.2 g (81%) m.p. 48-51° C. $^1$H-NMR (CDCl$_3$): 1.23-2.03 (m, 9H); 2.28 (s, 6H); 3.16 (d, 1H); 3.93 (m, 4H). $^{13}$C-NMR (CDCl$_3$): 26.67 (t); 27.93 (t); 33.87 (t); 36.94 (d); 41.90 (q); 64.30 (t); 64.36 (t); 108.33 (d); 115.94 (s).

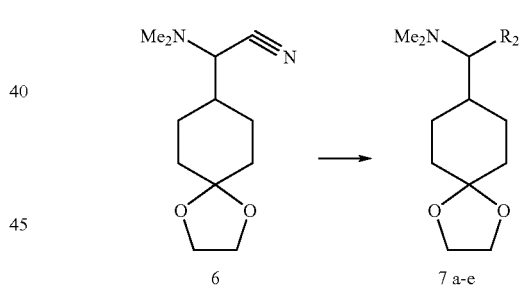

[(1,4-dioxa-spiro[4.5]dec-8-yl-4-fluorophenylmethyl]-dimethylamine 7a (R$^2$=4-fluorophenyl)

A solution of the aminonitrile 6 (19.89 g 88 mmole) in absolute THF (160 ml) was added dropwise under argon and cooling with ice to a 1M solution of 4-fluorophenyl magnesium bromide in THF (220 ml, 220 mmole) and stirred for 20 hours at RT. To work up the reaction mixture, saturated ammonium chloride solution (100 ml) and water (100 ml) were added while cooling with ice, and the mixture was extracted with diethyl ether (3×100 ml). The organic phase was washed with water and saturated sodium chloride solution, dried (Na$_2$SO$_4$) and concentrated by evaporation.

Yield: 31 g (>100%) $^{13}$C-NMR (CDCl$_3$): 26.68 (t); 28.11 (t); 34.43 (t); 34.55 (t); 37.37 (d); 41.68 (q); 64.12 (t); 73.65 (d); 108.88 (d) 114.23 (d); 114.44 (d); 130.27; 130.35; 132.43; 160.36 (s); 162.78 (s).

[(1,4-dioxa-spiro[4.5]dec-8-yl)-3-fluorophenylmethyl]-dimethylamine 7b {$R^2$=3-fluorophenyl}

A solution of the aminonitrile 6 (23.45 g, 104 mmole) in absolute THF (100 ml) was added to a 1M solution of 3-fluorophenyl magnesium bromide in THF (208 ml, 208 mmole) under argon and cooling with ice, and stirred for 20 hours at RT. To work up the reaction mixture, saturated ammonium chloride solution (100 ml) and water (100 ml) were added while cooling with ice, and the mixture was extracted with diethyl ether (3×100 ml). The organic phase was washed with water and saturated sodium chloride solution, dried, and concentrated by evaporation.

Yield: 33.33 g (99%). $^1$H-NMR (CDCl$_3$): 1.12 (m, 1H); 1.26 (m, 1H); 1.46-1.81 (m, 7H); 2.10 (s, 6H); 3.10 (d, 1H); 3.90 (m, 4H); 6.85 (m, 3H); 7.27 (m, 1H). $^{13}$C-NMR (CDCl$_3$): 26.80 (t); 28.08 (t); 34.48 (t) 34.45 (t); 34.59 (t); 37.26 (d); 41.71 (q); 64.19 (t); 74.04 (t); 108.91 (d); 113.51 (d); 113.71 (d); 115.52 (d); 115.72 (d); 124.83 (d); 128.82 (d); 128.90 (d); 139.66 (s); 161.15 (s); 163.58 (s).

[(4-chlorophenyl)-(1,4-dioxa-spiro[4.5]dec-8-yl]-dimethylamine 7c ($R^2$=4-chlorophenyl)

A solution of the aminonitrile 6 (22.43 g, 100 mmole) in absolute ether (100 ml) was added to a 1M solution of 4-chlorophenyl magnesium bromide in ether (200 ml, 200 mmole) under argon and while cooling with ice, and stirred for 20 hours at RT. To work up the reaction mixture, saturated ammonium chloride solution (100 ml) and water (100 ml) were added while cooling with ice, and the mixture was extracted with diethyl ether (3×100 ml). The organic phase was washed with water and saturated sodium chloride solution, dried, and concentrated by evaporation.

Yield: 30.9 g (100%) $^{13}$C-NMR (CDCl$_3$): 26.65 (t); 28.11 (t); 34.46 (t); 34.60 (t); 37.28 (d); 41.76 (q); 64.17 (t); 73.80 (d); 108.88 (s); 127.72 (d); 129.53 (d); 132.39 (d); 135.33 (d).

[(1,4-dioxa-spiro[4.5]dec-8-yl)-thiophen-2-yl-methyl]-dimethylamine (7d $R^2$=2-thienyl)

A solution of the aminonitrile 6 (2.24 g, 10 mmole) in absolute THF (10 ml) was added dropwise under argon and while cooling with ice to a 1M solution of thiophen-2-yl-magnesium bromide in THF (20 ml, 20 mmole), and stirred for 20 hours at RT. To work up the reaction mixture, saturated ammonium chloride solution (10 ml) and water (10 ml) were added while cooling with ice, and the mixture was extracted with diethyl ether (3×10 ml). The organic phase was washed with water and saturated sodium chloride solution, dried, and concentrated by evaporation.

Yield: 2.8 g (100%) $^{13}$C-NMR (CDCl$_3$): 27.72 (t); 27.88 (t); 34.27 (t); 39.28 (d); 41.10 (q); 64.11 (t); 68.89 (d); 108.88 (s); 123.55 (d); 125.88 (d); 127.53 (d); 139.50 (s).

[1-(1,4-dioxa-spiro[4.5]dec-8-yl)-3-phenylpropyl]-dimethylamine 7e ($R^2$=phenethyl)

A solution of the aminonitrile 6 (21.93 g, 97 mmole) in absolute THF (180 mmole) was added dropwise under argon and while cooling with ice to a 1M solution of phenylethyl magnesium chloride in THF (242 ml, 242 mmole) and stirred for 20 hours at RT. To work up the reaction mixture, saturated ammonium chloride solution (100 ml) and water (100 ml) were added while cooling with ice, and the mixture was extracted with diethyl ether (3×100 ml). The organic phase was washed with water and saturated sodium chloride solution, dried, and concentrated by evaporation.

Yield: 34 g (>100%) $^{13}$C-NMR (CDCl$_3$): 27.43 (t); 28.95 (t); 29.42 (t); 34.82 (t); 35.40 (t); 38.76 (d); 41.16 (q); 64.17 (t); 67.41 (d); 108.86 (s); 125.41 (d); 127.66 (d); 128.11 (d); 142.69 (s).

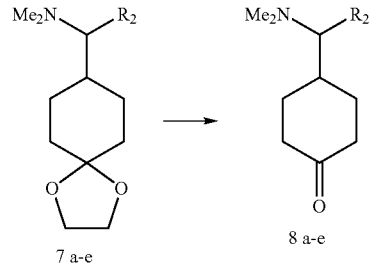

4-[dimethylamino-(4-fluorophenyl)-methyl]-cyclohexanone 8a ($R^2$=4-fluorophenyl)

The crude product of the ketal 7a (26 g, 88 mmole) was dissolved in water (40 ml), concentrated hydrochloric acid (59 ml) was added, and the whole was stirred for 20 hours at RT. The reaction mixture was extracted with diethyl ether (2×100 ml), and the aqueous phase was made alkaline with 5N NaOH while cooling with ice, extracted with dichloromethane (3×100 ml) dried, and concentrated by evaporation.

Yield: 21.36 g (98%) $^{13}$C-NMR (CDCl$_3$): 28.90 (t); 30.48 (t); 37.00 (t); 40.49 (t); 40.72 (t); 41.79 (q); 72.98 (d); 114.42 (d); 114.62 (d); 130.20 (d); 130.28 (d); 131.88 (s); 160.50 (s); 162.93 (s); 211.44 (s).

4-[dimethylamino-(3-fluorophenyl)-methyl]-cyclohexanone 8b ($R^2$=3-fluorophenyl)

The ketal 7b (30.3 g, 103 mmole) was dissolved in water (44 ml), concentrated hydrochloric acid (64 ml) was added, and the mixture was stirred for 20 hours at RT. The reaction mixture was shaken with diethyl ether (2×100 ml), and the aqueous phase was made alkaline with 5N NaOH while cooling with ice, extracted with dichloromethane (3×100 ml), dried, and concentrated by evaporation. The ketone was isolated as a colorless solid.

Yield: 22.4 g (87%) m.p.: 72-75° C. $^{13}$C-NMR (CDCl$_3$): 28.97 (t); 30.44 (t); 36.90 (t); 40.52 (t); 40.75 (t); 41.82 (q); 73.37 (d); 113.84; 114.06; 115.42; 115.62 124.71; 129.03; 129.11; 139.00; 139.06; 161.16; 163.60; 211.40 (s).

4-[(4-chlorophenyl)-dimethylaminomethyl]-cyclohexanone 8c ($R^2$=4-chlorophenyl)

The ketal 7c (30.98 g, 100 mmole) was dissolved in water (44 ml), concentrated hydrochloric acid was added (64 ml), and the mixture was stirred for 20 hours at RT. The reaction mixture was shaken with diethyl ether (2×100 ml), and the aqueous phase was made alkaline with 5N NaOH while cooling with ice, and extracted with dichloromethane (3×100 ml), dried, and concentrated by evaporation. The ketone was isolated as an oil.

Yield: 21.9 g (82%) $^{13}$C-NMR (CDCl$_3$): 28.88 (t); 30.45 (t); 36.89 (t); 40.49 (t); 40.74 (t); 41.83 (q); 73.12 (d); 127.87 (d); 130.16 (d); 132.75 (d); 134.70 (s); 211.35 (s).

4-(dimethylaminothiophen-2-yl-methyl)-cyclohexanone 8d ($R^2$=2-thienyl)

The ketal 7d (2.80 g, 10 mmole) was dissolved in water (4.4 ml), concentrated hydrochloric acid (6.4 ml) was added, and the mixture was stirred for 20 hours at RT. The reaction mixture was shaken with diethyl ether (2×10 ml), the aqueous phase was made alkaline with 5N NaOH while cooling with ice, and was extracted with dichloromethane (3×10 ml), dried, and concentrated by evaporation. The ketone was isolated as an oil.

Yield: 1.79 g (75%) $^{13}$C-NMR (CDCl$_3$): 30.02 (t); 30.18 (t); 38.84 (t); 40.29 (t); 39.28 (d); 41.17 (q); 68.24 (d); 123.88 (d); 126.01 (d); 126.34 (d); 138.77 (d); 211.49 (s).

4-(1-dimethylamino-3-phenylpropyl)-cyclohexanone 8e ($R^2$ phenethyl)

The crude product of the ketal 7e (29.6 g, 97 mmole) was dissolved in water (44 ml), concentrated hydrochloric acid (64 ml) was added, and the mixture was stirred for 20 hours at RT. The reaction mixture was shaken with diethyl ether (2×100 ml), the aqueous phase was made alkaline with 5N NaOH while cooling with ice, and was extracted with dichloromethane (3×100 ml), dried, and concentrated by evaporation. The ketone was isolated as a colorless oil.

Yield: 16.9 g (58%) $^{13}$C-NMR (CDCl$_3$): 29.40 (t); 30.02 (t); 30.97 (t); 35.34 (t); 38.71 (t); 40.79 (t); 41.01 (t); 41.23 (q); 66.65 (d); 125.66 (d); 128.12 (d); 128.19 (d); 142.27 (s); 211.70 (s).

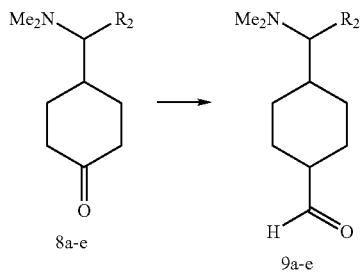

4-[dimethylamino-(4-fluorophenyl)-methyl]-cyclohexane-carbaldehyde 9a ($R^2$=4-fluorophenyl)

(Methoxymethyl)triphenylphosphonium chloride (25.7 g, 75 mmole) was suspended in absolute THF (100 ml) under argon, potassium tert-butylate (8.42 g, 75 mmole) dissolved in absolute THF (70 ml) was added dropwise at 0° C., and the mixture was then stirred for 15 minutes at 0° C. The ketone 8a (12.44 g, 50 mmole), dissolved in absolute THF (75 mmole), was then added dropwise at RT to the above solution and stirred overnight at RT. The reaction mixture was hydrolysed by adding dropwise water (38 ml) and 6N HCl (112 ml) while cooling with iced water. After stirring for one hour at RT the mixture was extracted with ether (10×50 ml), the aqueous phase was adjusted to pH 11 with 5N NaOH, was shaken with ethyl acetate (3×50 ml) dried over Na$_2$SO$_4$ and concentrated by evaporation in vacuo. The crude product was purified by flash chromatography with ethyl acetate/cyclohexane (1:1).

Yield: 9.13 g (70%) $^1$H-NMR (DMSO, 600 MHz, selected signals): δ=1.97 (s, 3H); 1.99 (s, 3H); 3.08 (d, 1H, J=9.06 Hz); 3.14 (d, 1H, J=9.82 Hz); 9.53 (s, 1H); 9.56 (s, 1H). $^{13}$C-NMR (CDCl$_3$, both diastereomers): δ=23.97; 24.21; 25.85; 26.02; 26.17; 27.35; 28.00; 29.90; 37.26; 38.34; 41.50; 41.95; 47.36; 50.55; 72.75; 75.84; 114.25; 114.45; 130.33; 130.40; 132.61; 160.41; 162.83; 204.10; 204.93.

4-[dimethylamino-(3-fluorophenyl)-methyl]-cyclohexane-carbaldehyde ($R^2$=3-fluorophenyl) 9b (Methoxymethyl)triphenylphosphonium chloride (15.42 g, 45 mmole) was suspended in absolute THF (50 ml) under argon, potassium tert-butylat (5.05 g, 45 mmole), dissolved in absolute THF (50 ml), was added dropwise at 0° C., and the mixture was then stirred for 15 minutes at 0° C. The ketone 8b (7.48 g, 0.30 mmole), dissolved in absolute THF (50 ml), was then added dropwise at RT to the above solution and the mixture was stirred overnight at RT. The mixture was hydrolysed by adding dropwise water (25 ml) and 6N HCl (75 ml) while cooling with iced water. After stirring for one hour at RT the mixture was extracted with ether (10×50 ml), the aqueous phase was adjusted to pH 11 with 5N NaOH extracted with ethyl acetate (3×50 ml) dried over Na$_2$OS$_4$, and concentrated by evaporation in vacuo. The crude product was purified by flash chromatography with ethyl acetate/cyclohexane (1:1).

Yield: 6.55 g (83%). m.p.: 40-43° C. $^1$H-NMR (DMSO, 600 MHz, selected signals): δ=1.99 (s, 3H); 2.01 (s, 3H); 3.10 (d, 1H, J=9.06 Hz); 3.18 (d, 1H, J=9.82 Hz); 9.54 (s, 1H); 9.56 (s, 1H). $^{13}$C-NMR (CDCl$_3$): 23.93; 24.12; 25.79; 25.95; 26.19; 27.19; 27.99; 29.77; 37.05; 38.16; 41.45; 41.91; 47.30; 50.49; 71.50; 74.78; 113.50; 115.37; 124.78; 128.24; 130.59; 131.24; 131.67; 139.14; 139.76; 160.06; 163.50; 204.01; 204.85.

4-[(4-chlorophenyl)-dimethylaminomethyl]-cyclohexane-carbaldehyde 9c ($R^2$=4-chlorophenyl)

(Methoxymethyl)triphenylphosphonium chloride (68.55 g, 200 mmole) was suspended in absolute THF (200 ml) under argon, potassium tert-butylate (22.44 g, 200 mmole), dissolved in absolute THF (300 ml), was added dropwise at 0° C., and the mixture was then stirred for 15 minutes at 0° C. The ketone 8c (38 g, 143 mmol), dissolved in absolute THF (200 ml), was then added at RT to the above solution and the mixture was stirred overnight at RT. The mixture was hydrolysed by adding dropwise water (150 ml) and 6N HCl (450 ml) while cooling with iced water. After stirring for one hour at RT the mixture was extracted with ether (10×100 ml), the aqueous phase was adjusted to pH 11 with 5N NaOH, shaken with ethyl acetate (3×100 ml) dried over Na$_2$SO$_4$, and concentrated by evaporation in vacuo. The crude product was purified by passage through two silica gel columns (400 g) with ethyl acetate/cyclohexane (1:1).

Yield: 32.17 g (80%). $^1$H-NMR (DMSO, 600 MHz, selected signals): δ=1.97 (s, 3H); 1.99 (s, 3H); 3.07 (d, 1H, J=9.07 Hz); 3.14 (d, 1H, J=9.82 Hz); 9.53 (s, 1H); 9.55 (s, 1H). $^{13}$C-NMR (CDCl$_3$ both diastereomers): δ=23.92; 24.16; 25.80; 25.97; 26.13; 27.25; 27.90; 29.81; 37.08; 38.19; 41.47; 41.96; 47.29; 50.48; 72.81; 74.54; 127.65; 130.28; 132.40; 134.78; 135.43; 203.98; 204.82.

4-(dimethylaminothiophen-2-yl-methyl)-cyclohexane carbaldehyde 9d ($R^2$=2-thienyl)

(Methoxymethyl)triphenylphosphonium chloride (20.56 g, 60 mmole) was suspended in absolute THF (70 ml) under argon, potassium tert-butylate (6.73 g, 60 mmole), dissolved in absolute THF (70 ml), was added dropwise at 0° C., and the mixture was then stirred for 15 minutes at 0° C. The ketone 8d (9.4 g, 40 mmole), dissolved in absolute THF (70 ml), was then added dropwise at RT to the above solution and the mixture was stirred overnight at RT. The mixture was hydrolysed by adding dropwise water (60 ml) and 6N HCl (180 ml), while cooling with iced water. After stirring for one hour at RT the mixture was extracted with ether (5×50 ml), the aqueous phase was adjusted to pH 11 with 5N NaOH, shaken with ethyl acetate (3×50 ml), dried over $Na_2SO_4$, and concentrated by evaporation in vacuo. The crude product was purified by flash chromatography with ethyl acetate/cyclohexane (1:1).

Yield: 7.66 g (77%) $^1$H-NMR (DMSO, 600 MHz, selected signals): δ=2.03 (s, 3H); 2.05 (s, 3H); 3.44 (d, 1H, J=9.82 Hz); 3.52 (d, 1H, J=10.58 Hz); 9.54 (s, 1H); 9.58 (s, 1H). $^{13}$C-NMR ($CDCl_3$, both diastereomers): δ=23.74; 23.83; 25.80; 25.84; 26.98; 27.09; 29.15; 29.68; 39.13; 40.20; 40.98; 41.29 ($N(CH_3)_2$); 47.48; 50.49; 67.81; 69.79; 123.61; 123.70; 125.89; 126.20; 126.24; 139.14; 139.48; 204.07; 204.82.

4-(1-dimethylamino-3-phenylpropyl)-cyclohexanecarbaldehyde 9e ($R^2$=phenethyl)

(Methoxymethyl)triphenylphosphonium chloride (20.56 g, 60 mmole) was suspended in absolute THF (85 ml) under argon, potassium tert-butylate (6.73 g, 60 mmole), dissolved in absolute THF (70 ml), was added dropwise at 0° C., and the mixture was then stirred for 15 minutes at 0° C. The ketone 8e (10.2 g, 40 mmole), dissolved in absolute THF (60 ml), was then added dropwise at RT to the above solution, and the mixture was stirred overnight at RT. The mixture was hydrolysed by dropwise addition of water (35 ml) and 6N HCl (90 ml) while cooling with iced water. After stirring for one hour at RT the mixture was extracted with ether (10×50 ml), the aqueous phase was adjusted to pH 11 with 5N NaOH, extracted with ethyl acetate (3×50 ml), dried over $Na_2SO_4$, and concentrated by evaporation in vacuo. The crude product was purified by flash chromatography with ethyl acetate/cyclohexane (1:1).

Yield: 6.73 g (63%). $^1$H-NMR (DMSO, 600 MHz, selected signals): δ=2.18 (s, 3H); 2.20 (s, 3H dichloromethane); 9.54 (s, 1H); 9.61 (s, 1H). $^{13}$C-NMR ($CDCl_3$, both diastereomers): δ=24.35; 24.49; 26.00; 26.09; 26.85; 27.79; 29.07; 29.13; 35.27; 39.02; 40.98; 41.19; 46.99; 50.33; 66.85; 67.85; 70.54; 71.42; 125.40; 125.44; 128.02; 128.13; 131.15; 131.17; 142.45; 204.10; 205.01.

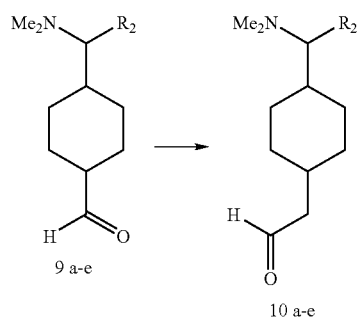

{4-[dimethylamino-(4-fluorophenyl)-methyl]-cyclohexyl}-acetaldehyde 10a ($R^2$=4-fluorophenyl)

(Methoxymethyl)triphenylphosphonium chloride (43.53 g, 127 mmole) was suspended in absolute THF (200 ml) under argon, potassium tert-butylate (14.25 g, 127 mmole), dissolved in absolute THF (130 ml), was added dropwise at 0° C., and the mixture was then stirred for 15 minutes at 0° C. The aldehyde 9a (22.3 g, 85 mmole), dissolved in absolute THF (130 ml), was then added dropwise at RT and the mixture was stirred overnight at RT. The mixture was hydrolysed by dropwise addition of water (80 ml) and 6N HCl (200 ml), while cooling with iced water. After stirring for one hour at RT the mixture was extracted 10 times with ether (each time 100 ml). The aqueous phase was adjusted to pH 11 with 5N NaOH, shaken three times with ethyl acetate (each time 100 ml), dried over $Na_2SO_4$, and concentrated by evaporation in vacuo. The crude product was purified by flash chromatography with ethyl acetate/cyclohexane (1:1).

Yield: 15.8 g (67%) $^{13}$C-NMR ($CDCl_3$, both diastereomers): δ=25.08; 25.87; 28.80; 29.10; 29.13; 29.62; 30.82; 32.90; 33.08; 36.19; 38.43; 41.36; 42.01; 47.94; 51.17; 71.11; 74.69; 114.11; 114.20; 114.32; 130.32; 130.40; 132.00; 132.92; 160.31; 162.74; 202.15; 202.23.

{4-[dimethylamino-(3-fluorophenyl)-methyl]-cyclohexyl}-acetaldehyde 10b ($R^2$=3-fluorophenyl)

(Methoxymethyl)triphenylphosphonium chloride (26.73 g, 78 mmole) was suspended in absolute THF (90 ml) under argon, potassium tert-butylate (8.75 g, 78 mmole), dissolved in absolute THF (90 ml), was added dropwise at 0° C., and the mixture was then stirred for 15 minutes at 0° C. The aldehyde 9b (13.69 g, 52 mmole), dissolved in absolute THF (90 ml), was then added dropwise at RT and the mixture was stirred overnight at RT. The mixture was hydrolysed by dropwise addition of water (50 ml) and 6N HCl (150 ml), while cooling with iced water. After stirring for one hour at RT the mixture was extracted 10 times with ether (each time 50 ml). The aqueous phase was adjusted to pH 11 with 5N NaOH, shaken three times with ethyl acetate (each time 100 ml), dried over $Na_2SO_4$ and concentrated by evaporation in vacuo. The crude product was purified by flash chromatography with ethyl acetate/cyclohexane (1:1).

Yield: 12.61 g (87%) $^{13}$C-NMR ($CDCl_3$, both diastereomers): δ=25.19; 25.83; 28.90; 29.06; 29.14; 29.68; 30.77; 32.92; 32.98; 33.10; 36.05; 38.36; 41.39; 42.04; 48.02; 51.20; 71.48; 75.07; 113.43; 113.49; 113.64; 113.69; 115.55; 115.76; 124.89; 128.70; 128.78; 128.88; 139.24; 140.08; 140.14; 161.09; 163.52; 202.19; 202.27.

{4-[(4-Chlorophenyl)-dimethylaminomethyl]-cyclohexyl}-acetaldehyde 10c ($R^2$=4-chlorophenyl)

(Methoxymethyl)triphenylphosphonium chloride (25.02 g, 73 mmole) was suspended in absolute THF (90 ml) under argon, potassium tert-butylate (8.19 g, 73 mmole), dissolved in absolute THF (90 ml), was added dropwise at 0° C., and the mixture was then stirred for 15 minutes at 0° C. The aldehyde 9c (13.86 g, 49 mmole), dissolved in absolute THF (90 ml), was then added dropwise at RT and the mixture was stirred overnight at RT. The mixture was hydrolysed by dropwise addition of water (50 ml) and 6N HCl (150 ml), while cooling with iced water. After stirring for one hour at RT the mixture was extracted 10 times with ether (each time 50 ml). The aqueous phase was adjusted to pH 11 with 5N NaOH, shaken three times with ethyl acetate (each time 100 ml), dried over $Na_2SO_4$ and concentrated by evaporation in vacuo. The crude product was purified by flash chromatography with ethyl acetate/cyclohexane (1:1).

Yield: 12.07 g (84%). $^{13}$C-NMR ($CDCl_3$, both diastereomers): δ=25.06; 25.82; 28.74; 29.00; 29.13; 29.60; 30.77; 32.87; 32.94; 33.07; 36.06; 38.32; 41.38; 42.05; 47.95; 51.17;

71.23; 74.80; 127.58; 127.66; 130.31; 132.28; 132.34; 134.81; 135.77; 202.12; 202.20.

{4-[dimethylamino-thiophen-2-yl-methyl]-cyclohexyl}-acetaldehyde 10d (R²=2-thienyl)

(Methoxymethyl)triphenylphosphonium chloride (28.79 g, 84 mmole) was suspended in absolute THF (100 ml) under argon, potassium tert-butylate (9.42 g, 84 mmole), dissolved in absolute THF (100 ml), was added dropwise at 0° C., and the mixture was then stirred for 15 minutes at 0° C. The aldehyde 9d (14.08 g, 56 mmole), dissolved in absolute THF (100 ml), was then added dropwise at RT and the mixture was stirred overnight at RT. The mixture was hydrolysed by dropwise addition of water (50 ml) and 6N HCl (150 ml), while cooling with iced water. After stirring for one hour at RT the mixture was extracted 10 times with ether (each time 50 ml). The aqueous phase was adjusted to pH 11 with 5N NaOH, shaken three times with ethyl acetate (each time 100 ml), dried over $Na_2SO_4$, and concentrated by evaporation in vacuo. The crude product was purified by flash chromatography with ethyl acetate/cyclohexane (1:2).

Yield: 11.48 g (77%). $^{13}$C-NMR (CDCl$_3$, both diastereomers): δ=25.80; 25.88; 28.73; 29.95; 30.49; 32.23; 32.76; 37.89; 40.21; 40.88; 41.23; 48.36; 51.09; 66.02; 69.97; 123.19; 123.72; 125.95; 126.31; 139.42; 139.91; 202.61.

[4-(1-dimethylamino-3-phenylpropyl)-cyclohexyl]-acetaldehyde 10e (R²=phenethyl)

(Methoxymethyl)triphenylphosphonium chloride (50.3 g, 147 mmole) was suspended in absolute THF (150 ml) under argon, potassium tert-butylate (16.5 g, 147 mmole), dissolved in absolute THF (140 ml), was added dropwise at 0° C., and the mixture was then stirred for 15 minutes at 0° C. The aldehyde 9e (27.0 g, 98 mmole), dissolved in absolute THF (150 ml), was then added dropwise at RT and the mixture was stirred overnight at RT. The mixture was hydrolysed by dropwise addition of water (102 ml) and 6N HCl (240 ml), while cooling with iced water. After stirring for one hour at RT the mixture was extracted five times with ether (each time 200 ml). The aqueous phase was adjusted to pH 11 with 5N NaOH while cooling with ice, shaken three times with ethyl acetate (each time 200 ml), dried over $Na_2SO_4$ and concentrated by evaporation in vacuo. The crude product was purified by flash chromatography with ethyl acetate/cyclohexane (1:1).

Yield: 18.1 g (64%) $^{13}$C-NMR (CDCl$_3$, both diastereomers): δ=25.55; 26.19; 29.04; 29.15; 29.35; 29.85; 31.00; 32.87; 32.68; 33.04; 35.33; 38.49; 40.86; 41.13; 47.51; 51.15; 65.48; 68.09.

Examples 9a 4-[dimethylamino-(4-fluorophenyl)-methyl]-cyclohexane carbaldehyde 9b 4-[dimethylamino-(3-fluorophenyl)-methyl]-cyclohexane carbaldehyde 9c 4-[(4-chlorophenyl)-dimethylaminomethyl]-cyclohexane carbaldehyde 9d 4-(dimethylamino-thiophen-2-yl-methyl)-cyclohexane carbaldehyde 9e 4-(1-dimethylamino-3-phenylpropyl)-cyclohexane carbaldehyde 10a {4-[dimethylamino-(4-fluorophenyl)-methyl]-cyclohexyl}-acetaldehyde 10b {4-[dimethylamino-(3-fluorophenyl)-methyl]-cyclohexyl}-acetaldehyde 10c {4-[(4-chlorophenyl)-dimethylaminomethyl]-cyclohexyl}-acetaldehyde 10d [4-(dimethylamino-thiophen-2-yl-methyl)-cyclohexyl]-acetaldehyde 10e [4-(1-dimethylamino-3-phenylpropyl)-cyclohexyl]-acetaldehyde The synthesis of the imidazoline derivatives according to the invention was carried out with the aid of the SLT106 accelerator from the company Chemspeed Ltd.

Synthesis Protocol for the Automated Synthesis

220 μmole of amine derivative (solution II, 1.1 ml, 0.2 M in methanol) were placed at room temperature in a dry 13 ml double jacket glass reactor (Chemspeed), followed by addition of 220 μmole of aldehyde derivative (solution I, 1.1 ml, 0.2 M in methanol) and 110 μmole of isonitrile derivative (solution III, 1 ml, 0.1 M in methanol). The reaction mixture was then refluxed for 10 hours. After completion of the reaction the solvent was removed. The compound was purified by HPLC. The purification was carried out via HPLC-MS. In all the specified cases the exact mass was found as M+1.

Examples

| No. | Name | Mol. wt. |
|---|---|---|
| 11. | 1-cyclohexyl-5-{4-[dimethylamino-(3-fluorophenyl)-methyl]-cyclohexyl}-4-isobutyl-4,5-dihydro-1H-imidazole-4-carboxylic acid methyl ester | 499.36 |
| 12. | 4-(4-chlorobenzyl)-1-cyclohexyl-5-{4-[dimethylamino-(3-fluorophenyl)-methyl]-cyclohexyl}-4,5-dihydro-1H-imidazole-4-carboxylic acid methyl ester | 567.30 |
| 13. | 4-butyl-1-cyclohexyl-5-{4-[dimethylamino-(3-fluorophenyl)-methyl]-cyclohexyl}-4,5-dihydro-1H-imidazole-4-carboxylic acid methyl ester | 499.36 |
| 14. | 5-{4-[(4-chlorophenyl)-dimethylaminomethyl]-cyclohexyl}-1-cyclohexyl-4-isobutyl-4,5-dihydro-1H-imidazole-4-carboxylic acid methyl ester | 515.33 |
| 15. | 4-(4-chlorobenzyl)-5-{4-[(4-chlorophenyl)-dimethylaminomethyl]-cyclohexyl}-1-cyclohexyl-4,5-dihydro-1H-imidazole-4-carboxylic acid methyl ester | 583.27 |
| 16. | 4-butyl-5-{4-[(4-chlorophenyl)-dimethylaminomethyl]-cyclohexyl}-1-cyclohexyl-4,5-dihydro-1H-imidazole-4-carboxylic acid methyl ester | 515.33 |
| 17. | 5-{4-[(4-chlorophenyl)-dimethylaminomethyl]-cyclohexylmethyl}-1-cyclohexyl-4-isobutyl-4,5-dihydro-1H-imidazole-4-carboxylic acid methyl ester | 529.34 |

-continued

| No. | Name | Mol. wt. |
|---|---|---|
| 18. | 4-(4-chlorobenzyl)-5-{4-[(4-chlorophenyl)-dimethylaminomethyl]-cyclohexylmethyl}-1-cyclohexyl-4,5-dihydro-1H-imidazole-4-carboxylic acid methyl ester | 597.29 |
| 19. | 4-butyl-5-{4-[(4-chlorophenyl)-dimethylaminomethyl]-cyclohexylmethyl}-1-cyclohexyl-4,5-dihydro-1H-imidazole-4-carboxylic acid methyl ester | 529.34 |
| 20. | 4-(4-chlorobenzyl)-1-cyclohexyl-5-[4-(dimethylamino-thiophen-2-yl-methyl)-cyclohexylmethyl]-4,5-dihydro-1H-imidazole-4-carboxylic acid methyl ester | 569.28 |
| 21. | 5-{4-[dimethylamino-(3-fluorophenyl)-methyl]-cyclohexyl}-4-isobutyl-1-propyl-4,5-dihydro-1H-imidazole-4-carboxylic acid methyl ester | 459.33 |
| 22. | 4-(4-chlorobenzyl)-5-{4-[dimethylamino-(3-fluorophenyl)-methyl]-cyclohexyl}-1-propyl-4,5-dihydro-1H-imidazole-4-carboxylic acid methyl ester | 527.27 |
| 23. | 4-butyl-5-{4-[dimethylamino-(3-fluorophenyl)-methyl]-cyclohexyl}-1-propyl-4,5-dihydro-1H-imidazole-4-carboxylic acid methyl ester | 459.33 |
| 24. | 5-{4-[(4-chlorophenyl)-dimethylaminomethyl]-cyclohexyl}-4-isobutyl-1-propyl-4,5-dihydro-1H-imidazole-4-carboxylic acid methyl ester | 475.30 |
| 25. | 4-(4-chlorobenzyl)-5-{4-[(4-chlorophenyl)-dimethylaminomethyl]-cyclohexyl}-1-propyl-4,5-dihydro-1H-imidazole-4-carboxylic acid methyl ester | 543.24 |
| 26. | 5-{4-[(4-chlorophenyl)-dimethylaminomethyl]-cyclohexylmethyl}-4-isobutyl-1-propyl-4,5-dihydro-1H-imidazole-4-carboxylic acid methyl ester | 489.31 |
| 27. | 4-(4-chlorobenzyl)-5-{4-[(4-chlorophenyl)-dimethylaminomethyl]-cyclohexylmethyl}-1-propyl-4,5-dihydro-1H-imidazole-4-carboxylic acid methyl ester | 557.26 |
| 28. | 4-butyl-5-{4-[(4-chlorophenyl)-dimethylaminomethyl]-cyclohexylmethyl}-1-propyl-4,5-dihydro-1H-imidazole-4-carboxylic acid methyl ester | 489.31 |
| 29. | 1-butyl-5-{4-[dimethylamino-(3-fluorophenyl)-methyl]-cyclohexyl}-4-isobutyl-4,5-dihydro-1H-imidazole-4-carboxylic acid methyl ester | 473.34 |
| 30. | 1-butyl-4-(4-chlorobenzyl)-5-{4-[dimethylamino-(3-fluorophenyl)-methyl]-cyclohexyl}-4,5-dihydro-1H-imidazole-4-carboxylic acid methyl ester | 541.29 |
| 31. | 1-butyl-5-{4-[(4-chlorophenyl)-dimethylaminomethyl]-cyclohexyl}-4-isobutyl-4,5-dihydro-1H-imidazole-4-carboxylic acid methyl ester | 489.31 |
| 32. | 1-butyl-4-(4-chlorobenzyl)-5-{4-[(4-chlorophenyl)-dimethylaminomethyl]-cyclohexyl}-4,5-dihydro-1H-imidazole-4-carboxylic acid methyl ester | 557.26 |
| 33. | 1,4-dibutyl-5-{4-[(4-chlorophenyl)-dimethylaminomethyl]-cyclohexyl}-4,5-dihydro-1H-imidazole-4-carboxylic acid methyl ester | 489.31 |
| 34. | 1-butyl-5-{4-[(4-chlorophenyl)-dimethylaminomethyl]-cyclohexylmethyl}-4-isobutyl-4,5-dihydro-1H-imidazole-4-carboxylic acid methyl ester | 503.33 |
| 35. | 1-butyl-4-(4-chlorobenzyl)-5-{4-[(4-chlorophenyl)-dimethylaminomethyl]-cyclohexylmethyl}-4,5-dihydro-1H-imidazole-4-carboxylic acid methyl ester | 571.27 |
| 36. | 1,4-dibutyl-5-{4-[(4-chlorophenyl)-dimethylaminomethyl]-cyclohexylmethyl}-4,5-dihydro-1H-imidazole-4-carboxylic acid methyl ester | 503.33 |
| 37. | 5-{4-[dimethylamino-(3-fluorophenyl)-methyl]-cyclohexyl}-4-isobutyl-1-phenethyl-4,5-dihydro-1H-imidazole-4-carboxylic acid methyl ester | 521.34 |
| 38. | 4-(4-chlorobenzyl)-5-{4-[dimethylamino-(3-fluorophenyl)-methyl]-cyclohexyl}-1-phenethyl-4,5-dihydro-1H-imidazole-4-carboxylic acid methyl ester | 589.29 |
| 39. | 4-butyl-5-{4-[dimethylamino-(3-fluorophenyl)-methyl]-cyclohexyl}-1-phenethyl-4,5-dihydro-1H-imidazole-4-carboxylic acid methyl ester | 521.34 |
| 40. | 5-{4-[(4-chlorophenyl)-dimethylaminomethyl]-cyclohexyl}-4-isobutyl-1-phenethyl-4,5-dihydro-1H-imidazole-4-carboxylic acid methyl ester | 537.31 |
| 41. | 4-(4-chlorobenzyl)-5-{4-[(4-chlorophenyl)-dimethylaminomethyl]-cyclohexyl}-1-phenethyl-4,5-dihydro-1H-imidazole-4-carboxylic acid methyl ester | 605.26 |
| 42. | 4-butyl-5-{4-[(4-chlorophenyl)-dimethylaminomethyl]-cyclohexyl}-1-phenethyl-4,5-dihydro-1H-imidazole-4-carboxylic acid methyl ester | 537.31 |
| 43. | 5-{4-[(4-chlorophenyl)-dimethylaminomethyl]-cyclohexylmethy}-4-isobutyl-1-phenethyl-4,5-dihydro-1H-imidazole-4-carboxylic acid methyl ester | 551.33 |
| 44. | 4-(4-chlorobenzyl)-5-{4-[(4-chlorophenyl)-dimethylaminomethyl]-cyclohexylmethyl}-1-phenethyl-4,5-dihydro-1H-imidazole-4-carboxylic acid methyl ester | 619.27 |
| 45. | 4-butyl-5-{4-[(4-chlorophenyl)-dimethylaminomethyl]-cyclohexylmethyl}-1-phenethyl-4,5-dihydro-1H-imidazole-4-carboxylic acid methyl ester | 551.33 |
| 46. | 1-benzyl-5-{4-[dimethylamino-(3-fluorophenyl)-methyl]-cyclohexyl}-4-isobutyl-4,5-dihydro-1H-imidazole-4-carboxylic acid methyl ester | 507.33 |
| 47. | 1-benzyl-4-(4-chlorobenzyl)-5-{4-[dimethylamino-(3-fluorophenyl)-methyl]-cyclohexyl}-4,5-dihydro-1H-imidazole-4-carboxylic acid methyl ester | 575.27 |
| 48. | 1-benzyl-5-{4-[(4-chlorophenyl)-dimethylaminomethyl]-cyclohexyl}-4-isobutyl-4,5-dihydro-1H-imidazole-4-carboxylic acid methyl ester | 523.30 |

-continued

| No. | Name | Mol. wt. |
|---|---|---|
| 49. | 1-benzyl-4-(4-chlorobenzyl)-5-{4-[(4-chlorophenyl)-dimethylaminomethyl]-cyclohexyl}-4,5-dihydro-1H-imidazole-4-carboxylic acid methyl ester | 591.24 |
| 50. | 1-benzyl-5-{4-[(4-chlorophenyl)-dimethylaminomethyl]-cyclohexylmethyl}-4-isobutyl-4,5-dihydro-1H-imidazole-4-carboxylic acid methyl ester | 537.31 |
| 51. | 5-{4-[(4-chlorophenyl)-dimethylaminomethyl]-cyclohexyl}-1-cyclohexyl-4-(2-methoxycarbonylethyl)-4,5-dihydro-1H-imidazole-4-carboxylic acid methyl ester | 545.30 |
| 52. | 4-benzylsulfanylmethyl-5-{4-[(4-chlorophenyl)-dimethylaminomethyl]-cyclohexyl}-1-cyclohexyl-4,5-dihydro-1H-imidazole-4-carboxylic acid methyl ester | 595.30 |
| 53. | 5-{4-[(4-chlorophenyl)-dimethylaminomethyl]-cyclohexylmethyl}-1-cyclohexyl-4-(2-methoxycarbonylethyl)-4,5-dihydro-1H-imidazole-4-carboxylic acid methyl ester | 559.32 |
| 54. | Methyl-4-sec-butyl-5-((4-((4-chlorophenyl)(dimethylamino)methyl)cyclohexyl)methyl)-1-cyclohexyl-4,5-dihydro-1H-imidazole-4-carboxylate | 529.34 |
| 55. | 5-{4-[(4-chlorophenyl)-dimethylaminomethyl]-cyclohexylmethyl}-1-cyclohexyl-4-methylsulfanylmethyl-4,5-dihydro-1H-imidazole-4-carboxylic acid methyl ester | 533.28 |
| 56. | 4-benzylsulfanylmethyl-5-{4-[(4-chlorophenyl)-dimethylaminomethyl]-cyclohexylmethyl}-1-cyclohexyl-4,5-dihydro-1H-imidazole-4-carboxylic acid methyl ester | 609.32 |
| 57. | 5-{4-[dimethylamino-(3-fluorophenyl)-methyl]-cyclohexyl}-4-methylsulfanylmethyl-1-propyl-4,5-dihydro-1H-imidazole-4-carboxylic acid methyl ester | 463.27 |
| 58. | 4-benzylsulfanylmethyl-5-{4-[dimethylamino-(3-fluorophenyl)-methyl]-cyclohexyl}-1-propyl-4,5-dihydro-1H-imidazole-4-carboxylic acid methyl ester | 539.30 |
| 59. | 5-{4-[(4-chlorophenyl)-dimethylaminomethyl]-cyclohexyl}-4-(2-methoxycarbonylethyl)-1-propyl-4,5-dihydro-1H-imidazole-4-carboxylic acid methyl ester | 505.27 |
| 60. | 4-benzylsulfanylmethyl-5-{4-[(4-chlorophenyl)-dimethylaminomethyl]-cyclohexyl}-1-propyl-4,5-dihydro-1H-imidazole-4-carboxylic acid methyl ester | 555.27 |
| 61. | 5-{4-[(4-chlorophenyl)-dimethylaminomethyl]-cyclohexylmethyl}-4-(2-methoxycarbonylethyl)-1-propyl-4,5-dihydro-1H-imidazole-4-carboxylic acid methyl ester | 519.29 |
| 62. | 4-sec-butyl-5-{4-[(4-chlorophenyl)-dimethylaminomethyl]-cyclohexylmethyl}-1-propyl-4,5-dihydro-1H-imidazole-4-carboxylic acid methyl ester | 489.31 |
| 63. | 5-{4-[(4-chlorophenyl)-dimethylaminomethyl]-cyclohexylmethyl}-4-methylsulfanylmethyl-1-propyl-4,5-dihydro-1H-imidazole-4-carboxylic acid methyl ester | 493.25 |
| 64. | 4-benzylsulfanylmethyl-5-{4-[(4-chlorophenyl)-dimethylaminomethyl]-cyclohexylmethyl}-1-propyl-4,5-dihydro-1H-imidazole-4-carboxylic acid methyl ester | 569.28 |
| 65. | 1-butyl-5-{4-[dimethylamino-(3-fluorophenyl)-methyl]-cyclohexyl}-4-(2-methoxycarbonylethyl)-4,5-dihydro-1H-imidazole-4-carboxylic acid methyl ester | 503.32 |
| 66. | 1-butyl-5-{4-[dimethylamino-(3-fluorophenyl)-methyl]-cyclohexyl}-4-methylsulfanylmethyl-4,5-dihydro-1H-imidazole-4-carboxylic acid methyl ester | 477.28 |
| 67. | 4-benzylsulfanylmethyl-1-butyl-5-{4-[dimethylamino-(3-fluorophenyl)-methyl]-cyclohexyl}-4,5-dihydro-1H-imidazole-4-carboxylic acid methyl ester | 553.31 |
| 68. | 1-butyl-5-{4-[(4-chlorophenyl)-dimethylaminomethyl]-cyclohexyl}-4-(2-methoxycarbonylethyl)-4,5-dihydro-1H-imidazole-4-carboxylic acid methyl ester | 519.29 |
| 69. | 4-benzylsulfanylmethyl-1-butyl-5-{4-[(4-chlorophenyl)-dimethylaminomethyl]-cyclohexyl}-4,5-dihydro-1H-imidazole-4-carboxylic acid methyl ester | 569.28 |
| 70. | 1-butyl-5-{4-[(4-chlorophenyl)-dimethylaminomethyl]-cyclohexylmethyl}-4-(2-methoxycarbonylethyl)-4,5-dihydro-1H-imidazole-4-carboxylic acid methyl ester | 533.30 |
| 71. | 5-[4-(1-dimethylamino-3-phenylpropyl)-cyclohexylmethyl]-4-(2-methoxycarbonylethyl)-1-propyl-4,5-dihydro-1H-imidazole-4-carboxylic acid methyl ester | 513.36 |
| 72. | 1-butyl-5-{4-[dimethylamino-(3-fluorophenyl)-methyl]-cyclohexylmethyl}-4-(2-methoxycarbonylethyl)-4,5-dihydro-1H-imidazole-4-carboxylic acid methyl ester | 517.33 |
| 73. | 1-butyl-4-sec-butyl-5-{4-[dimethylamino-(3-fluorophenyl)-methyl]-cyclohexylmethyl}-4,5-dihydro-1H-imidazole-4-carboxylic acid methyl ester | 487.36 |

-continued

| No. | Name | Mol. wt. |
|---|---|---|
| 74. | 1-butyl-5-{4-[dimethylamino-(3-fluorophenyl)-methyl]-cyclohexylmethyl}-4-methylsulfanylmethyl-4,5-dihydro-1H-imidazole-4-carboxylic acid methyl ester | 491.30 |
| 75. | 4-benzylsulfanylmethyl-1-butyl-5-{4-[dimethylamino-(3-fluorophenyl)-methyl]-cyclohexylmethyl}-4,5-dihydro-1H-imidazole-4-carboxylic acid methyl ester | 567.33 |
| 76. | 1-butyl-5-{4-[dimethylamino-(4-fluorophenyl)-methyl]-cyclohexylmethyl}-4-(2-methoxycarbonylethyl)-4,5-dihydro-1H-imidazole-4-carboxylic acid methyl ester | 517.33 |
| 77. | 1-butyl-5-{4-[dimethylamino-(4-fluorophenyl)-methyl]-cyclohexylmethyl}-4-methylsulfanylmethyl-4,5-dihydro-1H-imidazole-4-carboxylic acid methyl ester | 491.30 |
| 78. | 1-butyl-5-[4-(1-dimethylamino-3-phenylpropyl)-cyclohexylmethyl]-4-(2-methoxycarbonylethyl)-4,5-dihydro-1H-imidazole-4-carboxylic acid methyl ester | 527.37 |
| 79. | 4-benzylsulfanylmethyl-1-butyl-5-[4-(1-dimethylamino-3-phenylpropyl)-cyclohexylmethyl]-4,5-dihydro-1H-imidazole-4-carboxylic acid methyl ester | 577.37 |
| 80. | 5-{4-[dimethylamino-(3-fluorophenyl)-methyl]-cyclohexylmethyl}-4-(2-methoxycarbonylethyl)-1-phenethyl-4,5-dihydro-1H-imidazole-4-carboxylic acid methyl ester | 565.33 |
| 81. | 4-sec-butyl-5-{4-[dimethylamino-(3-fluorophenyl)-methyl]-cyclohexylmethyl}-1-phenethyl-4,5-dihydro-1H-imidazole-4-carboxylic acid methyl ester | 535.36 |
| 82. | 4-benzylsulfanylmethyl-5-{4-[dimethylamino-(3-fluorophenyl)-methyl]-cyclohexylmethyl}-1-phenethyl-4,5-dihydro-1H-imidazole-4-carboxylic acid methyl ester | 615.33 |
| 83. | 5-{4-[dimethylamino-(4-fluorophenyl)-methyl]-cyclohexylmethyl}-4-(2-methoxycarbonylethyl)-1-phenethyl-4,5-dihydro-1H-imidazole-4-carboxylic acid methyl ester | 565.33 |
| 84. | 5-[4-(1-dimethylamino-3-phenylpropyl)-cyclohexylmethyl]-4-(2-methoxycarbonylethyl)-1-phenethyl-4,5-dihydro-1H-imidazole-4-carboxylic acid methyl ester | 575.37 |
| 85. | 1-benzyl-5-{4-[dimethylamino-(3-fluorophenyl)-methyl]-cyclohexylmethyl}-4-(2-methoxycarbonylethyl)-4,5-dihydro-1H-imidazole-4-carboxylic acid methyl ester | 551.32 |
| 86. | 1-benzyl-4-benzylsulfanylmethyl-5-{4-[dimethylamino-(3-fluorophenyl)-methyl]-cyclohexylmethyl}-4,5-dihydro-1H-imidazole-4-carboxylic acid methyl ester | 601.31 |
| 87. | 1-benzyl-5-{4-[dimethylamino-(4-fluorophenyl)-methyl]-cyclohexylmethyl}-4-(2-methoxycarbonylethyl)-4,5-dihydro-1H-imidazole-4-carboxylic acid methyl ester | 551.32 |
| 88. | 1-butyl-4-sec-butyl-5-{4-[(4-chlorophenyl)-dimethylaminomethyl]-cyclohexylmethyl}-4,5-dihydro-1H-imidazole-4-carboxylic acid methyl ester | 503.33 |
| 89. | 1-butyl-5-{4-[(4-chlorophenyl)-dimethylaminomethyl]-cyclohexylmethyl}-4-methylsulfanylmethyl-4,5-dihydro-1H-imidazole-4-carboxylic acid methyl ester | 507.27 |
| 90. | 4-benzylsulfanylmethyl-1-butyl-5-{4-[(4-chlorophenyl)-dimethylaminomethyl]-cyclohexylmethyl}-4,5-dihydro-1H-imidazole-4-carboxylic acid methyl ester | 583.30 |
| 91. | 5-{4-[dimethylamino-(3-fluorophenyl)-methyl]-cyclohexyl}-4-(2-methoxycarbonylethyl)-1-phenethyl-4,5-dihydro-1H-imidazole-4-carboxylic acid methyl ester | 551.32 |
| 92. | 4-benzylsulfanylmethyl-5-{4-[dimethylamino-(3-fluorophenyl)-methyl]-cyclohexyl}-1-phenethyl-4,5-dihydro-1H-imidazole-4-carboxylic acid methyl ester | 601.31 |
| 93. | 4-benzylsulfanylmethyl-5-{4-[(4-chlorophenyl)-dimethylaminomethyl]-cyclohexyl}-1-phenethyl-4,5-dihydro-1H-imidazole-4-carboxylic acid methyl ester | 617.28 |
| 94. | 5-{4-[(4-chlorophenyl)-dimethylaminomethyl]-cyclohexylmethyl}-4-(2-methoxycarbonylethyl)-1-phenethyl-4,5-dihydro-1H-imidazole-4-carboxylic acid methyl ester | 581.30 |
| 95. | 1-benzyl-5-{4-[dimethylamino-(3-fluorophenyl)-methyl]-cyclohexyl}-4-(2-methoxycarbonylethyl)-4,5-dihydro-1H-imidazole-4-carboxylic acid methyl ester | 537.30 |
| 96. | 1-benzyl-5-{4-[dimethylamino-(3-fluorophenyl)-methyl]-cyclohexyl}-4-methylsulfanylmethyl-4,5-dihydro-1H-imidazole-4-carboxylic acid methyl ester | 511.27 |
| 97. | 1-benzyl-4-benzylsulfanylmethyl-5-{4-[dimethylamino-(3-fluorophenyl)-methyl]-cyclohexyl}-4,5-dihydro-1H-imidazole-4-carboxylic acid methyl ester | 587.30 |
| 98. | 1-benzyl-4-benzylsulfanylmethyl-5-{4-[(4-chlorophenyl)-dimethylaminomethyl]-cyclohexyl}-4,5-dihydro-1H-imidazole-4-carboxylic acid methyl ester | 603.27 |

-continued

| No. | Name | Mol. wt. |
|---|---|---|
| 99. | 1-benzyl-5-{4-[(4-chlorophenyl)-dimethylaminomethyl]-cyclohexylmethyl}-4-(2-methoxycarbonylethyl)-4,5-dihydro-1H-imidazole-4-carboxylic acid methyl ester | 567.29 |
| 100. | 1-benzyl-5-{4-[(4-chlorophenyl)-dimethylaminomethyl]-cyclohexylmethyl}-4-methylsulfanylmethyl-4,5-dihydro-1H-imidazole-4-carboxylic acid methyl ester | 541.25 |
| 101. | 1-benzyl-4-benzylsulfanylmethyl-5-{4-[(4-chlorophenyl)-dimethylaminomethyl]-cyclohexylmethyl}-4,5-dihydro-1H-imidazole-4-carboxylic acid methyl ester | 617.28 |
| 102. | 1-cyclohexyl-5-{4-[dimethylamino-(3-fluorophenyl)-methyl]-cyclohexylmethyl}-4-propyl-4,5-dihydro-1H-imidazole-4-carboxylic acid methyl ester | 499.36 |
| 103. | 1-cyclohexyl-5-{4-[dimethylamino-(3-fluorophenyl)-methyl]-cyclohexylmethyl}-4-(2-methylsulfanyl-ethyl)-4,5-dihydro-1H-imidazole-4-carboxylic acid methyl ester | 531.33 |
| 104. | 1-cyclohexyl-5-{4-[dimethylamino-(3-fluorophenyl)-methyl]-cyclohexylmethyl}-4-methyl-4,5-dihydro-1H-imidazole-4-carboxylic acid methyl ester | 471.33 |
| 105. | 1-cyclohexyl-5-{4-[dimethylamino-(4-fluorophenyl)-methyl]-cyclohexylmethyl}-4-propyl-4,5-dihydro-1H-imidazole-4-carboxylic acid methyl ester | 499.36 |
| 106. | 1-cyclohexyl-5-{4-[dimethylamino-(4-fluorophenyl)-methyl]-cyclohexylmethyl}-4-(2-methylsulfanyl-ethyl)-4,5-dihydro-1H-imidazole-4-carboxylic acid methyl ester | 531.33 |
| 107. | 1-cyclohexyl-5-{4-[dimethylamino-(4-fluorophenyl)-methyl]-cyclohexylmethyl}-4-methyl-4,5-dihydro-1H-imidazole-4-carboxylic acid methyl ester | 471.33 |
| 108. | 1-cyclohexyl-5-[4-(1-dimethylamino-3-phenylpropyl)-cyclohexylmethyl]-4-propyl-4,5-dihydro-1H-imidazole-4-carboxylic acid methyl ester | 509.40 |
| 109. | 1-cyclohexyl-5-[4-(1-dimethylamino-3-phenylpropyl)-cyclohexylmethyl]-4-(2-methylsulfanyl-ethyl)-4,5-dihydro-1H-imidazole-4-carboxylic acid methyl ester | 541.37 |
| 110. | 1-cyclohexyl-5-[4-(1-dimethylamino-3-phenylpropyl)-cyclohexylmethyl]-4-methyl-4,5-dihydro-1H-imidazole-4-carboxylic acid methyl ester | 481.37 |
| 111. | 5-{4-[dimethylamino-(3-fluorophenyl)-methyl]-cyclohexylmethyl}-1,4-dipropyl-4,5-dihydro-1H-imidazole-4-carboxylic acid methyl ester | 459.33 |
| 112. | 5-{4-[dimethylamino-(3-fluorophenyl)-methyl]-cyclohexylmethyl}-4-(2-methylsulfanyl-ethyl)-1-propyl-4,5-dihydro-1H-imidazole-4-carboxylic acid methyl ester | 491.30 |
| 113. | 1-benzyl-4-(4-chlorobenzyl)-5-{4-[(4-chlorophenyl)-dimethylaminomethyl]-cyclohexylmethyl}-4,5-dihydro-1H-imidazole-4-carboxylic acid methyl ester | 605.26 |
| 114. | 1-benzyl-4-butyl-5-{4-[(4-chlorophenyl)-dimethylaminomethyl]-cyclohexylmethyl}-4,5-dihydro-1H-imidazole-4-carboxylic acid methyl ester | 537.31 |
| 115. | 1-cyclohexyl-5-{4-[dimethylamino-(3-fluorophenyl)-methyl]-cyclohexyl}-4-(2-methoxycarbonylethyl)-4,5-dihydro-1H-imidazole-4-carboxylic acid methyl ester | 529.33 |
| 116. | 4-benzylsulfanylmethyl-1-cyclohexyl-5-{4-[dimethylamino-(3-fluorophenyl)-methyl]-cyclohexyl}-4,5-dihydro-1H-imidazole-4-carboxylic acid methyl ester | 579.33 |
| 117. | 5-{4-[dimethylamino-(3-fluorophenyl)-methyl]-cyclohexylmethyl}-4-methyl-1-propyl-4,5-dihydro-1H-imidazole-4-carboxylic acid methyl ester | 431.29 |
| 118. | 5-{4-[dimethylamino-(4-fluorophenyl)-methyl]-cyclohexylmethyl}-1,4-dipropyl-4,5-dihydro-1H-imidazole-4-carboxylic acid methyl ester | 459.33 |
| 119. | 5-{4-[dimethylamino-(4-fluorophenyl)-methyl]-cyclohexylmethyl}-4-(2-methylsulfanylethyl)-1-propyl-4,5-dihydro-1H-imidazole-4-carboxylic acid methyl ester | 491.30 |
| 120. | 5-[4-(1-dimethylamino-3-phenylpropyl)-cyclohexylmethyl]-1,4-dipropyl-4,5-dihydro-1H-imidazole-imidazole-4-carboxylic acid methyl ester | 469.37 |
| 121. | 5-[4-(1-dimethylamino-3-phenylpropyl)-cyclohexylmethyl]-4-(2-methylsulfanylethyl)-1-propyl-4,5-dihydro-1H-imidazole-4-carboxylic acid methyl ester | 501.34 |
| 122. | 1-butyl-5-{4-[dimethylamino-(3-fluorophenyl)-methyl]-cyclohexylmethyl}-4-propyl-4,5-dihydro-1H-imidazole-4-carboxylic acid methyl ester | 473.34 |
| 123. | 1-butyl-5-{4-[dimethylamino-(3-fluorophenyl)-methyl]-cyclohexylmethyl}-4-(2-methylsulfanylethyl)-4,5-dihydro-1H-imidazole-4-carboxylic acid methyl ester | 505.31 |
| 124. | 1-butyl-5-{4-[dimethylamino-(3-fluorophenyl)-methyl]-cyclohexylmethyl}-4-methyl-4,5-dihydro-1H-imidazole-4-carboxylic acid methyl ester | 445.31 |
| 125. | 1-butyl-5-{4-[dimethylamino-(4-fluorophenyl)-methyl]-cyclohexylmethyl}-4-propyl-4,5-dihydro-1H-imidazole-4-carboxylic acid methyl ester | 473.34 |
| 126. | 1-butyl-5-{4-[dimethylamino-(4-fluorophenyl)-methyl]-cyclohexylmethyl}-4-(2-methylsulfanyl-ethyl)-4,5-dihydro-1H-imidazole-4-carboxylic acid methyl ester | 505.31 |

-continued

| No. | Name | Mol. wt. |
|---|---|---|
| 127. | 1-butyl-5-[4-(1-dimethylamino-3-phenylpropyl)-cyclohexylmethyl]-4-propyl-4,5-dihydro-1H-imidazole-4-carboxylic acid methyl ester | 483.38 |
| 128. | 1-butyl-5-[4-(1-dimethylamino-3-phenylpropyl)-cyclohexylmethyl]-4-(2-methylsulfanylethyl)-4,5-dihydro-1H-imidazole-4-carboxylic acid methyl ester | 515.35 |
| 129. | 5-{4-[dimethylamino-(3-fluorophenyl)-methyl]-cyclohexylmethyl}-1-phenethyl-4-propyl-4,5-dihydro-1H-imidazole-4-carboxylic acid methyl ester | 521.34 |
| 130. | 5-{4-[dimethylamino-(3-fluorophenyl)-methyl]-cyclohexylmethyl}-4-(2-methylsulfanylethyl)-1-phenethyl-4,5-dihydro-1H-imidazole-4-carboxylic acid methyl ester | 553.31 |
| 131. | 5-{4-[dimethylamino-(3-fluorophenyl)-methyl]-cyclohexylmethyl}-4-methyl-1-phenethyl-4,5-dihydro-1H-imidazole-4-carboxylic acid methyl ester | 493.31 |
| 132. | 5-{4-[dimethylamino-(4-fluorophenyl)-methyl]-cyclohexylmethyl}-1-phenethyl-4-propyl-4,5-dihydro-1H-imidazole-4-carboxylic acid methyl ester | 521.34 |
| 133. | 5-{4-[dimethylamino-(4-fluorophenyl)-methyl]-cyclohexylmethyl}-4-(2-methylsulfanylethyl)-1-phenethyl-4,5-dihydro-1H-imidazole-4-carboxylic acid methyl ester | 553.31 |
| 134. | 5-{4-[dimethylamino-(4-fluorophenyl)-methyl]-cyclohexylmethyl}-4-methyl-1-phenethyl-4,5-dihydro-1H-imidazole-4-carboxylic acid methyl ester | 493.31 |
| 135. | 5-[4-(1-dimethylamino-3-phenylpropyl)-cyclohexylmethyl]-1-phenethyl-4-propyl-4,5-dihydro-1H-imidazole-4-carboxylic acid methyl ester | 531.38 |
| 136. | 5-[4-(1-dimethylamino-3-phenylpropyl)-cyclohexylmethyl]-4-(2-methylsulfanylethyl)-1-phenethyl-4,5-dihydro-1H-imidazole-4-carboxylic acid methyl ester | 563.35 |
| 137. | 5-[4-(1-dimethylamino-3-phenylpropyl)-cyclohexylmethyl]-4-methyl-1-phenethyl-4,5-dihydro-1H-imidazole-4-carboxylic acid methyl ester | 503.35 |
| 138. | 1-benzyl-5-{4-[dimethylamino-(3-fluorophenyl)-methyl]-cyclohexylmethyl}-4-propyl-4,5-dihydro-1H-imidazole-4-carboxylic acid methyl ester | 507.33 |
| 139. | 1-benzyl-5-{4-[dimethylamino-(3-fluorophenyl)-methyl]-cyclohexylmethyl}-4-(2-methylsulfanyl-ethyl)-4,5-dihydro-1H-imidazole-4-carboxylic acid methyl ester | 539.30 |
| 140. | 1-benzyl-5-{4-[dimethylamino-(3-fluorophenyl)-methyl]-cyclohexylmethyl}-4-methyl-4,5-dihydro-1H-imidazole-4-carboxylic acid methyl ester | 479.29 |
| 141. | 1-benzyl-5-{4-[dimethylamino-(4-fluorophenyl)-methyl]-cyclohexylmethyl}-4-propyl-4,5-dihydro-1H-imidazole-4-carboxylic acid methyl ester | 507.33 |
| 142. | 1-benzyl-5-{4-[dimethylamino-(4-fluorophenyl)-methyl]-cyclohexylmethyl}-4-(2-methylsulfanyl-ethyl)-4,5-dihydro-1H-imidazole-4-carboxylic acid methyl ester | 539.30 |
| 143. | 1-benzyl-5-{4-[dimethylamino-(4-fluorophenyl)-methyl]-cyclohexylmethyl}-4-methyl-4,5-dihydro-1H-imidazole-4-carboxylic acid methyl ester | 479.29 |
| 144. | 1-benzyl-5-[4-(1-dimethylamino-3-phenylpropyl)-cyclohexylmethyl]-4-propyl-4,5-dihydro-1H-imidazole-4-carboxylic acid methyl ester | 517.37 |
| 145. | 1-benzyl-5-[4-(1-dimethylamino-3-phenylpropyl)-cyclohexylmethyl]-4-(2-methylsulfanyl-ethyl)-4,5-dihydro-1H-imidazole-4-carboxylic acid methyl ester | 549.34 |
| 146. | 1-benzyl-5-[4-(1-dimethylamino-3-phenylpropyl)-cyclohexylmethyl]-4-methyl-4,5-dihydro-1H-imidazole-4-carboxylic acid methyl ester | 489.34 |
| 147. | 1-cyclohexyl-5-{4-[dimethylamino-(3-fluorophenyl)-methyl]-cyclohexylmethyl}-4-(2-methoxycarbonylethyl)-4,5-dihydro-1H-imidazole-4-carboxylic acid methyl ester | 543.35 |
| 148. | 4-sec-butyl-1-cyclohexyl-5-{4-[dimethylamino-(3-fluorophenyl)-methyl]-cyclohexylmethyl}-4,5-dihydro-1H-imidazole-4-carboxylic acid methyl ester | 513.37 |
| 149. | 1-cyclohexyl-5-{4-[dimethylamino-(3-fluorophenyl)-methyl]-cyclohexylmethyl}-4-methylsulfanylmethyl-4,5-dihydro-1H-imidazole-4-carboxylic acid methyl ester | 517.31 |
| 150. | 4-benzylsulfanylmethyl-1-cyclohexyl-5-{4-[dimethylamino-(3-fluorophenyl)-methyl]-cyclohexylmethyl}-4,5-dihydro-1H-imidazole-4-carboxylic acid methyl ester | 593.35 |

-continued

| No. | Name | Mol. wt. |
|---|---|---|
| 151. | 1-cyclohexyl-5-{4-[dimethylamino-(4-fluorophenyl)-methyl]-cyclohexylmethyl}-4-(2-methoxycarbonylethyl)-4,5-dihydro-1H-imidazole-4-carboxylic acid methyl ester | 543.35 |
| 152. | 4-sec-butyl-1-cyclohexyl-5-{4-[dimethylamino-(4-fluorophenyl)-methyl]-cyclohexylmethyl}-4,5-dihydro-1H-imidazole-4-carboxylic acid methyl ester | 513.37 |
| 153. | 1-cyclohexyl-5-{4-[dimethylamino-(4-fluorophenyl)-methyl]-cyclohexylmethyl}-4-methylsulfanylmethyl-4,5-dihydro-1H-imidazole-4-carboxylic acid methyl ester | 517.31 |
| 154. | 1-cyclohexyl-5-[4-(1-dimethylamino-3-phenylpropyl)-cyclohexylmethyl]-4-(2-methoxycarbonylethyl)-4,5-dihydro-1H-imidazole-4-carboxylic acid methyl ester | 553.39 |
| 155. | 1-cyclohexyl-5-[4-(1-dimethylamino-3-phenylpropyl)-cyclohexylmethyl]-4-methylsulfanylmethyl-4,5-dihydro-1H-imidazole-4-carboxylic acid methyl ester | 527.35 |
| 156. | 4-benzylsulfanylmethyl-1-cyclohexyl-5-[4-(1-dimethylamino-3-phenylpropyl)-cyclohexylmethyl]-4,5-dihydro-1H-imidazole-4-carboxylic acid methyl ester | 603.39 |
| 157. | 5-{4-[dimethylamino-(3-fluorophenyl)-methyl]-cyclohexylmethyl}-4-(2-methoxycarbonylethyl)-1-propyl-4,5-dihydro-1H-imidazole-4-carboxylic acid methyl ester | 503.32 |
| 158. | 5-{4-[dimethylamino-(3-fluorophenyl)-methyl]-cyclohexylmethyl}-4-methylsulfanylmethyl-1-propyl-4,5-dihydro-1H-imidazole-4-carboxylic acid methyl ester | 477.28 |
| 159. | 5-{4-[dimethylamino-(4-fluorophenyl)-methyl]-cyclohexylmethyl}-4-(2-methoxycarbonylethyl)-1-propyl-4,5-dihydro-1H-imidazole-4-carboxylic acid methyl ester | 503.32 |
| 160. | 5-{4-[dimethylamino-(4-fluorophenyl)-methyl]-cyclohexylmethyl}-4-methylsulfanylmethyl-1-propyl-4,5-dihydro-1H-imidazole-4-carboxylic acid methyl ester | 477.28 |
| 161. | 4-benzylsulfanylmethyl-5-{4-[dimethylamino-(4-fluorophenyl)-methyl]-cyclohexylmethyl}-1-propyl-4,5-dihydro-1H-imidazole-4-carboxylic acid methyl ester | 553.31 |

Investigations on the Efficacy of the Compounds According to the Invention

Method for Determining the Affinity for the Human μ-Opiate Receptor

The receptor affinity for the human μ-opiate receptor is determined in a homogeneous batch in microtiter plates. For this purpose dilution series of the substances to be tested are incubated with a receptor membrane preparation (15-40 μg protein/250 μl incubation batch) of CHO-K1 cells, which express the human μ-opiate receptor (RB-HOM receptor membrane preparation from PerkinElmer Life Sciences, Zaventem, Belgium), in the presence of 1 nmole/l of the radioactive ligand [$^3$H]-naloxone (NET719, PerkinElmer Life Sciences company, Zaventem, Belgium) and 1 mg WGA-SPA beads (wheat germ agglutinin SPA beads from Amersham/Pharmacia, Freiburg, Germany) in a total volume of 250 μl for 90 minutes at room temperature. 50 mmole/l of Tris-HCl supplemented with 0.06% bovine serum albumin is used as incubation buffer. In order to determine the non-specific binding, 100 μmole/l of naloxone is additionally added. After the end of the 90 minutes' incubation time the microtiter plates are centrifuged for 20 minutes at 1000 g and the radioactivity is measured in a beta counter (Microbeta-Trilux, PerkinElmer Wallac, Freiburg, Germany). The percentage displacement of the radioactive ligand from its binding to the human μ-opiate receptor at a concentration of the test substances of 1 μmole/l is determined and is given as percentage inhibition of the specific binding.

TABLE 1

μ Affinities of selected aldehydes

| No. | μ-Opioid receptor, % inhibition [1 μM] |
|---|---|
| 9c | 45 |
| 10c | 50 |
| 10b | 67 |
| 9d | 69 |
| 10d | 79 |

TABLE 2
μ Affinities of Examples 11-161:
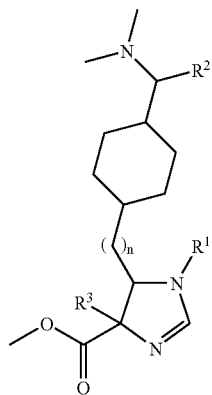
| No. | n | R¹ | R² | R³ | μ-Opioid receptor, % inhibition [1 μM] |
|---|---|---|---|---|---|
| 11 | 0 | cyclohexyl | 3-F-phenyl | isobutyl | 84 |
| 12 | 0 | cyclohexyl | 3-F-phenyl | 4-Cl-benzyl | 73 |
| 13 | 0 | cyclohexyl | 3-F-phenyl | n-pentyl | 94 |
| 14 | 0 | cyclohexyl | 4-Cl-phenyl | isobutyl | 92 |
| 15 | 0 | cyclohexyl | 4-Cl-phenyl | 4-Cl-benzyl | 76 |
| 16 | 0 | cyclohexyl | 4-Cl-phenyl | n-pentyl | 92 |

TABLE 2-continued

μ Affinities of Examples 11-161:

| No. | n | R¹ | R² | R³ | μ-Opioid receptor, % inhibition [1 μM] |
|---|---|---|---|---|---|
| 17 | 1 | cyclohexyl | 4-Cl-phenyl | isobutyl | 96 |
| 18 | 1 | cyclohexyl | 4-Cl-phenyl | 4-Cl-benzyl | 90 |
| 19 | 1 | cyclohexyl | 4-Cl-phenyl | n-pentyl | 96 |
| 20 | 1 | cyclohexyl | 2-thienyl | 4-Cl-benzyl | 95 |
| 21 | 0 | n-propyl | 3-F-phenyl | isobutyl | 83 |
| 22 | 0 | n-propyl | 3-F-phenyl | 4-Cl-benzyl | 88 |

TABLE 2-continued
μ Affinities of Examples 11-161:
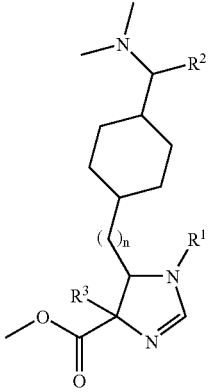
| No. | n | R¹ | R² | R³ | μ-Opioid receptor, % inhibition [1 μM] |
|-----|---|----|----|----|----------------------------------------|
| 23 | 0 | propyl | 3-F-phenyl | pentyl | 76 |
| 24 | 0 | propyl | 4-Cl-phenyl | isopentyl | 89 |
| 25 | 0 | propyl | 4-Cl-phenyl | 4-Cl-benzyl | 83 |
| 26 | 1 | propyl | 4-Cl-phenyl | isopentyl | 96 |
| 27 | 1 | propyl | 4-Cl-phenyl | 4-Cl-benzyl | 96 |
| 28 | 1 | propyl | 4-Cl-phenyl | pentyl | 97 |

TABLE 2-continued

μ Affinities of Examples 11-161:

| No. | n | R¹ | R² | R³ | μ-Opioid receptor, % inhibition [1 μM] |
|---|---|---|---|---|---|
| 29 | 0 | n-pentyl | 3-fluorophenyl | isobutyl | 89 |
| 30 | 0 | n-pentyl | 3-fluorophenyl | 4-chlorobenzyl | 89 |
| 31 | 0 | n-pentyl | 4-chlorophenyl | isobutyl | 91 |
| 32 | 0 | n-pentyl | 4-chlorophenyl | 4-chlorobenzyl | 74 |
| 33 | 0 | n-pentyl | 4-chlorophenyl | n-pentyl | 85 |
| 34 | 1 | n-pentyl | 4-chlorophenyl | isobutyl | 98 |
| 35 | 1 | n-pentyl | 4-chlorophenyl | 4-chlorobenzyl | 92 |

TABLE 2-continued

μ Affinities of Examples 11-161:

| No. | n | R¹ | R² | R³ | μ-Opioid receptor, % inhibition [1 μM] |
|---|---|---|---|---|---|
| 36 | 1 | pentyl | 4-chlorophenyl | pentyl | 97 |
| 37 | 0 | 2-phenylethyl | 3-fluorophenyl | isobutyl | 93 |
| 38 | 0 | 2-phenylethyl | 3-fluorophenyl | 4-chlorobenzyl | 84 |
| 39 | 0 | 2-phenylethyl | 3-fluorophenyl | pentyl | 88 |
| 40 | 0 | 2-phenylethyl | 4-chlorophenyl | isobutyl | 95 |
| 41 | 0 | 2-phenylethyl | 4-chlorophenyl | 4-chlorobenzyl | 79 |

TABLE 2-continued

μ Affinities of Examples 11-161:

| No. | n | R¹ | R² | R³ | μ-Opioid receptor, % inhibition [1 μM] |
|---|---|---|---|---|---|
| 42 | 0 | 2-phenylethyl | 4-chlorophenyl | n-pentyl | 94 |
| 43 | 1 | 2-phenylethyl | 4-chlorophenyl | isobutyl | 97 |
| 44 | 1 | 2-phenylethyl | 4-chlorophenyl | 4-chlorobenzyl | 91 |
| 45 | 1 | 2-phenylethyl | 4-chlorophenyl | n-pentyl | 97 |
| 46 | 0 | benzyl | 3-fluorophenyl | isobutyl | 92 |
| 47 | 0 | benzyl | 3-fluorophenyl | 4-chlorobenzyl | 74 |
| 48 | 0 | benzyl | 4-chlorophenyl | isobutyl | 93 |

TABLE 2-continued
μ Affinities of Examples 11-161:
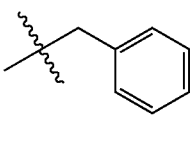
| No. | n | R¹ | R² | R³ | μ-Opioid receptor, % inhibition [1 μM] |
|---|---|---|---|---|---|
| 49 | 0 | 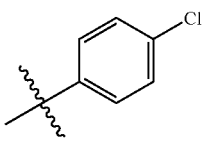 | 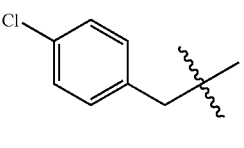 | 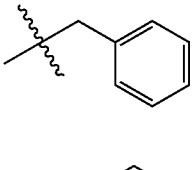 | 84 |
| 50 | 1 | 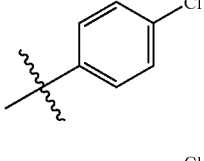 | 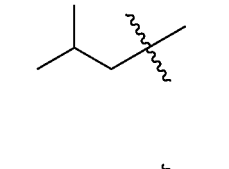 | 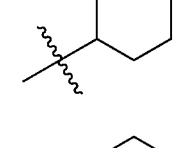 | 94 |
| 51 | 0 | 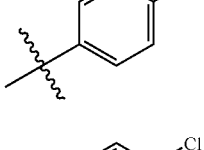 | 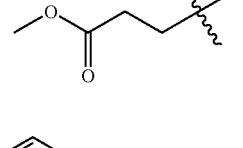 | 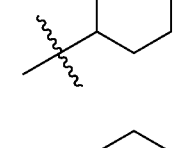 | 96 |
| 52 | 0 | 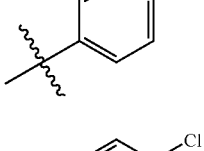 | 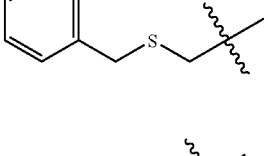 | 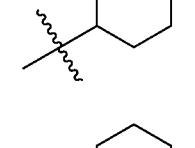 | 99 |
| 53 | 1 | 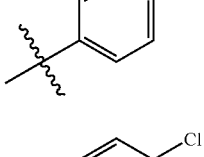 | 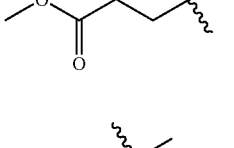 | 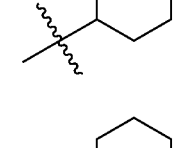 | 96 |
| 54 | 1 | 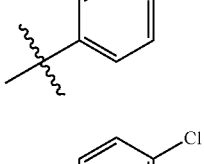 | 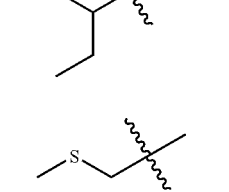 | 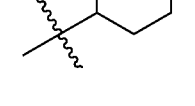 | 100 |
| 55 | 1 | 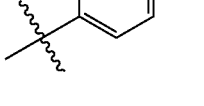 |  | | 91 |

TABLE 2-continued

μ Affinities of Examples 11-161:

| No. | n | R¹ | R² | R³ | μ-Opioid receptor, % inhibition [1 μM] |
|---|---|---|---|---|---|
| 56 | 1 | cyclohexyl | 4-Cl-phenyl | benzyl-S-CH< | 97 |
| 57 | 0 | n-propyl | 3-F-phenyl | CH₃-S-CH< | 86 |
| 58 | 0 | n-propyl | 3-F-phenyl | benzyl-S-CH< | 81 |
| 59 | 0 | n-propyl | 4-Cl-phenyl | methyl ester propyl | 84 |
| 60 | 0 | n-propyl | 4-Cl-phenyl | benzyl-S-CH< | 95 |
| 61 | 1 | n-propyl | 4-Cl-phenyl | methyl ester propyl | 93 |
| 62 | 1 | n-propyl | 4-Cl-phenyl | sec-butyl | 98 |

TABLE 2-continued

μ Affinities of Examples 11-161:

| No. | n | R¹ | R² | R³ | μ-Opioid receptor, % inhibition [1 μM] |
|---|---|---|---|---|---|
| 63 | 1 | n-butyl | 4-chlorophenyl | methylthiomethyl | 97 |
| 64 | 1 | n-butyl | 4-chlorophenyl | benzylthiomethyl | 98 |
| 65 | 0 | pentan-3-yl | 3-fluorophenyl | methyl propanoate | 78 |
| 66 | 0 | pentan-3-yl | 3-fluorophenyl | methylthiomethyl | 89 |
| 67 | 0 | pentan-3-yl | 3-fluorophenyl | benzylthiomethyl | 88 |
| 68 | 0 | pentan-3-yl | 4-chlorophenyl | methyl propanoate | 90 |

TABLE 2-continued

μ Affinities of Examples 11-161:

| No. | n | R¹ | R² | R³ | μ-Opioid receptor, % inhibition [1 μM] |
|---|---|---|---|---|---|
| 69 | 0 | pentyl | 4-Cl-phenyl | benzyl-S-CH₂- | 95 |
| 70 | 1 | pentyl | 4-Cl-phenyl | methyl propanoate | 96 |
| 71 | 1 | butyl | phenethyl | methyl propanoate | 78 |
| 72 | 1 | pentyl | 3-F-phenyl | methyl propanoate | 95 |
| 73 | 1 | pentyl | 3-F-phenyl | sec-butyl | 92 |
| 74 | 1 | pentyl | 3-F-phenyl | CH₃-S-CH₂- | 95 |

TABLE 2-continued
μ Affinities of Examples 11-161:
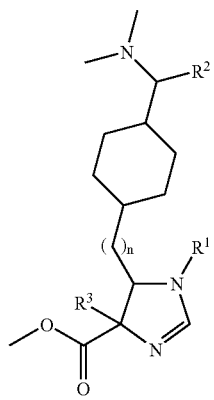
| No. | n | R¹ | R² | R³ | μ-Opioid receptor, % inhibition [1 μM] |
|---|---|---|---|---|---|
| 75 | 1 | n-butyl | 3-F-phenyl | benzyl-S-CH₂ | 98 |
| 76 | 1 | n-butyl | 4-F-phenyl | methyl ester propyl | 93 |
| 77 | 1 | n-butyl | 4-F-phenyl | methyl-S-CH₂ | 88 |
| 78 | 1 | n-butyl | phenethyl | methyl ester propyl | 67 |
| 79 | 1 | n-butyl | phenethyl | benzyl-S-CH₂ | 79 |
| 80 | 1 | phenethyl | 3-F-phenyl | methyl ester propyl | 90 |

TABLE 2-continued

μ Affinities of Examples 11-161:

| No. | n | R¹ | R² | R³ | μ-Opioid receptor, % inhibition [1 μM] |
|---|---|---|---|---|---|
| 81 | 1 | 2-phenylethyl | 3-fluorophenyl | sec-butyl (3-methylbutan-2-yl) | 76 |
| 82 | 1 | 2-phenylethyl | 3-fluorophenyl | benzylthiomethyl | 95 |
| 83 | 1 | 2-phenylethyl | 4-fluorophenyl | methyl propanoate | 77 |
| 84 | 1 | 2-phenylethyl | 2-phenylethyl | methyl propanoate | 75 |
| 85 | 1 | benzyl | 3-fluorophenyl | methyl propanoate | 95 |
| 86 | 1 | benzyl | 3-fluorophenyl | benzylthiomethyl | 71 |

TABLE 2-continued

µ Affinities of Examples 11-161:

| No. | n | R¹ | R² | R³ | µ-Opioid receptor, % inhibition [1 µM] |
|---|---|---|---|---|---|
| 87 | 1 | benzyl | 4-F-phenyl | -CH₂CH₂C(O)OCH₃ | 95 |
| 88 | 1 | n-butyl | 4-Cl-phenyl | sec-butyl | 98 |
| 89 | 1 | n-butyl | 4-Cl-phenyl | -CH₂SCH₃ | 96 |
| 90 | 1 | n-butyl | 4-Cl-phenyl | -CH₂SCH₂-phenyl | 99 |
| 91 | 0 | phenethyl | 3-F-phenyl | -CH₂CH₂C(O)OCH₃ | 85 |
| 92 | 0 | phenethyl | 3-F-phenyl | -CH₂SCH₂-phenyl | 95 |
| 93 | 0 | phenethyl | 4-Cl-phenyl | -CH₂SCH₂-phenyl | 92 |

TABLE 2-continued

μ Affinities of Examples 11-161:

| No. | n | R¹ | R² | R³ | μ-Opioid receptor, % inhibition [1 μM] |
|---|---|---|---|---|---|
| 94 | 1 | phenethyl | 4-Cl-phenyl | methyl propanoate | 97 |
| 95 | 0 | benzyl | 3-F-phenyl | methyl propanoate | 94 |
| 96 | 0 | benzyl | 3-F-phenyl | methylthioethyl | 97 |
| 97 | 0 | benzyl | 3-F-phenyl | benzylthiomethyl | 97 |
| 98 | 0 | benzyl | 4-Cl-phenyl | benzylthiomethyl | 95 |
| 99 | 1 | benzyl | 4-Cl-phenyl | methyl propanoate | 100 |

TABLE 2-continued

μ Affinities of Examples 11-161:

| No. | n | R¹ | R² | R³ | μ-Opioid receptor, % inhibition [1 μM] |
|---|---|---|---|---|---|
| 100 | 1 | benzyl | 4-Cl-phenyl | -CH₂-S-CH₃ | 97 |
| 101 | 1 | benzyl | 4-Cl-phenyl | -CH₂-S-CH₂-phenyl | 96 |
| 102 | 1 | cyclohexyl | 3-F-phenyl | n-propyl | 91 |
| 103 | 1 | cyclohexyl | 3-F-phenyl | -CH₂CH₂-S-CH₃ | 99 |
| 104 | 1 | cyclohexyl | 3-F-phenyl | Me | 93 |
| 105 | 1 | cyclohexyl | 4-F-phenyl | n-propyl | 95 |

TABLE 2-continued

μ Affinities of Examples 11-161:

| No. | n | R¹ | R² | R³ | μ-Opioid receptor, % inhibition [1 μM] |
|---|---|---|---|---|---|
| 106 | 1 | cyclohexyl | 4-F-phenyl | -CH₂CH₂-S-Me | 92 |
| 107 | 1 | cyclohexyl | 4-F-phenyl | Me | 87 |
| 108 | 1 | cyclohexyl | -CH₂CH₂-phenyl | n-propyl | 86 |
| 109 | 1 | cyclohexyl | -CH₂CH₂-phenyl | -CH₂CH₂-S-Me | 87 |
| 110 | 1 | cyclohexyl | -CH₂CH₂-phenyl | Me | 67 |
| 111 | 1 | n-propyl | 3-F-phenyl | n-propyl | 90 |
| 112 | 1 | n-propyl | 3-F-phenyl | -CH₂CH₂-S-Me | 95 |

TABLE 2-continued

μ Affinities of Examples 11-161:

| No. | n | R¹ | R² | R³ | μ-Opioid receptor, % inhibition [1 μM] |
|---|---|---|---|---|---|
| 113 | 1 | benzyl | 4-Cl-phenyl | 4-Cl-benzyl | 92 |
| 114 | 1 | benzyl | 4-Cl-phenyl | n-pentyl | 86 |
| 115 | 0 | cyclohexyl | 3-F-phenyl | -CH₂CH₂C(O)OMe | 98 |
| 116 | 0 | cyclohexyl | 3-F-phenyl | -CH₂-S-CH₂-phenyl | 101 |
| 117 | 1 | n-propyl | 3-F-phenyl | Me | 88 |
| 118 | 1 | n-propyl | 4-F-phenyl | n-butyl | 87 |

TABLE 2-continued

µ Affinities of Examples 11-161:

| No. | n | R¹ | R² | R³ | µ-Opioid receptor, % inhibition [1 µM] |
|---|---|---|---|---|---|
| 119 | 1 | propyl | 4-fluorophenyl | -CH₂CH₂SMe | 90 |
| 120 | 1 | propyl | -CH₂CH₂-phenyl | propyl | 62 |
| 121 | 1 | propyl | -CH₂CH₂-phenyl | -CH₂CH₂SMe | 77 |
| 122 | 1 | butyl | 4-fluorophenyl | butyl | 95 |
| 123 | 1 | butyl | 3-fluorophenyl | -CH₂CH₂SMe | 98 |
| 124 | 1 | butyl | 3-fluorophenyl | Me | 95 |
| 125 | 1 | butyl | 4-fluorophenyl | propyl | 91 |

TABLE 2-continued

μ Affinities of Examples 11-161:

| No. | n | R¹ | R² | R³ | μ-Opioid receptor, % inhibition [1 μM] |
|---|---|---|---|---|---|
| 126 | 1 | n-pentyl | 4-fluorophenyl | -CH₂CH₂SMe | 98 |
| 127 | 1 | n-pentyl | -CH₂CH₂-phenyl | n-butyl | 74 |
| 128 | 1 | n-pentyl | -CH₂CH₂-phenyl | -CH₂CH₂SMe | 83 |
| 129 | 1 | -CH₂CH₂-phenyl | 3-fluorophenyl | n-butyl | 93 |
| 130 | 1 | -CH₂CH₂-phenyl | 3-fluorophenyl | -CH₂CH₂SMe | 97 |
| 131 | 1 | -CH₂CH₂-phenyl | 3-fluorophenyl | Me | 100 |

TABLE 2-continued

µ Affinities of Examples 11-161:

| No. | n | R¹ | R² | R³ | µ-Opioid receptor, % inhibition [1 µM] |
|-----|---|-----|-----|-----|---------|
| 132 | 1 | phenethyl | 4-F-phenyl | n-propyl | 98 |
| 133 | 1 | phenethyl | 4-F-phenyl | -CH₂CH₂SMe | 84 |
| 134 | 1 | phenethyl | 4-F-phenyl | Me | 92 |
| 135 | 1 | phenethyl | phenethyl | n-propyl | 85 |
| 136 | 1 | phenethyl | phenethyl | -CH₂CH₂SMe | 76 |
| 137 | 1 | phenethyl | phenethyl | Me | 61 |
| 138 | 1 | benzyl | 3-F-phenyl | n-propyl | 101 |

TABLE 2-continued

μ Affinities of Examples 11-161:

| No. | n | R¹ | R² | R³ | μ-Opioid receptor, % inhibition [1 μM] |
|-----|---|----|----|----|----------------------------------------|
| 139 | 1 | benzyl | 3-F-phenyl | -CH₂CH₂-S-Me | 100 |
| 140 | 1 | benzyl | 3-F-phenyl | Me | 98 |
| 141 | 1 | benzyl | 4-F-phenyl | n-propyl | 98 |
| 142 | 1 | benzyl | 4-F-phenyl | -CH₂CH₂-S-Me | 97 |
| 143 | 1 | benzyl | 4-F-phenyl | Me | 100 |
| 144 | 1 | benzyl | phenethyl | n-propyl | 90 |
| 145 | 1 | benzyl | phenethyl | -CH₂CH₂-S-Me | 79 |

TABLE 2-continued

μ Affinities of Examples 11-161:

| No. | n | R¹ | R² | R³ | μ-Opioid receptor, % inhibition [1 μM] |
|---|---|---|---|---|---|
| 146 | 1 | benzyl | 2-phenylethyl | Me | 79 |
| 147 | 1 | cyclohexyl | 3-fluorophenyl | -C(CH₃)₂CH₂CH₂C(=O)OCH₃ | 98 |
| 148 | 1 | cyclohexyl | 3-fluorophenyl | sec-butyl (2-methylbutyl) | 95 |
| 149 | 1 | cyclohexyl | 3-fluorophenyl | -CH₂CH₂SCH₃ | 99 |
| 150 | 1 | cyclohexyl | 3-fluorophenyl | -CH₂CH₂SCH₂Ph | 98 |
| 151 | 1 | cyclohexyl | 4-fluorophenyl | -C(CH₃)₂CH₂CH₂C(=O)OCH₃ | 95 |

TABLE 2-continued

µ Affinities of Examples 11-161:

| No. | n | R¹ | R² | R³ | µ-Opioid receptor, % inhibition [1 µM] |
|---|---|---|---|---|---|
| 152 | 1 | cyclohexyl | 4-F-phenyl | sec-butyl (2-butyl) | 93 |
| 153 | 1 | cyclohexyl | 4-F-phenyl | -CH₂-S-CH₃ | 93 |
| 154 | 1 | cyclohexyl | -CH₂CH₂-phenyl | -CH₂CH₂-C(O)-O-CH₃ | 82 |
| 155 | 1 | cyclohexyl | -CH₂CH₂-phenyl | -CH₂-S-CH₃ | 86 |
| 156 | 1 | cyclohexyl | -CH₂CH₂-phenyl | -CH₂-S-CH₂-phenyl | 92 |
| 157 | 1 | n-propyl | 3-F-phenyl | -CH₂CH₂-C(O)-O-CH₃ | 91 |

TABLE 2-continued

μ Affinities of Examples 11-161:

| No. | n | R¹ | R² | R³ | μ-Opioid receptor, % inhibition [1 μM] |
|---|---|---|---|---|---|
| 158 | 1 | n-propyl | 3-fluorophenyl | -CH₂-S-CH₃ | 95 |
| 159 | 1 | n-propyl | 4-fluorophenyl | -CH₂CH₂CH₂-C(O)-O-CH₃ | 79 |
| 160 | 1 | n-propyl | 4-fluorophenyl | -CH₂-S-CH₃ | 74 |
| 161 | 1 | n-propyl | 4-fluorophenyl | -CH₂-S-CH₂-phenyl | 91 |

What is claimed is:

1. A substituted imidazoline compound corresponding to Formula I:

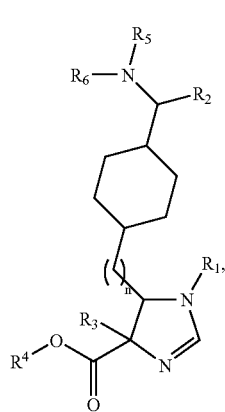

wherein
n is 0, 1 or 2;
$R^1$ denotes a saturated or unsaturated, branched or unbranched, optionally mono- or polysubstituted $C_{1-8}$-alkyl group; a saturated or unsaturated, optionally mono- or polysubstituted $C_{3-8}$-cycloalkyl group; or an optionally mono- or polysubstituted aryl or heteroaryl group bonded via a $C_{1-3}$-alkylene chain;
$R^2$ denotes an optionally mono- or polysubstituted aryl or heteroaryl group; or an optionally mono- or polysubstituted aryl group bonded via a $C_{1-3}$-alkylene chain;
$R^3$ denotes a saturated or unsaturated, branched or unbranched, optionally mono- or polysubstituted $C_{1-8}$-alkyl group; or an optionally mono- or polysubstituted aryl group bonded via a $C_{1-3}$-alkylene chain;
$R^4$ denotes H, a $C_{1-4}$-alkyl group, or an aryl group bonded via a $C_{1-3}$-alkylene chain;
$R^5$ and $R^6$ independently denote H or saturated or unsaturated, branched or unbranched $C_{1-6}$-alkyl, with the proviso that $R^5$ and $R^6$ do not simultaneously denote H, or
$R^5$ and $R^6$ together denote —$CH_2CH_2OCH_2CH_2$—, or —$(CH_2)_{3-6}$—;
or a salt thereof with a physiologically compatible acid.

2. A compound as claimed in claim 1, wherein said compound is in the form of an isolated stereoisomer.

3. A compound as claimed in claim 1, wherein said compound is in the form of a mixture of stereoisomers.

4. A compound as claimed in claim 3, wherein said compound is in the form of a racemic mixture.

5. A compound as claimed in claim 1, wherein $R^1$ denotes:
branched or unbranched $C_{1-8}$-alkyl which is unsubstituted or mono- or polysubstituted with F, Cl, —CN, SH, S—$C_{1-6}$-alkyl, S-benzyl, OH, O-benzyl, O—$C_{1-6}$-alkyl, $CO_2H$, or $CO_2$—$C_{1-6}$-alkyl;
$C_{3-8}$-cycloalkyl which is unsubstituted or mono- or polysubstituted with F, Cl, —CN, SH, S—$C_{1-6}$-alkyl, S-benzyl, OH, O-benzyl, O—$C_{1-6}$-alkyl, $CO_2H$, or $CO_2$—$C_{1-6}$-alkyl; or
a phenyl group bonded via a $C_{1-3}$-alkylene chain, wherein the phenyl group is unsubstituted or mono- or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$-alkyl.

6. A compound as claimed in claim 1, wherein $R^1$ denotes cyclohexyl, n-propyl, n-butyl, phenethyl or benzyl.

7. A compound as claimed in claim 1, wherein $R^2$ denotes:
phenyl or thienyl, which is unsubstituted or mono- or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$-alkyl; or
a phenyl group bonded via a $C_{1-3}$-alkyl chain, wherein the phenyl group is unsubstituted or mono- or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$-alkyl.

8. A compound as claimed in claim 1, wherein $R^2$ denotes phenyl which is unsubstituted or monosubstituted with Cl or F, or thienyl or phenethyl.

9. A compound as claimed in claim 1, wherein $R^3$ denotes:
branched or unbranched $C_{1-8}$-alkyl which is unsubstituted or mono- or polysubstituted with F, Cl, —CN, SH, S—$C_{1-6}$-alkyl, S-benzyl, OH, O-benzyl, O—$C_{1-6}$-alkyl, $CO_2H$, or $CO_2$—$C_{1-6}$-alkyl; or
a phenyl group bonded via a $C_{1-3}$-alkyl chain, wherein the phenyl group is unsubstituted or mono-polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$-alkyl.

10. A compound as claimed in claim 1, wherein $R^3$ denotes sec-butyl, iso-butyl, n-butyl, n-propyl, $CH_3$, $CH_2$ $CH_2$ $COOCH_3$, $CH_2$—S-benzyl, $CH_2CH_2$—S—$CH_3$, $CH_2$—S—$CH_3$, or 4-Cl-benzyl.

11. A compound as claimed in claim 1, wherein $R^4$ denotes $CH_3$.

12. A compound as claimed in claim 1, wherein $R^5$ and $R^6$ each denote $CH_3$.

13. A compound as claimed in claim 1, selected from the group consisting of:
1-cyclohexyl-5-{4-[dimethylamino-(3-fluorophenyl)-methyl]-cyclohexyl}-4-isobutyl-4,5-dihydro-1H-imidazole-4-carboxylic acid methyl ester;
4-(4-chlorobenzyl)-1-cyclohexyl-5-{4-[dimethylamino-(3-fluorophenyl)-methyl]-cyclohexyl}-4,5-dihydro-1H-imidazole-4-carboxylic acid methyl ester;
4-butyl-1-cyclohexyl-5-{4-[dimethylamino-(3-fluorophenyl)-methyl]-cyclohexyl}-4,5-dihydro-1H-imidazole-4-carboxylic acid methyl ester;
5-{4-[(4-chlorophenyl)-dimethylaminomethyl]-cyclohexyl}-1-cyclohexyl-4-isobutyl-4,5-dihydro-1H-imidazole-4-carboxylic acid methyl ester;
4-(4-chlorobenzyl)-5-{4-[(4-chlorophenyl)-dimethylaminomethyl]-cyclohexyl}-1-cyclohexyl-4,5-dihydro-1H-imidazole-carboxylic acid methyl ester;
4-butyl-5-{4-[(4-chlorophenyl)-dimethylaminomethyl]-cyclohexyl}-1-cyclohexyl-4,5-dihydro-1H-imidazole-4-carboxylic carboxylic acid methyl ester;
5-{4-[(4-chlorophenyl)-dimethylaminomethyl]-cyclohexylmethyl}-1-cyclohexyl-4-isobutyl-4,5-dihydro-1H-imidazole-4-carboxylic acid methyl ester;
4-(4-chlorobenzyl)-5-{4-[(4-chlorophenyl)-dimethylaminomethyl]-cyclohexylmethyl}-1-cyclohexyl-4,5-dihydro-1H-imidazole-4-carboxylic acid methyl ester;
4-butyl-5-{4-[(4-chlorophenyl)-dimethylaminomethyl]-cyclohexylmethyl}-1-cyclohexyl-4,5-dihydro-1H-imidazole-4-carboxylic acid methyl ester;

4-(4-chlorobenzyl)-1-cyclohexyl-5-[4-(dimethylaminothiophen-2-yl-methyl)-cyclohexylmethyl]-4,5-dihydro-1H-imidazole-4-carboxylic acid methyl ester;

5-{4-[dimethylamino-(3-fluorophenyl)-methyl]-cyclohexyl}-4-isobutyl-1-propyl-4,5-dihydro-1H-imidazole-4-carboxylic acid methyl ester;

4-(4-chlorobenzyl)-5-{4-[dimethylamino-(3-fluorophenyl)-methyl]-cyclohexyl}-1-propyl-4,5-dihydro-1H-imidazole-4-carboxylic acid methyl ester;

4-butyl-5-{4-[dimethylamino-(3-fluorophenyl)-methyl]-cyclohexyl}-1-propyl-4,5-dihydro-1H-imidazole-4-carboxylic acid methyl ester;

5-{4-[(4-chlorophenyl)-dimethylaminomethyl]-cyclohexyl}-4-isobutyl-1-propyl-4,5-dihydro-1H-imidazole-4-carboxylic acid methyl ester;

4-(4-chlorobenzyl)-5-{4-[(4-chlorophenyl)-dimethylaminomethyl]-cyclohexyl}-1-propyl-4,5-dihydro-1H-imidazole-4-carboxylic acid methyl ester;

5-{4-[(4-chlorophenyl)-dimethylaminomethyl]-cyclohexylmethyl}-4-isobutyl-1-propyl-4,5-dihydro-1H-imidazole-4-carboxylic acid methyl ester;

4-(4-chlorobenzyl)-5-{4-[(4-chlorophenyl)-dimethylaminomethyl]-cyclohexylmethyl}-1-propyl-4,5-dihydro-1H-imidazole-4-carboxylic acid methyl ester;

4-butyl-5-{4-[(4-chlorophenyl)-dimethylaminomethyl]-cyclohexylmethyl}-1-propyl-4,5-dihydro-1H-imidazole-4-carboxylic acid methyl ester;

1-butyl-5-{4-[dimethylamino-(3-fluorophenyl)-methyl]-cyclohexyl}-4-isobutyl-4,5-dihydro-1H-imidazole-4-carboxylic acid methyl ester;

1-butyl-4-(4-chlorobenzyl)-5-{4-[dimethylamino-(3-fluorophenyl)-methyl]-cyclohexyl}-4,5-dihydro-1H-imidazole-4-carboxylic acid methyl ester;

1-butyl-5-{4-[(chlorophenyl)-dimethylaminomethyl]-cyclohexyl}-4-isobutyl-4,5-dihydro-1H-imidazole-4-carboxylic acid methyl ester;

1-butyl-4-(4-chlorobenzyl)-5-{4-[(4-chlorophenyl)-dimethylaminomethyl]-cyclohexyl}-4,5-dihydro-1H-imidazole-4-carboxylic acid methyl ester;

1,4-dibutyl-5-{4-[(4-chlorophenyl)-dimethylaminomethyl]-cyclohexyl}-4,5-dihydro-1H-imidazole-4-carboxylic acid methyl ester;

1-butyl-5-{4-[(chlorophenyl)-dimethylaminomethyl]-cyclohexylmethyl}-4-isobutyl-4,5-dihydro-1H-imidazole-4-carboxylic acid methyl ester;

1-butyl-4-(4-chlorobenzyl)-5-{4-[(4-chlorophenyl)-dimethylaminomethyl]-cyclohexylmethyl}-4,5-dihydro-1H-imidazole-4-carboxylic acid methyl ester;

1,4-dibutyl-5-{4-[(4-chlorophenyl)-dimethylaminomethyl]-cyclohexylmethyl}-4,5-dihydro-1H-imidazole-4-carboxylic acid methyl ester;

5-{4-[dimethylamino-(3-fluorophenyl)-methyl]-cyclohexyl}-4-isobutyl-1-phenethyl-4,5-dihydro-1H-imidazole-4-carboxylic acid methyl ester;

4-(4-chlorobenzyl)-5-{4-[dimethylamino-(3-fluorophenyl)-methyl]-cyclohexyl}-1-phenethyl-1H-imidazole-4-carboxylic acid methyl ester;

4-butyl-5-{4-[dimethylamino-(3-fluorophenyl)-methyl]-cyclohexyl}-1-phenethyl-4,5-dihydro-1H-imidazole-4-carboxylic acid methyl ester;

5-{4-[(4-chlorophenyl)-dimethylaminomethyl]-cyclohexyl}-4-isobutyl-1-phenethyl-4,5-dihydro-1H-imidazole-4-carboxylic acid methyl ester;

4-(4-chlorobenzyl)-5-{4-[(4-chlorophenyl)-dimethylaminomethyl]-cyclohexyl}-1-phenethyl-4,5-dihydro-1H-imidazole-4-carboxylic acid methyl ester;

4-butyl-5-{4-[(4-chlorophenyl)-dimethylaminomethyl]-cyclohexyl}-1-phenethyl-4,5-dihydro-1H-imidazole-4-carboxylic acid methyl ester;

5-{4-[(4-chlorophenyl)-dimethylaminomethyl]-cyclohexylmethyl}-4-isobutyl-1-phenethyl-1H-imidazole-4-carboxylic acid methyl ester;

4-(4-chlorobenzyl)-5-{4-[(4-chlorophenyl)-dimethylaminomethyl]-cyclohexylmethyl}-1-phenethyl-4,5-dihydro-1H-imidazole-4-carboxylic acid methyl ester;

4-butyl-5-{4-[(4-chlorophenyl)-dimethylaminomethyl]-cyclohexylmethyl}-1-phenethyl-4,5-dihydro-1H-imidazole-4-carboxylic acid methyl ester;

1-benzyl-5-{4-[dimethylamino-(3-fluorophenyl)-methyl]-cyclohexyl}-4-isobutyl-4,5-dihydro-1H-imidazole-4-carboxylic acid methyl ester;

1-benzyl-4-(4-chlorobenzyl)-5-{4-[dimethylamino-(3-fluorophenyl)-methyl]-cyclohexyl}-4,5-dihydro-1H-imidazole-4-carboxylic acid methyl ester;

1-benzyl-5-{4-[(4-chlorophenyl)-dimethylaminomethyl]-cyclohexyl}-4-isobutyl-4,5-dihydro-1H-imidazole-4-carboxylic acid methyl ester;

1-benzyl-4-(4-chlorobenzyl)-5-{4-[(4-chlorophenyl)-dimethylaminomethyl]-cyclohexyl}-4,5-dihydro-1H-imidazole-4-carboxylic acid methyl ester;

1-benzyl-5-{4-[(4-chlorophenyl)-dimethylaminomethyl]-cyclohexylmethyl}-4-isobutyl-4,5-dihydro-1H-imidazole-4-carboxylic acid methyl ester;

5-{4-[(4-chlorophenyl)-dimethylaminomethyl]-cyclohexyl}-1-cyclohexyl-4-(2-methoxycarbonylethyl)-4,5-dihydro-1H-imidazole-4-carboxylic acid methyl ester;

4-benzylsulfanylmethyl-5-{4-[(4-chlorophenyl)-dimethylaminomethyl]-cyclohexyl}-1-cyclohexyl-4,5-dihydro-1H-imidazole-4-carboxylic acid methyl ester;

5-{4-[(4-chlorophenyl)-dimethylaminomethyl]-cyclohexylmethyl}-1-cyclohexyl-4-(2-methoxycarbonylethyl)-4,5-dihydro-1H-imidazole-4-carboxylic acid methyl ester;

1-benzyl-5-{4-[dimethylamino-(3-fluorophenyl)-methyl]-cyclohexylmethyl}-4-propyl-4,5-dihydro-1H-imidazole-4-carboxylic acid methyl ester;

5-{4-[(4-chlorophenyl)-dimethylaminomethyl]-cyclohexylmethyl}-1-cyclohexyl-4-methylsulfanylmethyl-4,5-dihydro-1H-imidazole-4-carboxylic acid methyl ester;

4-benzylsulfanylmethyl-5-{4-[(4-chlorophenyl)-dimethylaminomethyl]-cyclohexylmethyl}-1-cyclohexyl-4,5-dihydro-1H-imidazole-4-carboxylic acid methyl ester;

5-{4-[dimethylamino-(3-fluorophenyl)-methyl]-cyclohexyl}-4-methylsulfanylmethyl-1-propyl-4,5-dihydro-1H-imidazole-4-carboxylic acid methyl ester;

4-benzylsulfanylmethyl-5-{4-[dimethylamino-(3-fluorophenyl)-methyl]-cyclohexyl}-1-propyl-4,5-dihydro-1H-imidazole-4-carboxylic acid methyl ester;

5-{4-[(4-chlorophenyl)-dimethylaminomethyl]-cyclohexyl}-4-(2-methoxycarbonylethyl)-1-propyl-4,5-dihydro-1H-imidazole-4-carboxylic acid methyl ester;

4-benzylsulfanylmethyl-5-{4-[(4-chlorophenyl)-dimethylaminomethyl]-cyclohexyl}-1-propyl-4,5-dihydro-1H-imidazole-4-carboxylic acid methyl ester;

5-{4-[(4-chlorophenyl)-dimethylaminomethyl]-cyclohexylmethyl}-4-(2-methoxycarbonylethyl)-1-propyl-4,5-dihydro-1H-imidazole-4-carboxylic acid methyl ester;

4-sec-butyl-5-{4-[(4-chlorophenyl)-dimethylaminomethyl]-cyclohexylmethyl}-1-propyl-4,5-dihydro-1H-imidazole-4-carboxylic acid methyl ester;

5-{4-[(4-chlorophenyl)-dimethylaminomethyl]-cyclohexylmethyl}-4-methylsulfanylmethyl-1-propyl-4,5-dihydro-1H-imidazole-4-carboxylic acid methyl ester;

4-benzylsulfanylmethyl-5-{4-[(4-chlorophenyl)-dimethylaminomethyl]-cyclohexylmethyl}-1-propyl-4,5-dihydro-1H-imidazole-4-carboxylic acid methyl ester;

1-butyl-5-{4-[dimethylamino-(3-fluorophenyl)-methyl]-cyclohexyl}-4-(2-methoxycarbonylethyl)-4,5-dihydro-1H-imidazole-4-carboxylic acid methyl ester;

1-butyl-5-{4-[dimethylamino-(3-fluorophenyl)-methyl]-cyclohexyl}-4-methylsulfanylmethyl-4,5-dihydro-1H-imidazole-4-carboxylic acid methyl ester;

4-benzylsulfanylmethyl-1-butyl-5-{4-[dimethylamino-(3-fluorophenyl)-methyl]-cyclohexyl}-4,5-dihydro-1H-imidazole-4-carboxylic acid methyl ester;

1-butyl-5-{4-[(4-chlorophenyl)-dimethylaminomethyl]-cyclohexyl}-4-(2-methoxycarbonylethyl)-4,5-dihydro-1H-imidazole-4-carboxylic acid methyl ester;

4-benzylsulfanylmethyl-1-butyl-5-{4-[(4-chlorophenyl)-dimethylaminomethyl]-cyclohexyl}-4,5-dihydro-1H-imidazole-4-carboxylic acid methyl ester;

1-butyl-5-{4-[(4-chlorophenyl)-dimethylaminomethyl]-cyclohexylmethyl}-4-(2-methoxycarbonylethyl)-4,5-dihydro-1H-imidazole-4-carboxylic acid methyl ester;

5-[4-(1-dimethylamino-3-phenylpropyl)-cyclohexylmethyl]-4-(2-methoxycarbonylethyl)-1-propyl-4,5-dihydro-1H-imidazole-4-carboxylic acid methyl ester;

1-butyl-5-{4-[dimethylamino-(3-fluorophenyl)-methyl]-cyclohexylmethyl}-4-(2-methoxycarbonylethyl)-4,5-dihydro-1H-imidazole-4-carboxylic acid methyl ester;

1-butyl-4-sec-butyl-5-{4-[dimethylamino-(3-fluorophenyl)-methyl]-cyclohexylmethyl}-4,5-dihydro-1H-imidazole-4-carboxylic acid methyl ester;

1-butyl-5-{4-[dimethylamino-(3-fluorophenyl)-methyl]-cyclohexylmethyl}-4-methylsulfanylmethyl-4,5-dihydro-1H-imidazole-4-carboxylic acid methyl ester;

4-benzylsulfanylmethyl-1-butyl-5-{4-[dimethylamino-(3-fluorophenyl)-methyl]-cyclohexylmethyl}-4,5-dihydro-1H-imidazole-4-carboxylic acid methyl ester;

1-butyl-5-{4-[dimethylamino-(4-fluorophenyl)-methyl]-cyclohexylmethyl}-4-(2-methoxycarbonylethyl)-4,5-dihydro-1H-imidazole-4-carboxylic acid methyl ester;

1-butyl-5-{4-[dimethylamino-(4-fluorophenyl)-methyl]-cyclohexylmethyl}-4-methylsulfanylmethyl-4,5-dihydro-1H-imidazole-4-carboxylic acid methyl ester;

1-butyl-5-[4-(1-dimethylamino-3-phenylpropyl)-cyclohexyl methyl]-4-(2-methoxycarbonylethyl)-4,5-dihydro-1H-imidazole-4-carboxylic acid methyl ester;

4-benzylsulfanylmethyl-1-butyl-5-[4-(1-dimethylamino-3-phenylpropyl)-cyclohexylmethyl]-4,5-dihydro-1H-imidazole-4-carboxylic acid methyl ester;

5-{4-[dimethylamino-(3-fluorophenyl)-methyl]-cyclohexylmethyl}-4-(2-methoxycarbonylethyl)-1-phenethyl-4,5-dihydro-1H-imidazole-4-carboxylic acid methyl ester;

4-sec-butyl-5-{4-[dimethylamino-(3-fluorophenyl)-methyl]-cyclohexylmethyl}-1-phenethyl-4,5-dihydro-1H-imidazole-4-carboxylic acid methyl ester;

4-benzylsulfanylmethyl-5-{4-[dimethylamino-(3-fluorophenyl)-methyl]-cyclohexylmethyl}-1-phenethyl-4,5-dihydro-1H-imidazole-4-carboxylic acid methyl ester;

5-{4-[dimethylamino-(4-fluorophenyl)-methyl]-cyclohexylmethyl}-4-(2-methoxycarbonylethyl)-1-phenethyl-4,5-dihydro-1H-imidazole-4-carboxylic acid methyl ester;

5-[4-(1-dimethylamino-3-phenylpropyl)-cyclohexylmethyl]-4-(2-methoxycarbonylethyl)-1-phenethyl-4,5-dihydro-1H-imidazole-4-carboxylic acid methyl ester;

1-benzyl-5-{4-[dimethylamino-(3-fluorophenyl)-methyl]-cyclohexylmethyl}-4-(2-methoxycarbonylethyl)-4,5-dihydro-1H-imidazole-4-carboxylic acid methyl ester;

1-benzyl-4-benzylsulfanylmethyl-5-{4-[dimethylamino-(3-fluorophenyl)-methyl]-cyclohexylmethyl}-4,5-dihydro-1H-imidazole-4-carboxylic acid methyl ester;

1-benzyl-5-{4-[dimethylamino-(4-fluorophenyl)-methyl]-cyclohexylmethyl}-4-(2-methoxycarbonylethyl)-4,5-dihydro-1H-imidazole-carboxylic acid methyl ester;

1-butyl-4-sec-butyl-5-{4-[(4-chlorophenyl)-dimethylaminomethyl]-cyclohexylmethyl}-4,5-dihydro-1H-imidazole-4-carboxylic acid methyl ester;

1-butyl-5-{4-[(4-chlorophenyl)-dimethylaminomethyl]-cyclohexylmethyl}-4-methylsulfanylmethyl-4,5-dihydro-1H-imidazole-4-carboxylic acid methyl ester;

4-benzylsulfanylmethyl-1-butyl-5-{4-[(4-chlorophenyl)-dimethylaminomethyl]-cyclohexylmethyl}-4,5-dihydro-1H-imidazole-4-carboxylic acid methyl ester;

5-{4-[dimethylamino-(3-fluorophenyl)-methyl]-cyclohexyl}-4-(2-methoxycarbonylethyl)-1-phenethyl-4,5-dihydro-1H-imidazole-4-carboxylic acid methyl ester;

4-benzylsulfanylmethyl-5-{4-[dimethylamino-(3-fluorophenyl)-methyl]-cyclohexyl}-1-phenethyl-4,5-dihydro-1H-imidazole-4-carboxylic acid methyl ester;

4-benzylsulfanylmethyl-5-{4-[(4-chlorophenyl)-dimethylaminomethyl]-cyclohexyl}-1-phenethyl-4,5-dihydro-1H-imidazole-4-carboxylic acid methyl ester;

5-{4-[(4-chlorophenyl)-dimethylaminomethyl]-cyclohexylmethyl}-4-(2-methoxycarbonylethyl)-1-phenethyl-4,5-dihydro-1H-imidazole-4-carboxylic acid methyl ester;

1-benzyl-5-{4-[dimethylamino-(3-fluorophenyl)-methyl]-cyclohexyl}-4-(2-methoxycarbonylethyl)-4,5-dihydro-1H-imidazole-4-carboxylic acid methyl ester;

1-benzyl-5-{4-[dimethylamino-(3-fluorophenyl)-methyl]-cyclohexyl}-4-methylsulfanylmethyl-4,5-dihydro-1H-imidazole-4-carboxylic acid methyl ester;

1-benzyl-4-benzylsulfanylmethyl-5-{4-[dimethylamino-(3-fluorophenyl)-methyl]-cyclohexyl}-4,5-dihydro-1H-imidazole-4-carboxylic acid methyl ester;

1-benzyl-4-benzylsulfanylmethyl-5-{4-[(4-chlorophenyl)-dimethylaminomethyl]-cyclohexyl}-4,5-dihydro-1H-imidazole-4-carboxylic acid methyl ester;

1-benzyl-5-{4-[(4-chlorophenyl)-dimethylaminomethyl]-cyclohexylmethyl}-4-(2-methoxycarbonylethyl)-4,5-dihydro-1H-imidazole-4-carboxylic acid methyl ester;

1-benzyl-5-{4-[(4-chlorophenyl)-dimethylaminomethyl]-cyclohexylmethyl}-4-methylsulfanylmethyl-4,5-dihydro-1H-imidazole-4-carboxylic acid methyl ester;

1-benzyl-4-benzylsulfanylmethyl-5-{4-[(4-chlorophenyl)-dimethylaminomethyl]-cyclohexylmethyl}-4,5-dihydro-1H-imidazole-4-carboxylic acid methyl ester;

1-cyclohexyl-5-{4-[dimethylamino-(3-fluorophenyl)-methyl]-cyclohexylmethyl}-4-propyl-4,5-dihydro-1H-imidazole-4-carboxylic acid methyl ester;

1-cyclohexyl-5-{4-[dimethylamino-(3-fluorophenyl)-methyl]-cyclohexylmethyl}-4-(2-methylsulfanylethyl)-4,5-dihydro-1H-imidazole-4-carboxylic acid methyl ester;

1-cyclohexyl-5-{4-[dimethylamino-(3-fluorophenyl)-methyl]-cyclohexylmethyl}-4-methyl-4,5-dihydro-1H-imidazole-4-carboxylic acid methyl ester;

1-cyclohexyl-5-{4-[dimethylamino-(4-fluorophenyl)-methyl]-cyclohexylmethyl}-4-propyl-4,5-dihydro-1H-imidazole-4-carboxylic acid methyl ester;
1-cyclohexyl-5-{4-[dimethylamino-(4-fluorophenyl)-methyl]-cyclohexylmethyl}-4-(2-methylsulfanylethyl)-4,5-dihydro-1H-imidazole-4-carboxylic acid methyl ester;
1-cyclohexyl-5-{4-[dimethylamino-(4-fluorophenyl)-methyl]-cyclohexylmethyl}-4-methyl-4,5-dihydro-1H-imidazole-4-carboxylic acid methyl ester;
1-cyclohexyl-5-[4-(1-dimethylamino-3-phenylpropyl)-cyclohexylmethyl]-4-propyl-4,5-dihydro-1H-imidazole-4-carboxylic acid methyl ester;
1-cyclohexyl-5-[4-(1-dimethylamino-3-phenylpropyl)-cyclohexylmethyl]-4-(2-methylsulfanylethyl)-4,5-dihydro-1H-imidazole-4-carboxylic acid methyl ester;
1-cyclohexyl-5-[4-(1-dimethylamino-3-phenylpropyl)-cyclohexylmethyl]-4-methyl-4,5-dihydro-1H-imidazole-4-carboxylic acid methyl ester;
5-{4-[dimethylamino-(3-fluorophenyl)-methyl]-cyclohexylmethyl}-1,4-dipropyl-4,5-dihydro-1H-imidazole-4-carboxylic acid methyl ester;
5-{4-[dimethylamino-(3-fluorophenyl)-methyl]-cyclohexylmethyl}-4-(2-methylsulfanylethyl)-1-propyl-4,5-dihydro-1H-imidazole-4-carboxylic acid methyl ester;
1-benzyl-4-(4-chlorobenzyl)-5-{4-[(4-chlorophenyl)-dimethylaminomethyl]-cyclohexylmethyl}-4,5-dihydro-1H-imidazole-4-carboxylic acid methyl ester;
1-benzyl-4-butyl-5-{4-[(chlorophenyl)-dimethylaminomethyl]-cyclohexylmethyl}-4,5-dihydro-1H-imidazole-4-carboxylic acid methyl ester;
1-cyclohexyl-5-{4-[dimethylamino-(3-fluorophenyl)-methyl]-cyclohexyl}-4-(2-methoxycarbonylethyl)-4,5-dihydro-1H-imidazole-4-carboxylic acid methyl ester;
4-benzylsulfanylmethyl-1-cyclohexyl-5-{4-[dimethylamino-(3-fluorophenyl)-methyl]-cyclohexyl}-4,5-dihydro-1H-imidazole-4-carboxylic acid methyl ester;
5-{4-[dimethylamino-(3-fluorophenyl)-methyl]-cyclohexylmethyl}-4-methyl-1-propyl-4,5-dihydro-1H-imidazole-4-carboxylic acid methyl ester;
5-{4-[dimethylamino-(4-fluorophenyl)-methyl]-cyclohexylmethyl}-1,4-dipropyl-4,5-dihydro-1H-imidazole-4-carboxylic acid methyl ester;
5-{4-[dimethylamino-(4-fluorophenyl)-methyl]-cyclohexylmethyl}-4-(2-methylsulfanylethyl)-1-propyl-4,5-dihydro-1H-imidazole-4-carboxylic acid methyl ester;
5-[4-(1-dimethylamino-3-phenylpropyl)-cyclohexylmethyl]-1,4-dipropyl-4,5-dihydro-1H-imidazole-4-carboxylic acid methyl ester;
5-[4-(1-dimethylamino-3-phenylpropyl)-cyclohexylmethyl]-4-(2-methylsulfanylethyl)-1-propyl-4,5-dihydro-1H-imidazole-4-carboxylic acid methyl ester;
1-butyl-5-{4-[dimethylamino-(3-fluorophenyl)-methyl]-cyclohexylmethyl}-4-propyl-4,5-dihydro-1H-imidazole-4-carboxylic acid methyl ester;
1-butyl-5-{4-[dimethylamino-(3-fluorophenyl)-methyl]-cyclohexylmethyl}-4-(2-methylsulfanylethyl)-4,5-dihydro-1H-imidazole-4-carboxylic acid methyl ester;
1-butyl-5-{4-[dimethylamino-(3-fluorophenyl)-methyl]-cyclohexylmethyl}-4-methyl-4,5-dihydro-1H-imidazole-4-carboxylic acid methyl ester;
1-butyl-5-{4-[dimethylamino-(4-fluorophenyl)-methyl]-cyclohexylmethyl}-4-propyl-4,5-dihydro-1H-imidazole-4-carboxylic acid methyl ester;
1-butyl-5-{4-[dimethylamino-(4-fluorophenyl)-methyl]-cyclohexylmethyl}-4-(2-methylsulfanylethyl)-4,5-dihydro-1H-imidazole-4-carboxylic acid methyl ester;
1-butyl-5-[4-(1-dimethylamino-3-phenylpropyl)-cyclohexylmethyl]-4-propyl-4,5-dihydro-1H-imidazole-4-carboxylic acid methyl ester;
1-butyl-5-[4-(1-dimethylamino-3-phenylpropyl)-cyclohexylmethyl]-4-(2-methylsulfanylethyl)-4,5-dihydro-1H-imidazole-4-carboxylic acid methyl ester;
5-{4-[dimethylamino-(3-fluorophenyl)-methyl]-cyclohexylmethyl}-1-phenethyl-4-propyl-4,5-dihydro-1H-imidazole-4-carboxylic acid methyl ester;
5-{4-[dimethylamino-(3-fluorophenyl)-methyl]-cyclohexylmethyl}-4-(2-methylsulfanylethyl)-1-phenethyl-4,5-dihydro-1H-imidazole-4-carboxylic acid methyl ester;
5-{4-[dimethylamino-(3-fluorophenyl)-methyl]-cyclohexylmethyl}-4-methyl-1-phenethyl-4,5-dihydro-1H-imidazole-4-carboxylic acid methyl ester;
5-{4-[dimethylamino-(4-fluorophenyl)-methyl]-cyclohexylmethyl}-1-phenethyl-4-propyl-4,5-dihydro-1H-imidazole-4-carboxylic acid methyl ester;
5-{4-[dimethylamino-(4-fluorophenyl)-methyl]-cyclohexylmethyl}-4-(2-methylsulfanylethyl)-1-phenethyl-4,5-dihydro-1H-imidazole-4-carboxylic acid methyl ester;
5-{4-[dimethylamino-(4-fluorophenyl)-methyl]-cyclohexylmethyl}-4-methyl-1-phenethyl-4,5-dihydro-1H-imidazole-4-carboxylic acid methyl ester;
5-[4-(1-dimethylamino-3-phenylpropyl)-cyclohexylmethyl]-1-phenethyl-4-propyl-4,5-dihydro-1H-imidazole-4-carboxylic acid methyl ester;
5-[4-(1-dimethylamino-3-phenylpropyl)-cyclohexylmethyl]-4-(2-methylsulfanylethyl)-1-phenethyl-4,5-dihydro-1H-imidazole-4-carboxylic acid methyl ester;
5-[4-(1-dimethylamino-3-phenylpropyl)-cyclohexylmethyl]-4-methyl-1-phenethyl-4,5-dihydro-1H-imidazole-4-carboxylic acid methyl ester;
1-benzyl-5-{4-[dimethylamino-(3-fluorophenyl)-methyl]-cyclohexylmethyl}-4-propyl-4,5-dihydro-1H-imidazole-4-carboxylic acid methyl ester;
1-benzyl-5-{4-[dimethylamino-(3-fluorophenyl)-methyl]-cyclohexylmethyl}-4-(2-methylsulfanylethyl)-4,5-dihydro-1H-imidazole-4-carboxylic acid methyl ester;
1-benzyl-5-{4-[dimethylamino-(3-fluorophenyl)-methyl]-cyclohexylmethyl}-4-methyl-4,5-dihydro-1H-imidazole-4-carboxylic acid methyl ester;
1-benzyl-5-{4-[dimethylamino-(4-fluorophenyl)-methyl]-cyclohexylmethyl}-4-propyl-4,5-dihydro-1H-imidazole-4-carboxylic acid methyl ester;
1-benzyl-5-{4-[dimethylamino-(4-fluorophenyl)-methyl]-cyclohexylmethyl}-4-(2-methylsulfanylethyl)-4,5-dihydro-1H-imidazole-4-carboxylic acid methyl ester;
1-benzyl-5-{4-[dimethylamino-(4-fluorophenyl)-methyl]-cyclohexylmethyl}-4-methyl-4,5-dihydro-1H-imidazole-4-carboxylic acid methyl ester;
1-benzyl-5-[4-(1-dimethylamino-3-phenylpropyl)-cyclohexylmethyl]-4-propyl-4,5-dihydro-1H-imidazole-4-carboxylic acid methyl ester;
1-benzyl-5-[4-(1-dimethylamino-3-phenylpropyl)-cyclohexylmethyl]-4-(2-methylsulfanylethyl)-4,5-dihydro-1H-imidazole-4-carboxylic acid methyl ester;
1-benzyl-5-[4-(1-dimethylamino-3-phenylpropyl)-cyclohexylmethyl]-4-methyl-4,5-dihydro-1H-imidazole-4-carboxylic acid methyl ester;

1-cyclohexyl-5-{4-[dimethylamino-(3-fluorophenyl)-methyl]-cyclohexylmethyl}-4-(2-methoxycarbonylethyl)-4,5-dihydro-1H-imidazole-4-carboxylic acid methyl ester;

4-sec-butyl-1-cyclohexyl-5-{4-[dimethylamino-(3-fluorophenyl)-methyl]-cyclohexylmethyl}-4,5-dihydro-1H-imidazole-4-carboxylic acid methyl ester;

1-cyclohexyl-5-{4-[dimethylamino-(3-fluorophenyl)-methyl]-cyclohexylmethyl}-4-methylsulfanylmethyl-4,5-dihydro-1H-imidazole-4-carboxylic acid methyl ester;

4-benzylsulfanylmethyl-1-cyclohexyl-5-{4-[dimethylamino-(3-fluorophenyl)-methyl]-cyclohexylmethyl}-4,5-dihydro-1H-imidazole-4-carboxylic acid methyl ester;

1-cyclohexyl-5-{4-[dimethylamino-(4-fluorophenyl)-methyl]-cyclohexylmethyl}-4-(2-methoxycarbonylethyl)-4,5-dihydro-1H-imidazole-4-carboxylic acid methyl ester;

4-sec-butyl-1-cyclohexyl-5-{4-[dimethylamino-(4-fluorophenyl)-methyl]-cyclohexylmethyl}-4,5-dihydro-1H-imidazole-4-carboxylic acid methyl ester;

1-cyclohexyl-5-{4-[dimethylamino-(4-fluorophenyl)-methyl]-cyclohexylmethyl}-4-methylsulfanylmethyl-4,5-dihydro-1H-imidazole-4-carboxylic acid methyl ester;

1-cyclohexyl-5-[4-(1-dimethylamino-3-phenylpropyl)-cyclohexylmethyl]-4-(2-methoxycarbonylethyl)-4,5-dihydro-1H-imidazole-4-carboxylic acid methyl ester;

1-cyclohexyl-5-[4-(1-dimethylamino-3-phenylpropyl)-cyclohexylmethyl]-4-methylsulfanylmethyl-4,5-dihydro-1H-imidazole-4-carboxylic acid methyl ester;

4-benzylsulfanylmethyl-1-cyclohexyl-5-[4-(1-dimethylamino-3-phenylpropyl)-cyclohexylmethyl]-4,5-dihydro-1H-imidazole-4-carboxylic acid methyl ester;

5-{4-[dimethylamino-(3-fluorophenyl)-methyl]-cyclohexylmethyl}-4-(2-methoxycarbonylethyl)-1-propyl-4,5-dihydro-1H-imidazole-4-carboxylic acid methyl ester;

5-{4-[dimethylamino-(3-fluorophenyl)-methyl]-cyclohexylmethyl}-4-methylsulfanylmethyl-1-propyl-4,5-dihydro-1H-imidazole-4-carboxylic acid methyl ester;

5-{4-[dimethylamino-(4-fluorophenyl)-methyl]-cyclohexylmethyl}-4-(2-methoxycarbonylethyl)-1-propyl-4,5-dihydro-1H-imidazole-4-carboxylic acid methyl ester;

5-{4-[dimethylamino-(4-fluorophenyl)-methyl]-cyclohexylmethyl}-4-methylsulfanylmethyl-1-propyl-4,5-dihydro-1H-imidazole-4-carboxylic acid methyl ester;

4-benzylsulfanylmethyl-5-{4-[dimethylamino-(4-fluorophenyl)-methyl]-cyclohexylmethyl}-1-propyl-4,5-dihydro-1H-imidazole-4-carboxylic acid methyl ester; and methyl-4-sec-butyl-5-((4-(4-chlorophenyl)(dimethylamino)methyl)cyclohexyl)-methyl)-1-cyclohexyl-4,5-dihydro-1H-imidazole-4-carboxylate;

or a salt thereof with a physiologically compatible acid.

14. A pharmaceutical composition comprising a compound as claimed in claim 1 and at least one pharmaceutically acceptable carrier or auxiliary substance.

15. A process for preparing a compound as claimed in claim 1, said process comprising reacting an amine corresponding to Formula A with an aldehyde corresponding to Formula B and an isonitrile ester corresponding to Formula C in an organic solvent at a temperature of 20°-100° C. in accordance with the following reaction scheme:

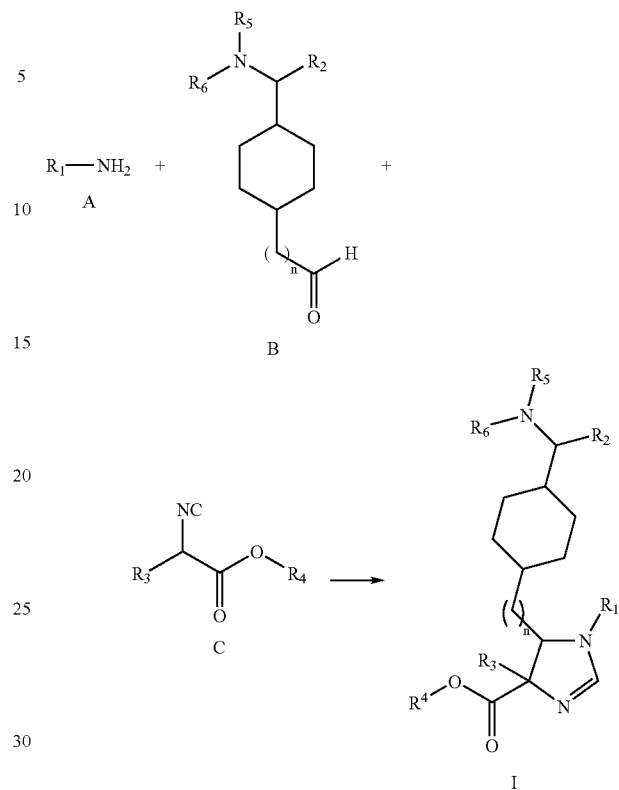

to obtain a substituted imidazoline compound corresponding to Formula I wherein $R^1$ through $R^6$ and n have the meanings given in claim 1.

16. A process as claimed in claim 15, wherein said solvent is ethanol or methanol.

17. A method of treating a condition selected from the group consisting of pain, depression, urinary incontinence, diarrhea, pruritus, alcohol and drug misuse, drug dependency, lethargy and anxiety in a subject in need thereof, said method comprising administering to said subject a pharmacologically effective amount of a compound as claimed in claim 1.

18. A method as claimed in claim 17, wherein said condition is pain.

19. A method as claimed in claim 18, wherein said pain is acute pain, neuropathic pain or chronic pain.

20. A substituted aldehyde compound corresponding to Formula B:

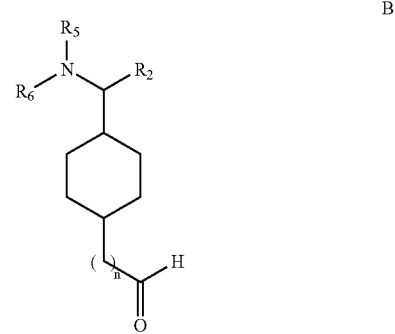

wherein

R² denotes an optionally mono- or polysubstituted aryl or heteroaryl group; or an optionally mono- or polysubstituted aryl group bonded via a $C_{1-3}$-alkylene chain;

R⁵ and R⁶ independently denote H or saturated or unsaturated, branched or unbranched $C_{1-6}$-alkyl, with the proviso that R⁵ and R⁶ do not simultaneously denote H, or R⁵ and R⁶ together denote —CH₂CH₂OCH₂CH₂—, or —(CH₂)$_{3-6}$—; and n is 0, 1 or 2;

or a salt thereof with a physiologically compatible acid.

21. A compound as claimed in claim 20, wherein R² denotes:

phenyl or thienyl, which is unsubstituted or mono- or polysubstituted with F, Cl, CN, NO₂, SH, S—$C_{1-6}$-alkyl, OH, O—$C_{1-6}$-alkyl, CO₂H, CO₂—$C_{1-6}$-alkyl, CF₃, or $C_{1-6}$-alkyl; or a phenyl group bonded via a $C_{1-3}$-alkyl chain, wherein the phenyl group is unsubstituted or mono- or polysubstituted with F, Cl, CN, NO₂, SH, S—$C_{1-6}$-alkyl, OH, O—$C_{1-6}$-alkyl, CO₂H, CO₂—$C_{1-6}$-alkyl, CF₃, or $C_{1-6}$-alkyl.

22. A compound as claimed in claim 21, wherein R² denotes phenyl which is unsubstituted or monosubstituted with Cl or F, or thienyl or phenethyl.

23. A compound as claimed in claim 20, wherein R⁵ and R⁶ each denote CH₃.

24. A compound as claimed in claim 20, selected from the group consisting of:

4-[dimethylamino-(4-fluorophenyl)-methyl]-cyclohexanecarbaldehyde;

4-(1-dimethylamino-3-phenylpropyl)-cyclohexanecarbaldehyde;

4-[dimethylamino-(3-fluorophenyl)-methyl]-cyclohexanecarbaldehyde;

4-[(4-chlorophenyl)-dimethylaminomethyl]-cyclohexanecarbaldehyde;

{4-[(4-chlorophenyl)-dimethylaminomethyl]-cyclohexyl}-acetaldehyde;

{4-[dimethylamino-(3-fluorophenyl)-methyl]-cyclohexyl}-acetaldehyde;

4-(dimethylamino-thiophen-2-yl-methyl)-cyclohexanecarbaldehyde;

{4-[dimethylamino-(4-fluorophenyl)-methyl]-cyclohexyl}-acetaldehyde; and

[4-(dimethylamino-thiophen-2-yl-methyl)-cyclohexyl]-acetaldehyde; and

[4-(1-dimethylamino-3-phenylpropyl)-cyclohexyl]-acetaldehyde;

or a salt thereof with a physiologically compatible acid.

25. A pharmaceutical composition comprising a compound as claimed in claim 20 and at least one pharmaceutically acceptable carrier or auxiliary substance.

26. A method of treating a condition selected from the group consisting of pain, depression, urinary incontinence, diarrhea, pruritus, alcohol and drug misuse, drug dependency, lethargy and anxiety in a subject in need thereof, said method comprising administering to said subject a pharmacologically effective amount of a compound as claimed in claim 1.

27. A method as claimed in claim 26, wherein said condition is pain.

28. A method as claimed in claim 27, wherein said pain is acute pain, neuropathic pain or chronic pain.

* * * * *